United States Patent
Kerfeld et al.

(10) Patent No.: US 11,198,880 B2
(45) Date of Patent: Dec. 14, 2021

(54) METHODS FOR PRODUCING MICROCOMPARTMENTS

(71) Applicant: The Regents of the University of California, Oakland, CA (US)

(72) Inventors: Cheryl A. Kerfeld, Walnut Creek, CA (US); Jonathan K. Lassila, South San Francisco, CA (US); James N. Kinney, Clayton, CA (US); Markus Sutter, Berkeley, CA (US); Steven C. Wilson, Rohnert Park, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/367,089

(22) Filed: Dec. 1, 2016

(65) Prior Publication Data

US 2017/0107523 A1     Apr. 20, 2017

Related U.S. Application Data

(63) Continuation of application No. 14/214,172, filed on Mar. 14, 2014, which is a continuation-in-part of application No. 13/367,260, filed on Feb. 6, 2012, which is a continuation-in-part of application No. PCT/US2010/044455, filed on Aug. 4, 2010.

(60) Provisional application No. 61/800,118, filed on Mar. 15, 2013, provisional application No. 61/231,246, filed on Aug. 4, 2009.

(51) Int. Cl.
| | |
|---|---|
| *C12N 15/70* | (2006.01) |
| *C12N 15/67* | (2006.01) |
| *C12N 15/52* | (2006.01) |
| *C12N 15/81* | (2006.01) |
| *C07K 14/35* | (2006.01) |
| *C12N 9/02* | (2006.01) |
| *C12N 15/65* | (2006.01) |

(52) U.S. Cl.
CPC .............. *C12N 15/70* (2013.01); *C07K 14/35* (2013.01); *C12N 9/0008* (2013.01); *C12N 15/52* (2013.01); *C12N 15/65* (2013.01); *C12N 15/67* (2013.01); *C12N 15/81* (2013.01); *C12Y 102/01004* (2013.01); *C12Y 401/01039* (2013.01)

(58) Field of Classification Search
None
See application file for complete search history.

(56) References Cited

U.S. PATENT DOCUMENTS

| | | |
|---|---|---|
| 6,964,868 B1 | 11/2005 | Williams et al. |
| 2002/0042931 A1 | 4/2002 | Kaplan et al. |
| 2006/0080747 A1 | 4/2006 | Keetman et al. |
| 2002/0210459 | 8/2012 | Kerfeld et al. |

FOREIGN PATENT DOCUMENTS

| | | |
|---|---|---|
| WO | WO 2011/017458 A1 * | 2/2011 |
| WO | WO 2011/017458 A1 | 2/2011 |

OTHER PUBLICATIONS

Kerfeld et al., 2010, Annu. Rev. Microbiol. 64: 391-408.*
Salis et al., 2009, Nature Biotechnology 27: 946-950.*
Kerfeld et al., 2005, Science 309: 936-938 with supplementary materials.*
PET-22b(+) vector map and sequence, Cat. No. 69744-3, Novagen.*
Axen et al., 2014, PLoS Computational Biology 10(10): e1003898. doi: 10.1371/journal.pcbi.1003898.*
Fan et al., 2010, Proc. Nat. Acad. Sci. 107: 7509-7514, with supporting information.*
Romier et al., 2006, Co-expression of protein complexes in prokaryotic and eukaryotic hosts: experimental procedures, database tracking and case studies, Acta Crystallographies Section D62: 1232-1242.*
Parsons et al., 2010, Synthesis of Empty Bacterial Microcompartments, Directed Organelle Protein Incorporation, and Evidence of Filament-Associated Organelle Movement, Molecular Cell 38: 305-315, with supplementary information.*
Amichay, et al. Construction of a Synechocystis PCC6803 Mutant Suitable for the Study of Variant Hexadecameric Ribulose Bisphosphate Carboxylase/Oxygenase Enzymes. Plant Molecular Biology. 1993. 23. pp. 465-476: abstract; p. 466, col. 1. para 1; p. 472, col. 2. para 1 to p. 473, col. 1. para 1; p. 474. col. 1. para 1.
Bobik, T. A. Polyhedral organelles compartmenting bacterial metabolic processes. Appl. Microbiol. Biotechnol. 70, 517-525 (2006).
Cheng et al., "Bacterial microcompartments: their properties and paradoxes", BioEssays, Nov. 2008, vol. 30, No. 11-12, pp. 1084-1095.
Choudary et al., Engineered Protein Nano-Compartments for Targeted Enzyme Localization, 7 PLoSONE No. 3, 1-12(2012).
Frank et al., Bacterial microcompartments moving into a synthetic biological world, 163 J Biotech, 273-279 at 277 (2013).
GenBank Accession No. Y1424_SYNE7 (Jan. 19, 2010) [Retrieved from the Internet Apr. 28, 2011: <http://www.ncbi.nlm.nih.gov/protein/1176826?sat=OLD07&satkey=7901992>).

(Continued)

*Primary Examiner* — Bratislav Stankovic
(74) *Attorney, Agent, or Firm* — Knobbe, Martens, Olson & Bear LLP

(57) ABSTRACT

To produce a bacterial microcompartment shell, or a designed shell based on naturally occurring bacterial microcompartment shells in a new host organism, a synthetic operon is constructed that contains the desired shell protein genes and translation efficiency is controlled by host specific ribosomal binding sites. Proteins or other molecules can be encapsulated in the microcompartment shells by various methods described herein. The constructs can also be used to express self-assembling sheets comprised of shell proteins.

18 Claims, 16 Drawing Sheets

Specification includes a Sequence Listing.

(56) References Cited

OTHER PUBLICATIONS

Havemann, G.D. and T.A. Bobik, Protein content of polyhedral organelles involved in coenzyme B12-dependent degradation of 1,2-propanediol in *Salmonella enterica* serovar typhimurium LT2. Journal of Bacteriology, 2003. 185: p. 5086-5095.
Heinhorst et al., Carboxysomes and Carboxysome-like inclusions, 2 Microbiol Monogr, 141-165 in Complex Intracellular Structures in Prokaryotes (2006)).
Invitation to Pay Additional Fees mailed May 16, 2011 for PCT International Application No. PCT/US2011/023416 filed Feb. 1, 2011.
International Search Report dated Oct. 1, 2010 for International patent application PCT/US2010/044455 filed Aug. 4, 2010.
International Search Report dated Jul. 22, 2011 for PCT International Application No. PCT/US2011/023416 filed Feb. 1, 2011.
Kerfeld et al., Protein Structures Forming the Shell of Primitive Bacterial Organelles, 309 Science, 936-938 at 937-938 (2005)).
Kerfeld, C.A., S. Heinhorst, and G.C. Cannon, Bacterial Microcompartments. Annual Review of Microbiology, 2010. 64: p. 391-408.
NIH: NCBI. Accession No. CP000480. Oct. 2006. Retrieved from the Internet: http://www.ncbi.nlm.nih.gov/sviewer/?noredirect=1&db=nuccore&val=CP000480.1&fmt_mask=295416.
Parsons et al., Biochemical and Structural Insights into Bacterial Organelle Form and Biogenesis, 283 JBC, 14366-14375 (2008).

Uniprot Direct Submission. Accession No. Q5N5U6_SYNP6. 01. Carbon Dioxide Concentrating Mechanism Protein. Feb. 2005 [Retrieved from the Internet Jul. 13, 2011 :<URL: http://www.uniprot.org!uniproVQ5N5U6.txt?version;1>), p. 1.
Written Opinion dated Oct. 1, 2010 for International patent application PCT/US2010/044455 filed Aug. 4, 2010.
Written Opinion dated Jul. 22, 2011 for International patent application PCT/US2011/023416 filed Feb. 1, 2011.
Yeates, T.O., Kerfeld, C.A., Heinhorst, S., Cannon, G.C. and Shively, J. Protein-Based Organelles in Bacteria: Carboxysomes and Related Microcompartments. Nat Rev Microbiol. Sep. 2008;6(9):681-91. Review, online on Aug. 4, 2008.
Zhang, et al. Four Novel Genes Required for Optimal Photoautotrophic Growth of the 1-2, 3a-3b and 4 y Cyanobacterium *Synechocystis* sp. Strain PCC 6803 Identified by In Vitro Transposon Mutagenesis. Journal of Bacteriology 2004.186(3):875-879: table 1; abstract; p. 876. col. 1, para 2.
Friedberg et al., J. Bacteriology, 171(11), 6069-6076, 1989.
Cai, et al., Production and Characterization of Synthetic Carboxysome Shells with Incorporated Luminal Proteins, Plant Physiol. Jan. 20, 2016, p. 01822.2015.
Lassila, et al., Assembly of robust bacterial microcompartment shells using building blocks from an organelle of unknown function. J Mol Biol. May 29, 2014; 426(11):2217-28.
Tanaka, et al., Atomic-Level Models of the Bacterial Carboxysome Shell, Science 2008; 319: 1083-86.

\* cited by examiner

Hexamer (BMC-H)

Tandem Domain (BMC-T)

Pentamer (BMC-P)

FIG. 13A
FIG. 13B
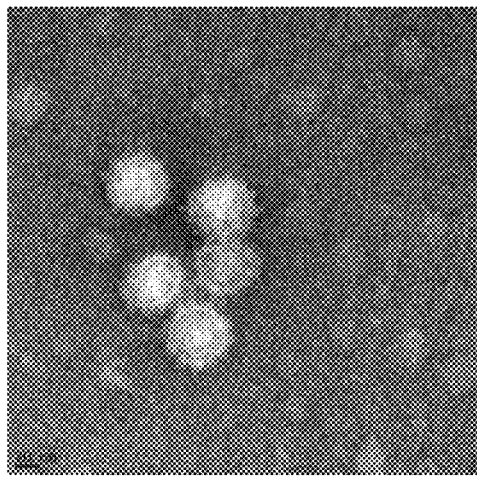
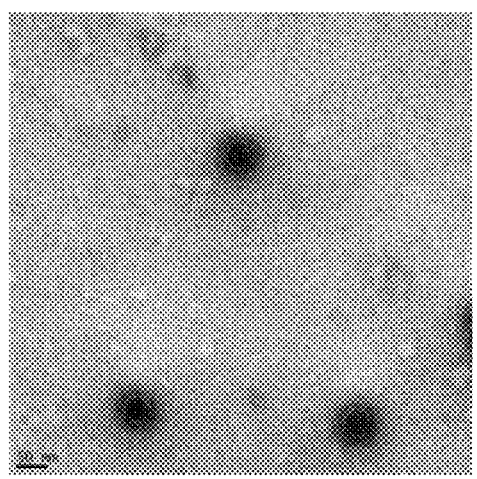
FIG. 13C
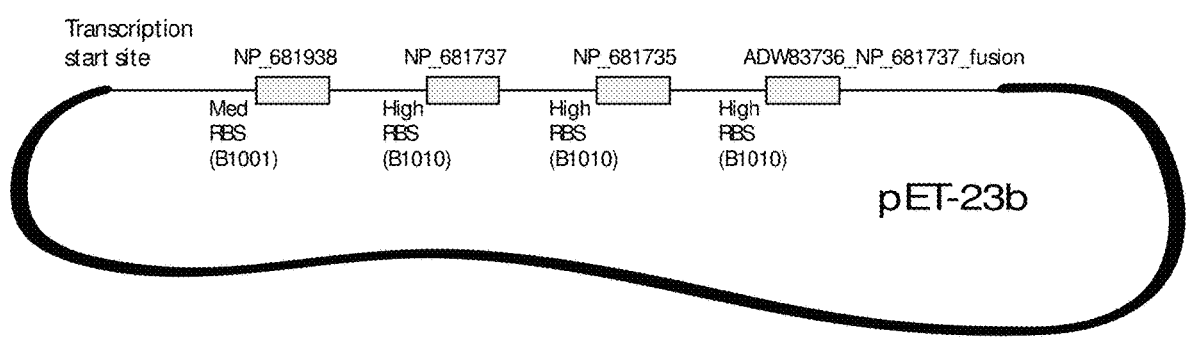

Angle Between Gold Particles, Degrees

Dashed line: random distribution in two dimensions

Solid line: random distribution in three dimensions

FIG. 16D
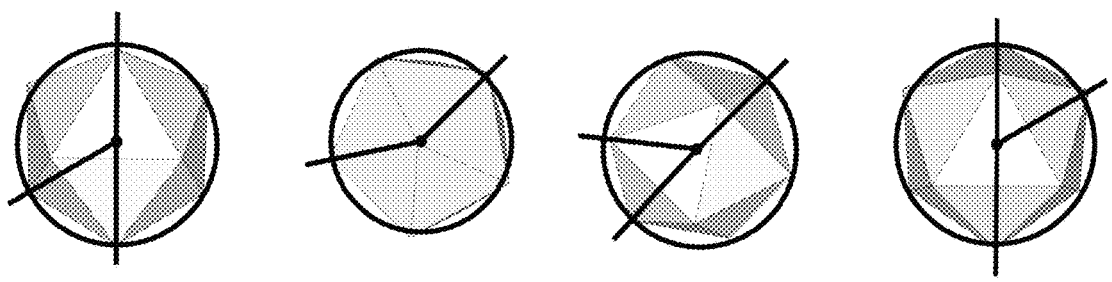
FIG. 17A
FIG. 17B
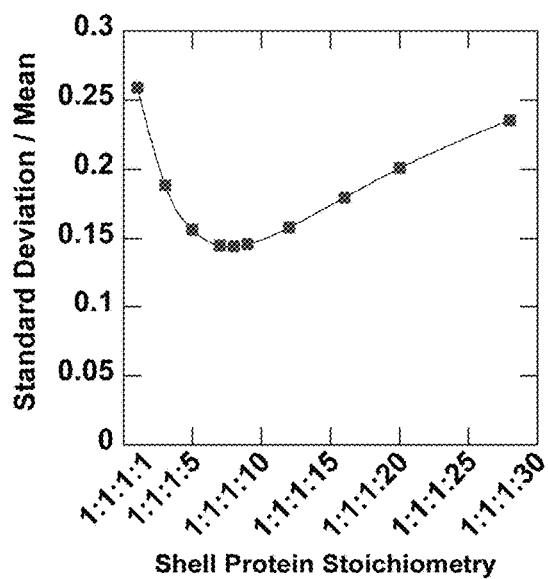
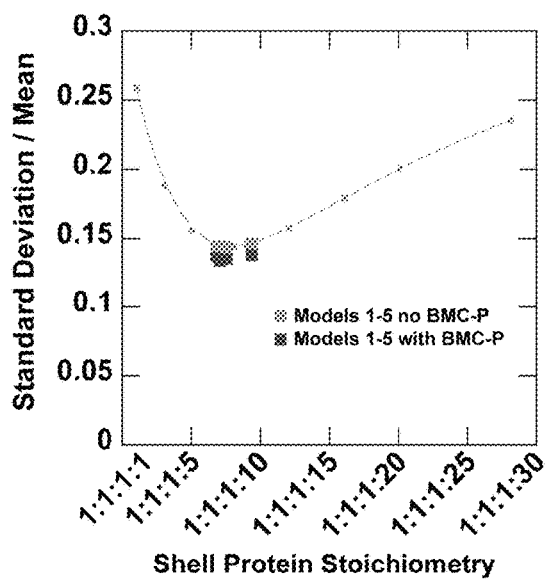

METHODS FOR PRODUCING MICROCOMPARTMENTS

CROSS-REFERENCE TO RELATED APPLICATIONS

This application is a continuation application of U.S. patent application Ser. No. 14/214,172, filed on Mar. 14, 2014, which claims the benefit of U.S. Provisional Patent Application No. 61/800,118, filed on Mar. 15, 2013. This application is also a continuation-in-part application of U.S. patent application Ser. No. 13/367,260, filed on Feb. 6, 2012, which is a continuation-in-part of International Application No. PCT/US2010/044455, filed on Aug. 4, 2010, which claims the benefit of U.S. Provisional Patent Application No. 61/231,246, filed on Aug. 4, 2009. The contents of these related applications are hereby incorporated by reference in their entireties for all purposes.

This application is related to U.S. patent application Ser. No. 13/564,676, filed on Aug. 1, 2012, hereby incorporated by reference in its entirety.

STATEMENT OF GOVERNMENTAL SUPPORT

This invention was made with government support under Contract No. DE-AC02-05CH11231 awarded by the U.S. Department of Energy, under Contract No. DE-0000200 awarded by the Department of Energy ARPA-E, and under Grant Nos. MCB0851094 and MCB1160614 awarded by the National Science Foundation. The government has certain rights in the invention.

REFERENCE TO SEQUENCE LISTING AND TABLES

This application also incorporates by reference the attached sequence listing which is also found in computer-readable form in a *.txt file entitled, "LBNL_073C1.txt", created on Dec. 1, 2016.

BACKGROUND OF THE INVENTION

Field of the Invention

The present invention relates to synthetic biology, especially using operons and synthetic constructs to produce microcompartments and bacterial microcompartment shells and to integrate molecules and proteins into these microcompartments, or on the microcompartment surface.

Related Art

Bacterial microcompartments (BMCs) encapsulate enzymes and metabolic pathways. The most well-known type of BMC is the carboxysome, which fixes $CO_2$ in cyanobacteria. Several other types of BMC gene clusters have been identified in prokaryotes, including the propanediol utilization and ethanolamine utilization microcompartment gene clusters.

The shells of BMCs are composed of multiple paralogs of proteins containing BMC domains pfam00936 and pfam03319. Three types of shell proteins have been identified: single pfam00936 domains ("hexamer"), fusion proteins composed of two pfam00936 domains ("tandem domain"), and single pfam03319 domains ("pentamer"). Hexamer and tandem domain proteins are the major components of known microcompartment shells, while pentamer proteins are minor components. Natural BMC gene clusters vary widely in composition and gene arrangement and are defined by genes that encode shell proteins. Three types of BMC shell proteins exist, identified here as hexamers or BMC-H, tandem domains or BMC-T, and pentamers or BMC-P, that together form polyhedral shells (FIG. 1). BMC-H polypeptides contain a single domain of the pfam00936 family from the pfam database (Punta, M., Coggill, P. C., Eberhardt, R. Y., Mistry, J. & Tate, J. e. a. (2012). The Pfam protein families database. *Nucleic Acids Research* 40, D290-D301), about 90 amino acids, that assembles into a six-fold symmetric hexamer in crystal structures. This type of subunit represents the most abundant component of characterized BMC shells. Tandem domains (BMC-T) contain two pfam00936 domains in a single polypeptide. These proteins form trimers with a pseudo-hexameric configuration that are sometimes found stacked into a double layer in crystal structures. (Klein, M. G., Zwart, P., Bagby, S. C., Cai, F., Chisholm, S. W., Heinhorst, S., Cannon, G. C. & Kerfeld, C. A. (2009). Identification and structural analysis of a novel carboxysome shell protein with implications for metabolite transport. *Journal of Molecular Biology* 392, 319-333; Cai, F., Sutter, M., Cameron, J. C., Stanley, D. N., Kinney, J. N. & Kerfeld, C. A. (2013). The structure of CcmP, a tandem bacterial microcompartment domain protein from the β-carboxysome forms a subcompartment within a microcompartment. *Journal of Biological Chemistry* 288, 16055-16063). The third type, referred to here as pentamers or BMC-P, contain a single domain of the pfam03319 family. The five-fold symmetric assemblies formed by these proteins are presumed to occupy the vertices of icosahedral shells. Accordingly, they are a minor component of characterized BMC shells; only 60 copies of the gene product (12 pentamers) are required to close an icosahedral shell.

Previously others have expressed only naturally existing microcompartment operons or partial operons in heterologous hosts. See Bonacci W, Teng P K, Afonso B, Niederholtmeyer H, Grob P, Silver P A, Savage D F, Modularity of a carbon-fixing protein organelle, *Proc. Natl. Acad. Sci. USA* 2012 Jan. 10; 109(2):478-83.Epub 2011 Dec. 19. However, a general approach for producing synthetic microcompartment shell operons, synthetic microcompartment shells and integrating molecules into microcompartments has not been described.

BRIEF SUMMARY OF THE INVENTION

The present invention provides for constructs and systems and methods for producing microcompartments and microcompartment shells or protein scaffolds based on microcompartment architecture.

In one embodiment, the present invention provides for a construct or an expression cassette comprising a polynucleotide encoding a cluster of microcompartment genes, wherein the cluster comprises a set of microcompartment genes necessary for the expression of a microcompartment shell in a host cell, and wherein at least one of the genes is preceded by a ribosomal binding site to control expression in said host cell.

The expression cassette can be used to provide a cell comprising in its genome at least one stably incorporated expression cassette, where the expression cassette comprising a heterologous nucleotide sequence or a fragment thereof operably linked to a promoter that drives expression in the cell and operably linked to a ribosomal binding site that controls expression efficiency in the cell.

The present invention further describes methods for production of BMCs in bacterial hosts such as *Escherichia coli* and other host organisms. In one embodiment, a method comprising producing a synthetic operon for expression of shell protein genes in a host organism with a specific ordering of the genes and a specific set of ribosomal binding site (RBS) sequences to produce the shell proteins in desired ratios. In some embodiments, the method further comprises coexpression with peptide tag sequences for incorporation of proteins into the microcompartment shells. In other embodiments, the method further comprises coexpression of microcompartments with proteins without peptide tag sequences for incorporation of proteins into the microcompartment shells.

Also provided are methods for enhancing metabolic activity in an organism. In one method, comprising introducing into an organism at least one expression cassette operably linked to a promoter that drives expression in the organism, where the expression cassette comprising a cluster of microcompartment genes identified from a bacterial species, wherein the cluster comprising a set microcompartment genes necessary for the expression of a microcompartment that has metabolic activity, wherein the microcompartment genes further comprise a polynucleotide or a fragment thereof which acts as a ribosomal binding site that controls expression efficiency in the organism.

In various embodiments, a common motif (peptide) found in a subset of proteins presumed to be encapsulated in functionally diverse bacterial microcompartments (BMCs), and adjacent linker regions can also be included in the construct for targeting proteins to BMCs. All BMC targeting peptides share general properties such as a region predicted to have an alpha helical conformation, adjacent to poorly conserved segment(s) of primary structure enriched in proline and glycine; for each type of encapsulated protein, for each functionally distinct BMC. Amino acid properties are conserved in many of the positions within these peptides. In some embodiments, previously identified consensus targeting peptides specific to various BMC types can be used with the present constructs, systems and methods.

In one embodiment, shell proteins are described and methods for assembling *Haliangium ochraceum* shell proteins into a synthetic operon, producing the *H. ochraceum* microcompartment shells in *Escherichia coli* as the host organism, and incorporating proteins into the microcompartment shells using *H. ochraceum* peptide tag sequences are described.

BRIEF DESCRIPTION OF THE SEQUENCES

SEQ ID NO:1 is a high ribosomal binding site (RBS) sequence from *E. coli*.

SEQ ID NO:2 is a medium RBS sequence that promotes medium translation efficiency in *E. coli*.

SEQ ID NO:3 is a low RBS sequence that promotes low translation efficiency in *E. coli*.

SEQ ID NO:4 is the natural RBS site from the *H. neapolitanus* shell protein CsoS1C.

SEQ ID NO:5 is a DNA sequence that encodes a polypeptide of Verminephrobacter eiseniae EF01-2.

SEQ ID NO:6 is a BMC gene product identified from *Haliangium ochraceum* SMP-2, DSM 14365.

SEQ ID NO:7 is a DNA sequence selected to encode the protein sequence of SEQ ID NO:6 while utilizing high-frequency codons from *E. coli*, the host organism.

SEQ ID NO:8 is a BMC gene product identified from *Haliangium ochraceum* SMP-2, DSM 14365.

SEQ ID NO:9 is a DNA sequence selected to encode the protein sequence of SEQ ID NO:8 while utilizing high-frequency codons from *E. coli*, the host organism.

SEQ ID NO:10 is a BMC gene product identified from *Haliangium ochraceum* SMP-2, DSM 14365.

SEQ ID NO:11 is a DNA sequence selected to encode the protein sequence of SEQ ID NO:10 while utilizing high-frequency codons from *E. coli*, the host organism.

SEQ ID NO:12 is a BMC gene product identified from *Haliangium ochraceum* SMP-2, DSM 14365.

SEQ ID NO:13 is a DNA sequence selected to encode the protein sequence of SEQ ID NO:12 while utilizing high-frequency codons from *E. coli*, the host organism.

SEQ ID NO:14 is a BMC gene product identified from *Haliangium ochraceum* SMP-2, DSM 14365.

SEQ ID NO:15 is a DNA sequence selected to encode the protein sequence of SEQ ID NO:14 while utilizing high-frequency codons from *E. coli*, the host organism.

SEQ ID NO:16 is a BMC gene product identified from *Haliangium ochraceum* SMP-2, DSM 14365.

SEQ ID NO:17 is a DNA sequence selected to encode the protein sequence of SEQ ID NO:16 while utilizing high-frequency codons from *E. coli*, the host organism.

SEQ ID NO:18 is a BMC gene product identified from *Haliangium ochraceum* SMP-2, DSM 14365.

SEQ ID NO:19 is a DNA sequence selected to encode the protein sequence of SEQ ID NO:18 while utilizing high-frequency codons from *E. coli*, the host organism.

SEQ ID NO:20 is a RBS sequence.

SEQ ID NO:21 is a RBS sequence.

SEQ ID NO:22 is a RBS sequence.

SEQ ID NO:23 is a protein sequence that was fused to the N-terminus of GFP in a Tag-GFP construct.

SEQ ID NO:24 is a DNA sequence used with Tag-GFP construct of SEQ ID: 23 derived from the N-terminus of an aldehyde dehydrogenase from *H. ochraceum*.

SEQ ID NO:25 is a protein sequence that was fused to the N-terminus of GFP of a full Enzyme-GFP construct with protein derived from aldehyde dehydrogenase (Protein accession number YP_003270182; Locus tag: Hoch_5813).

SEQ ID NO:26 is DNA sequence used to encode the fused protein of SEQ ID NO:25.

SEQ ID NO:27 is a protein sequence fused to C-terminus of GFP of a noncognate Tag-GFP construct.

SEQ ID NO:28 is a DNA sequence fused to the 3' end of the DNA encoding GFP of a noncognate Tag-GFP construct.

SEQ ID NO:29 is a RBS sequence for operon of Example 4.

SEQ ID NO:30 is a protein sequence of YP_884687.

SEQ ID NO:31 is a DNA sequence of YP_884687.

SEQ ID NO:32 is a RBS sequence for operon of Example 4.

SEQ ID NO:33 is a protein sequence of YP_884690.

SEQ ID NO:34 is a DNA sequence of YP_884690.

SEQ ID NO:35 is a RBS sequence for operon of Example 4.

SEQ ID NO:36 is a protein sequence of YP_884688.

SEQ ID NO:37 is a protein sequence of YP_884688.

SEQ ID NO:38 is a non-native enzyme Rubisco protein sequence.

SEQ ID NO:39 is a non-native enzyme Rubisco DNA sequence.

SEQ ID NO:40 is the hexamer protein sequence for synthetic operon of Example 6 from *Thermosynechococcus elongatus* BP-1: NC_004113.

SEQ ID NO:41 is the hexamer DNA sequence for synthetic operon of Example 6 from *Thermosynechococcus*

*elongatus* BP-1: NC_004113. This sequence has been codon-optimized for expression in *E. coli*.

SEQ ID NO:42 is the tandem domain protein sequence for synthetic operon of Example 6 from *Thermosynechococcus elongatus* BP-1: NC_004113.

SEQ ID NO:43 is the tandem domain DNA sequence for synthetic operon of Example 6 from *Thermosynechococcus elongatus* BP-1: NC_004113. This sequence has been codon-optimized for expression in *E. coli*.

SEQ ID NO:44 is the pentamer protein sequence for synthetic operon of Example 6 from *Thermosynechococcus elongatus* BP-1: NC_004113.

SEQ ID NO:45 is the pentamer DNA sequence for synthetic operon of Example 6 from *Thermosynechococcus elongatus* BP-1: NC_004113. This sequence has been codon-optimized for expression in *E. coli*.

SEQ ID NO:46 is the B1010 ribosome binding site used in the expression constructs in example 6.

SEQ ID NO:47 is the B1001 ribosome binding site used in the expression constructs in example 6.

SEQ ID NO:48 is the protein sequence of the SuperFolderGFP used in the SFGFP-CcmK2 fusion proteins.

SEQ ID NO:49 is the DNA sequence of the SuperFolderGFP. This sequence does not contain a stop codon.

SEQ ID NO:50 is the protein sequence for the *Haliangium ochraceum* targeting peptide found on the N-terminus of the aldolase gene encoded in the operon (Hoch_4427) with RDDLVRVIREELVRAL (SEQ ID NO: 51) corresponding to the predicted alpha helix/EP based on the criteria of Kinney et al., 2011. SEQ ID NO: 52 is the DNA sequence which encodes the targeting peptide optimized for *E. coli*.

SEQ ID NO:53 is the DNA sequence for the *Haliangium ochraceum* targeting peptide found on the N-terminus of the aldehyde dehydrogenase gene encoded in the operon (Hoch_4427) codon optimized for *E. coli*. SEQ ID NO: 54 is the targeting peptide sequence found on the N-terminus of the aldehyde dehydrogenase gene: ALREDRIAEIVERVLARL.

BRIEF DESCRIPTION OF THE DRAWINGS AND TABLES

FIG. 1A is diagram of synthetic operon construction. Shell proteins are placed under control of ribosomal binding sites (RBS) of varying translation start efficiency depending on their expected roles in BMC shell assembly. FIG. 1B shows three types of shell proteins that assemble to form icosahedral BMC shells. One polypeptide chain is indicated in color in example crystal structures for each type.

Figure 4:
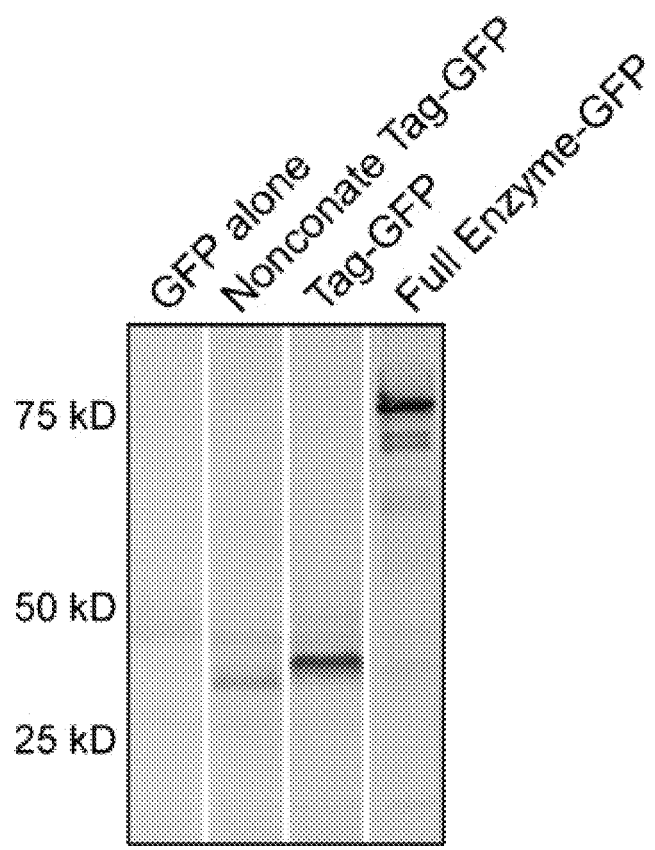

FIG. 4 shows a Western blot with anti-GFP antibody of microcompartment shells expressed with four types of constructs: GFP alone, GFP attached to an encapsulation tag from a different organism, GFP attached to a tag from *Haliangium ochraceum*, and GFP attached to the aldehyde dehydrogenase enzyme associated with the *Haliangium ochraceum* microcompartment. When encapsulation tags were included, GFP was detected in the microcompartment fraction.

Figure 5:
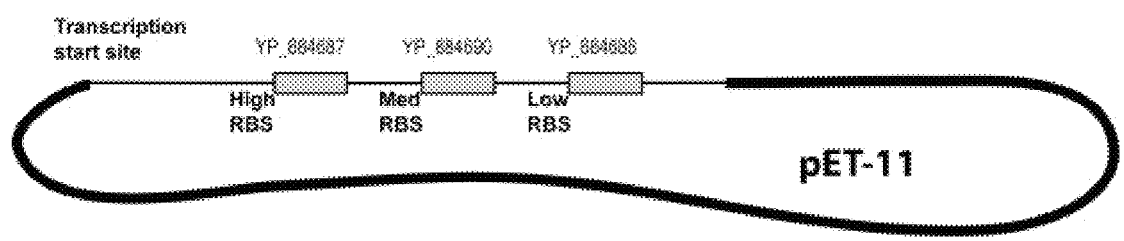

FIG. 5 illustrates the construction of a synthetic operon for expression of shell protein genes from *Mycobacterium smegmatis* in *E. coli* host cells.

Figure 6:
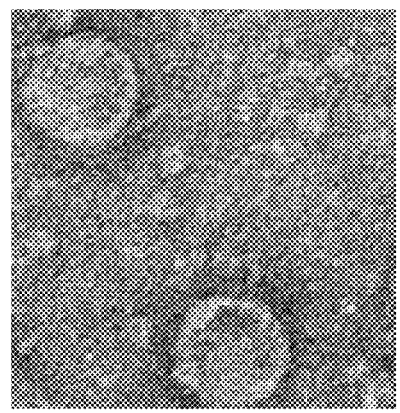

FIG. 6 shows negatively-stained electron microscope image of shells produced from expression of *M. smegmatis* shell proteins in *E. coli*.

Figure 7:
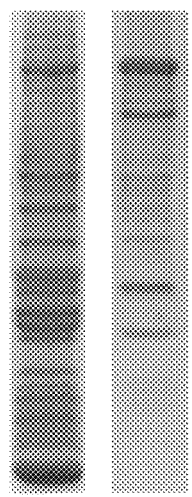

FIG. 7 shows the capture of the non-native enzyme Rubisco by the microcompartment shells produced by *H. ochraceum*. Left is SDS-PAGE gel. Right is a Western blot with anti-Rubisco.

Figure 8A:
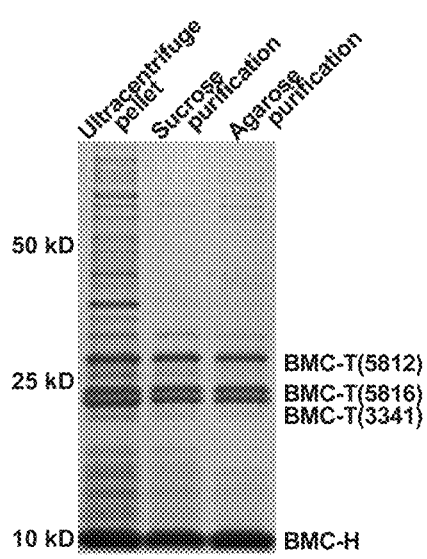
Figure 8B:

FIG. 8A shows the ultracentrifuge pull-down of shell proteins upon expression of *H. ochraceum* BMC shell protein construct in *E. coli*. The shell proteins copurified with sucrose gradient ultracentrifugation or agarose gel electrophoresis. Locus tags are indicated for proteins identified by mass spectrometry. FIG. 8B shows the synthetic operon for expression of the seven *H. ochraceum* shell proteins with locus tags indicated.

Figure 9A:
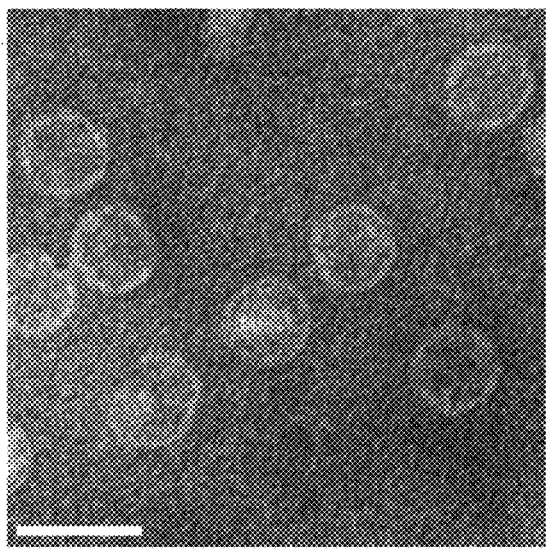
Figure 9B:
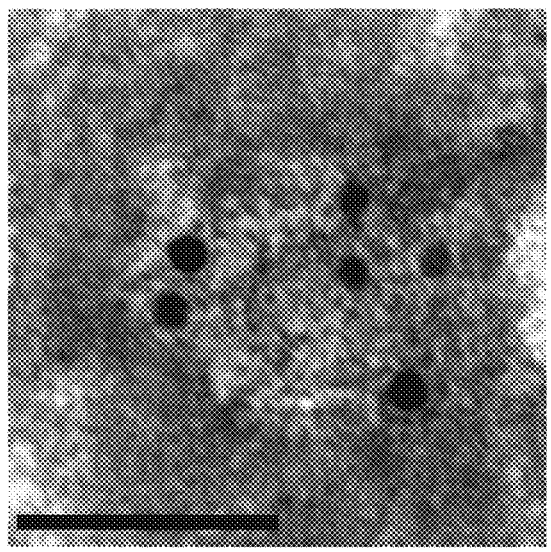
Figure 9C:
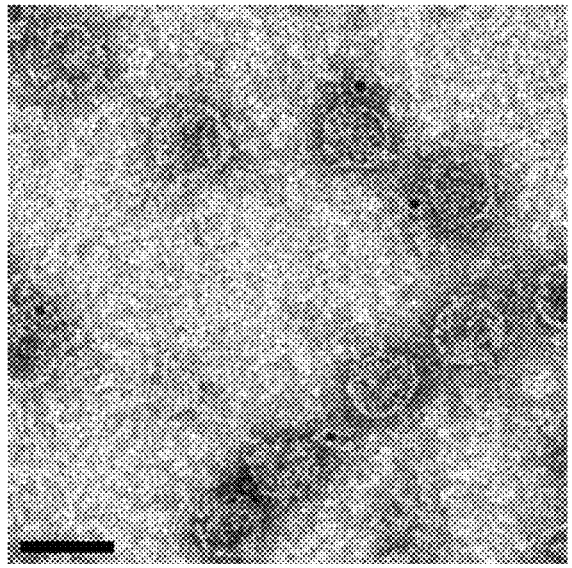
Figure 9D:
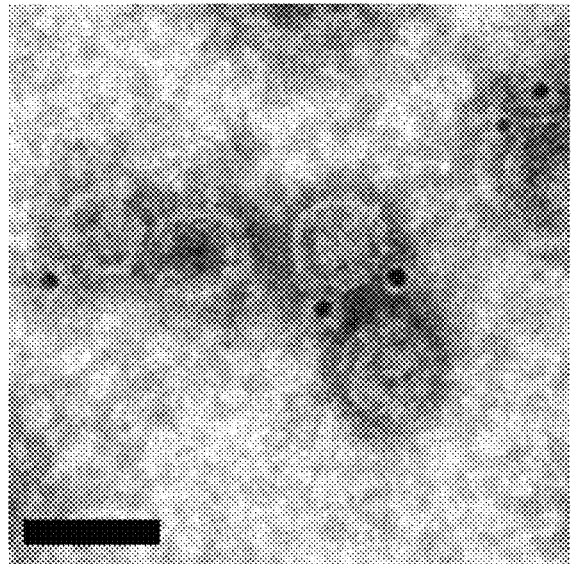

FIG. 9A shows a negatively stained electron microscopy image of *H. ochraceum* microcompartment shells purified from *E. coli*. White bar indicates 50 nm. FIGS. 9B-9D show negatively stained electron microscopy images of shells incubated with 5 nm gold particles conjugated to anti-rabbit and polyclonal antibodies raised against *H. ochraceum* BMC-T(5812). Black bar indicates 50 nm. The distances from shells to gold particles are consistent with the ~7 nm expected distance given the antibody dimensions.

Figure 10A:
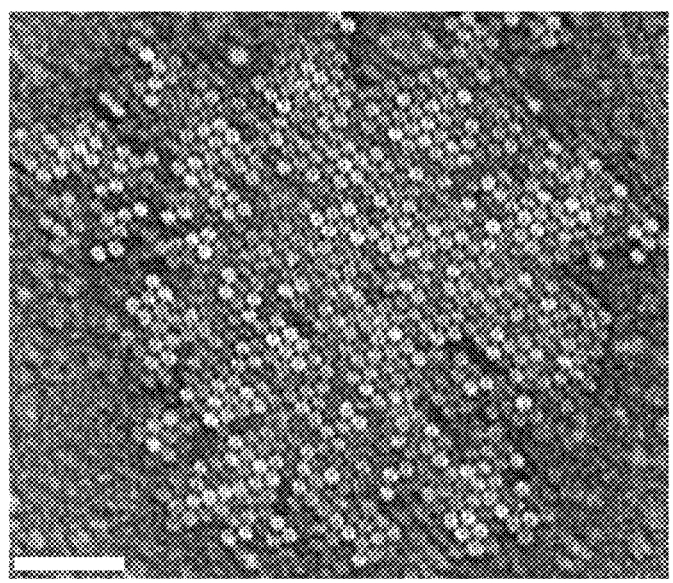
Figure 10B:
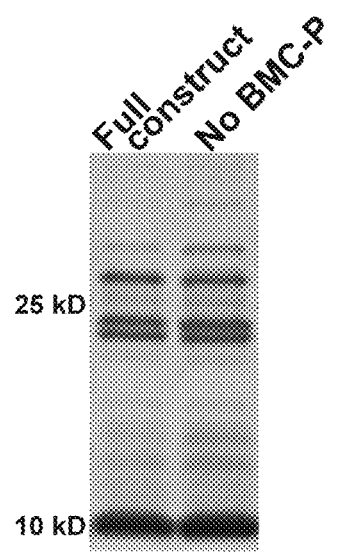
Figure 10C:
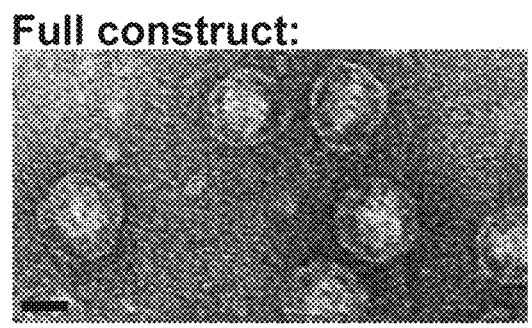
Figure 10C:
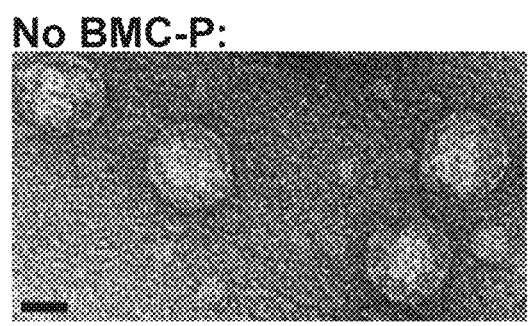
Figure 10D:
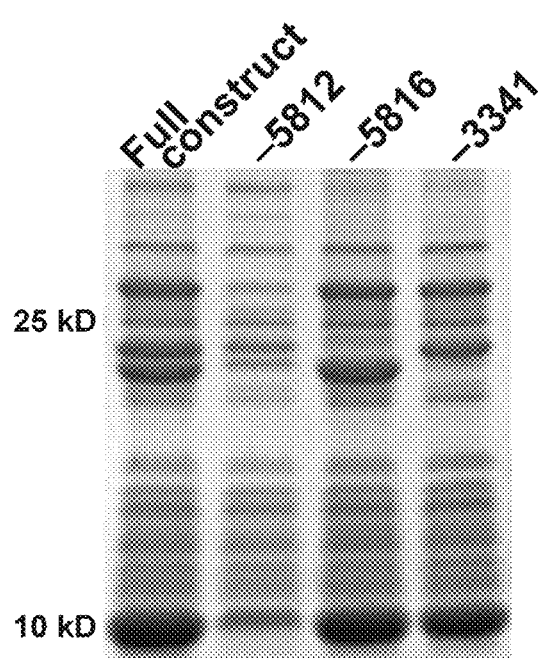

FIGS. 10A-10D show testing requirements for shell formation. FIG. 10A shows TEM images of pure BMC-H protein show two-dimensional assemblies of packed hexagons. The white bar indicates 50 nm. FIG. 10B shows SDS-PAGE of purified compartments formed upon shell protein expression with or without the BMC-P proteins. FIG. 10C shows TEM images of purified compartments formed upon expression with or without BMC-P. Black bars indicate 20 nm. FIG. 10D shows SDS-PAGE of ultracentrifuge extracts from cells expressing the full *H. ochraceum* construct and mutants. Stop codons were inserted early in each of the three BMC-T genes indicated, labeled by their locus tag numbers. Preparations were done in parallel and identical volumes of sample were loaded.

Figure 11A:
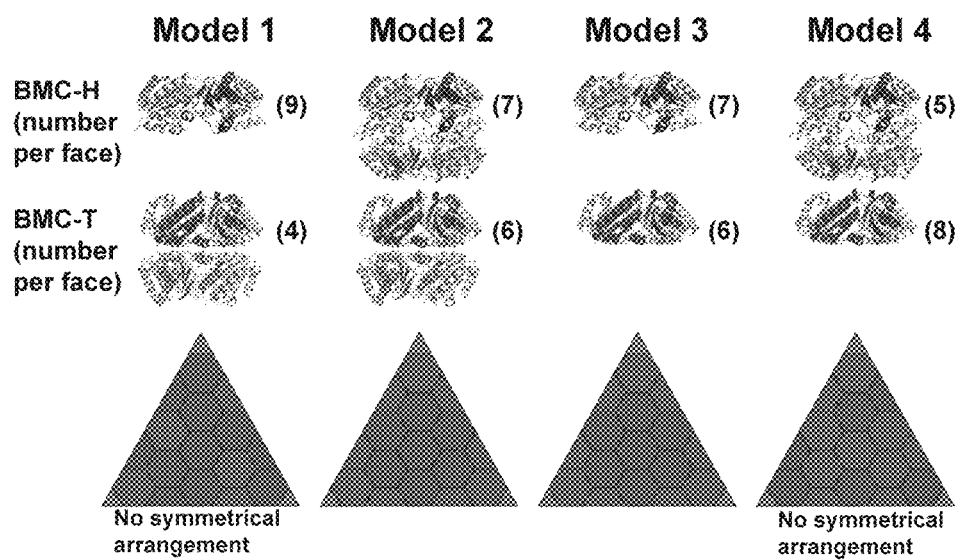
Figure 11B:
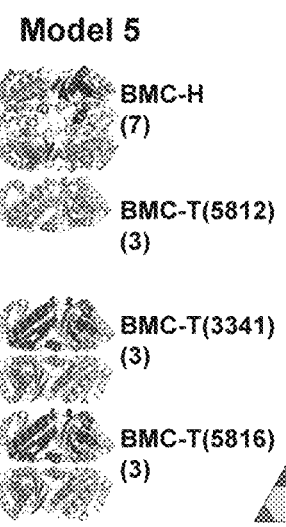
Figure 11C:
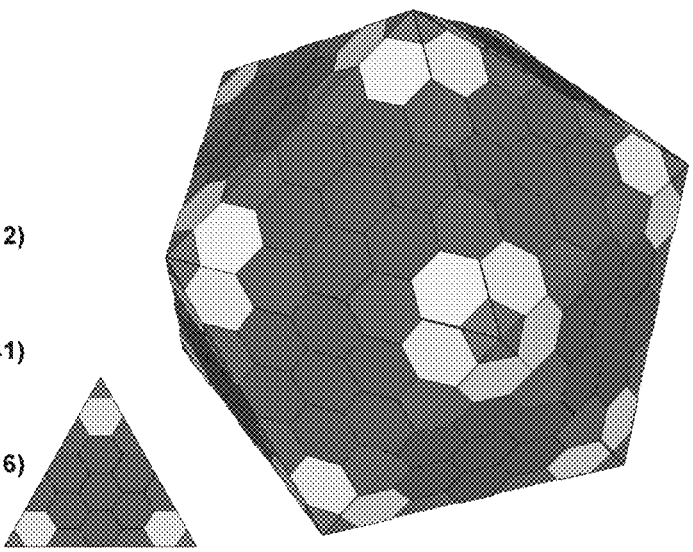

FIG. 11A shows models for shell protein stoichiometry. Four models are considered, with different stoichiometry of shell proteins in each hexagonal unit. In these models, all BMC-T units are treated identically. The number of each type of unit per icosahedral face is indicated in parentheses and possible layouts of the icosahedral face are shown. In FIG. 11B, Model 5 allows for different stoichiometries and structural roles for the different BMC-T units. The model is speculative, but supported by experimental data as described in the text. In FIG. 11C, the structural model for the icosahedron, with 13 hexagonal units per face, is well defined by the dimensions of the shells. The model is colored according to the structural roles suggested in Model 5, with BMC-H in blue, BMC-T in red and pink, and BMC-P in green, as in FIG. 1B.

Figure 12:
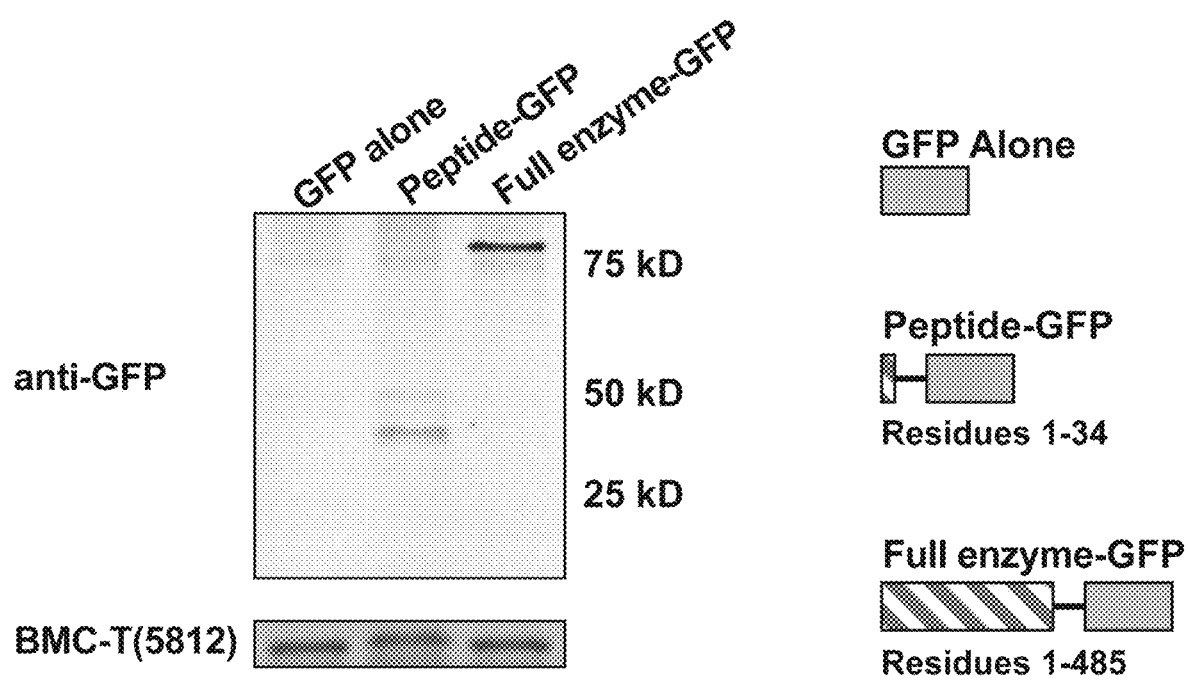

FIG. 12 shows Western blot with anti-GFP antibody of purified shell fractions following co-expression of shell proteins with three constructs. SDS-PAGE for the Hoch_5812 BMC-T unit is shown to indicate that equivalent quantities of shell protein were loaded.

FIG. 13A shows a TEM image of synthetic microcompartments (shells) composed of the proteins CcmO(BMC-T), CcmK2(BMC-H), CcmL(BMC-P), and a SFGFP(ns) CcmK2(BMC-H) fusion from *Thermosynechococcus elongatus* stained with 1% ammonium molybdate. 30,000× Mag. Scale bar=20 nm. FIG. 13B shows a TEM image of synthetic *Thermosynechococcus elongatus* CcmO(BMC-T)-CcmK2 (BMC-H)-CcmL(BMC-P)-SFGFP(ns)CcmK2 (BMC-H) shells stained with 1% uranyl acetate. 15,000× Mag.). Scale bar=50 nm. "ns" indicates no stop in reading frame between superfolder gfp and ccmk2 genes to produce a SFGFP-ccmK2(BMC-H) fusion protein. FIG. 13C shows a diagram of shell encoding synthetic operon construction. Shell proteins, identified by NCBI Accession numbers, are placed in control of ribosome binding sites (RBS) of various translation start efficiency, their relative strengths indicated as either Med (medium) or High, within a pET-23b expression vector. ADW83736_NP_681737 fusion identifies the SuperFolderGFP(SFGFP)-CcmK2(BMC-H) fusion protein. B1010 corresponds to ribosome binding site (SEQ ID NO:46) and B1010 corresponds to ribosome binding site (SEQ ID NO:47).

Figure 14A:
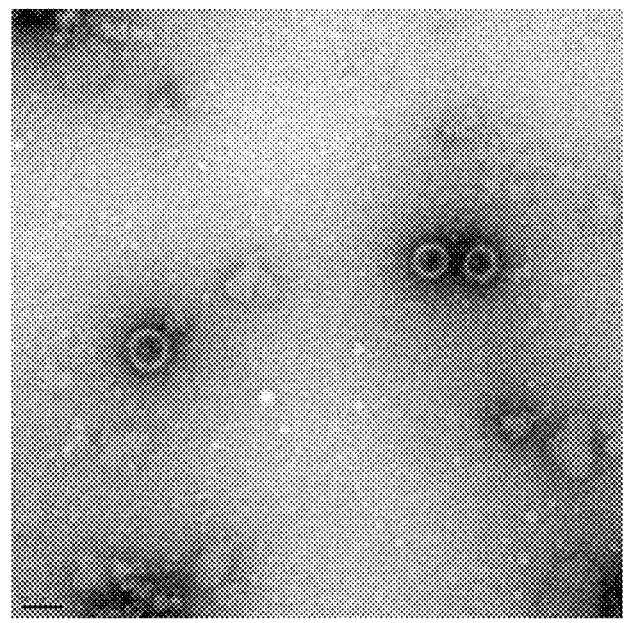
Figure 14B:
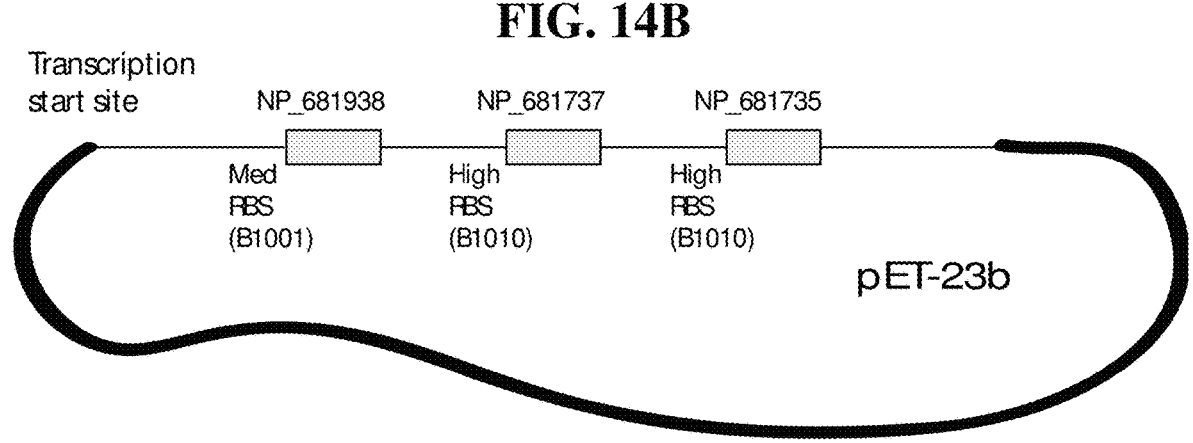

FIG. 14A shows a TEM image of synthetic shells composed of the proteins CcmO(BMC-T), CcmK2(BMC-H), and CcmL(BMC-P) from *Thermosynechococcus elongatus* stained with 1% uranyl acetate. 30,000× Mag. Scale bar=50 nm. FIG. 14B shows a diagram of shell encoding synthetic operon construction. Shell proteins, identified by NCBI Accession numbers, are placed in control of ribosome binding sites (RBS) of various translation start efficiency, their relative strengths indicated as either Med (medium) or High, within a pET-23b expression vector. B1010 corresponds to ribosome binding site (SEQ ID NO:46) and B1001 corresponds to ribosome binding site (SEQ ID NO:47).

Figure 15A:
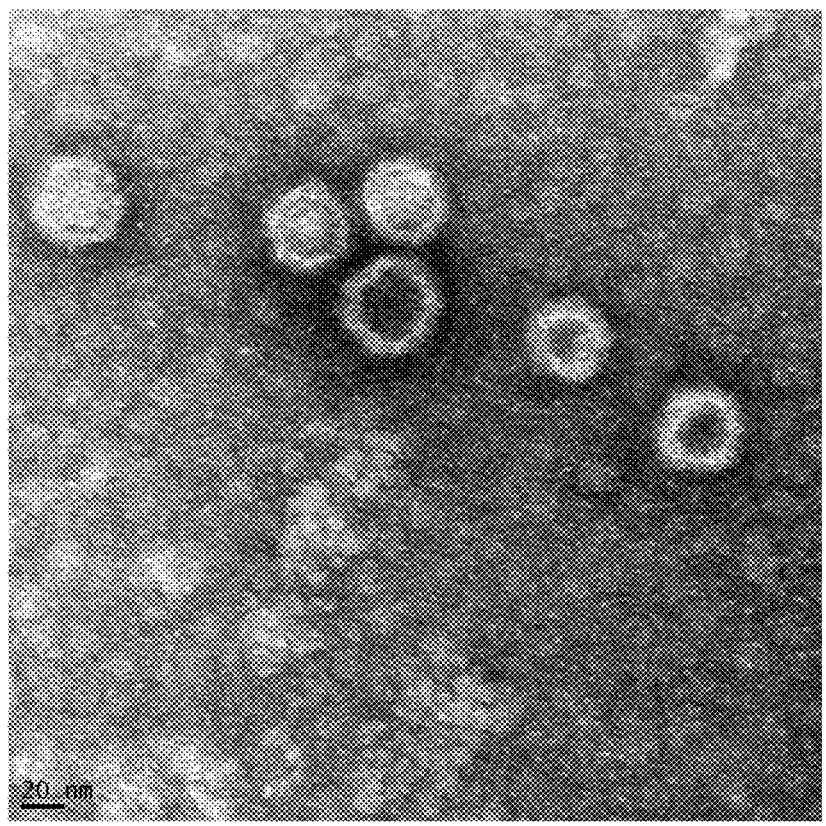
Figure 15B:
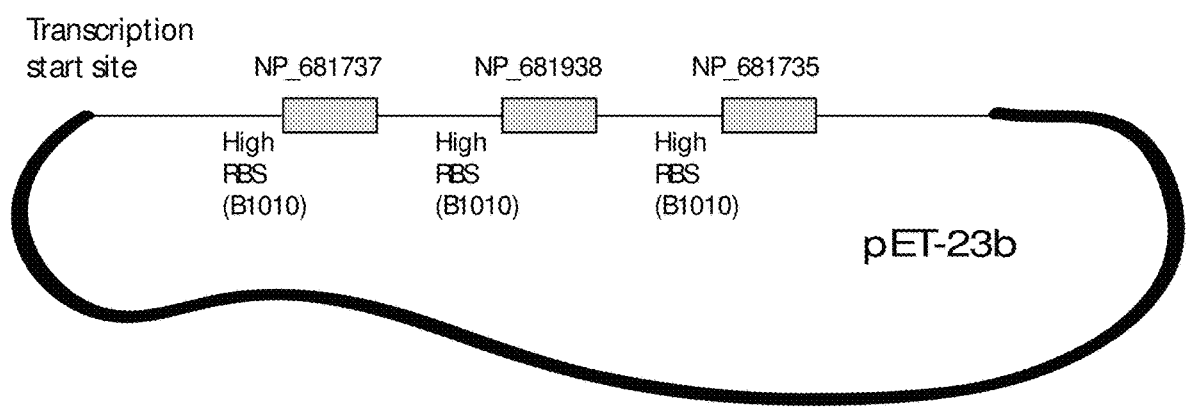

FIG. 15A shows TEM image of synthetic shells composed of the proteins CcmO(BMC-T), CcmK2(BMC-H), and CcmL(BMC-P) from *Thermosynechococcus elongatus* stained with 1% uranyl acetate. 18,500× Mag. Scale bar=100 nm. Shells shown were precipitated out of solution at an ammonium sulfate concentration of 5%. Not shown is an SDS-PAGE gel of ammonium sulfate precipitation purified shells. Percent ammonium sulfate in sample is indicated at the top of each lane. Bands likely corresponding CcmK2 (BMC-H), CcmO(BMC-T), CcmL(BMC-P) shell proteins and molecular weights are indicated. FIG. 15B shows a diagram of shell encoding synthetic operon construction. Shell proteins, identified by NCBI Accession numbers, are placed in control of various translation start efficiency within a pET-23b expression vector. B1010 corresponds to ribosome binding site (SEQ ID NO:46).

Figure 16A:
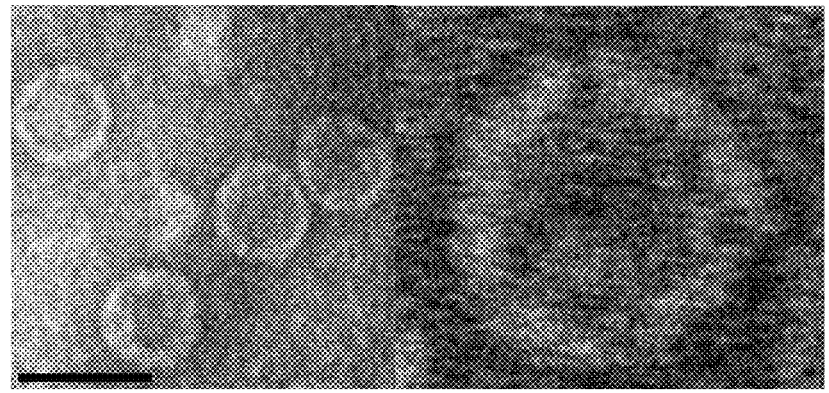
Figure 16B:
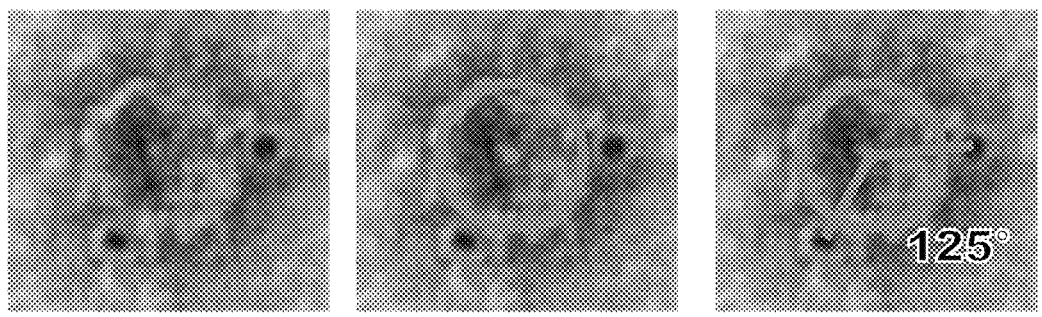
Figure 16C:
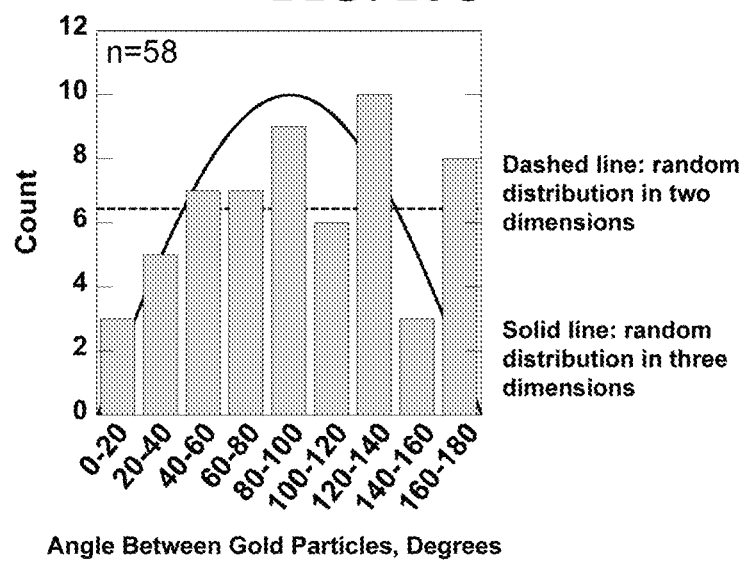

FIGS. 16A-16C show evidence of icosahedral construction. FIGS. 16A and 16B show TEM images of unlabeled shells showed thinning in some cases with angles consistent with icosahedral symmetry. In the graph in FIG. 16C, the observed distribution of angles, shown in the histogram bars, suggests a higher representation of 120°-140° and 160°-180° angles, as would be expected for vertices of icosahedral particles projected onto two dimensions. Examples of these angles that are expected to be more highly represented in icosahedral particles are shown in FIG. 16D.

FIGS. 17A and 17B have two graphs plotting the standard deviation/mean versus shell-protein stoichiometry. The data plotted in FIG. 17A are those calculated with simple ratios of shell units as given in Table 2. The graph in FIG. 17B shows the shell-protein stoichiometry in models 1-5 with BMC-P or with no BMC-P.

Figure 18:
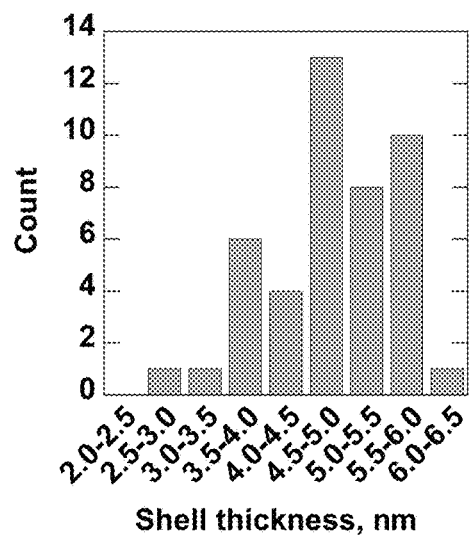

FIG. 18 is a graph showing the distribution of shell thickness in nm for 31 different shells. Measurements from 31 different shells were taken from TEM images collected on two different instruments and from two different shell preparations.

Figure 19A:
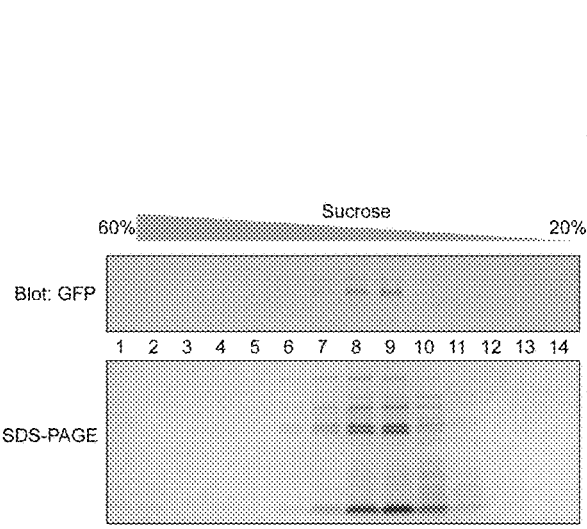
Figure 19B:
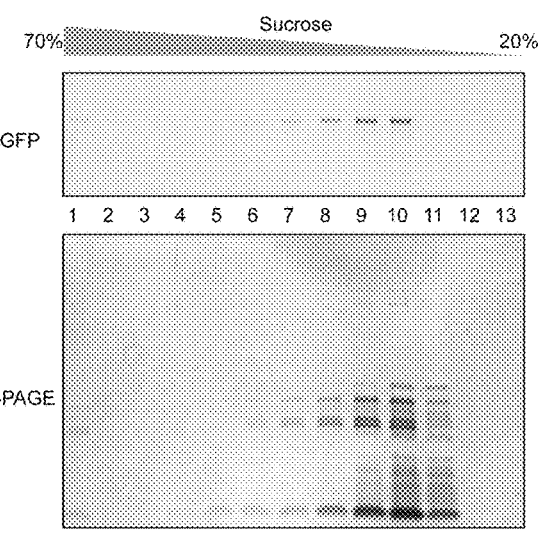

FIGS. 19A and 19B are two images of SDS-PAGE and western blotting of the fractions collected from the purification step for co-purification of GFP-labeled constructs with microcompartment shells. Following ultracentrifugation, the supernatants were separated with sucrose step gradients (20%-70% sucrose in TEMB buffer with 5% step sizes). BMC-containing fractions were pooled and concentrated by ultracentrifugation, then placed over a second sucrose gradient.

DETAILED DESCRIPTION OF THE PREFERRED EMBODIMENT

Introduction

Bacterial microcompartments (BMCs) are organelles composed of a protein coat and enzymes that may constitute a (partial) metabolic pathway or cycle, encapsulated by the protein. BMCs separate enzyme-catalyzed reactions from the rest of the cellular environment, allowing the concentration of intermediates in pathways or the sequestering of toxic species from the cellular environment or the enhancement of enzymatic function. Bacterial microcompartments (BMCs) encapsulate functionally related proteins. The bacterial microcompartment shell is composed of multiple paralogs of proteins. BMC shell proteins and the components they encapsulate are typically found in gene clusters (putative operons). The shells of BMCs are composed of multiple paralogs of proteins containing BMC domains pfam00936 and pfam03319. Three types of shell proteins have been identified: single pfam00936 domains ("hexamer"), fusion proteins composed of two pfam00936 domains ("tandem domain"), and single pfam03319 domains ("pentamer"). Hexamer and tandem domain proteins are the major components of known microcompartment shells, while pentamer proteins are presumed to be minor components.

In studying the structure and function of bacterial microcompartments including carboxysomes for $CO_2$ fixation, we sought a method to rapidly produce engineered microcompartments that could contain desired combinations of enzymes for diverse new synthetic functions. Herein we describe methods, compositions and systems for rapid production and purification of engineered enzyme microcompartments for new synthetic functions and for potential transfer of existing microcompartment functions (including $CO_2$ fixation machinery) to other organisms.

Many industries including those producing commercial chemicals, pharmaceuticals, and biofuels rely on natural and engineered biosynthetic pathways. Encapsulating and sequestering some of these enzymatic steps in BMCs offers the potential to increase the flux through specific steps in metabolic pathways (as in natural $CO_2$ fixation pathways) or to prevent cellular toxicity of specific steps in metabolic pathways (as in the processing of aldehyde intermediates in the breakdown of alcohol feedstocks by bacteria). The ability to design and construct new BMCs allows the possibility of achieving these benefits in new natural and engineered biosynthetic pathways. Further, a streamlined synthetic process for construction of BMCs may allow incorporation of, for example, carboxysome-based carbon fixation into new organisms, including plants of interest for biofuels, potentially increasing biomass production in these new host organisms. In addition, engineered microcompartments could be deployed extracellularly, for example to introduce catalytic modules into the environment or for use in precipitation of minerals.

Bacterial microcompartments (BMCs) sequester functionally linked enzymes and metabolic pathways from the cytoplasmic environment by encapsulation inside a selectively permeable protein shell. To develop a system that would allow engineering of new metabolic microcompartments, we screened diverse sets of natural BMC shell proteins, many from organelles of unknown function, for production of BMC shells. From this screen, the seven BMC shell proteins of the halophilic myxobacterium *Haliangium ochraceum* were found to produce remarkably homogeneous shells in high yield when expressed from a designed synthetic operon in *E. coli*. These shells were smaller and more uniform than any previously described BMCs, with measured diameters of 39±2 nm. The size and nearly uniform geometry allowed the construction of a precise icosahedral model. This structural model was combined with measurements of stoichiometry, protein structural data, and gold-labeling electron microscopy data to produce a detailed model for shell composition that suggests distinct roles for the seven shell proteins. Further, we found that new proteins could be targeted for encapsulation into the shells by fusion to a predicted targeting peptide sequence. The defined composition and tractability of this system will enable both fundamental studies of the effects of metabolic pathway compartmentalization and the design of new synthetic BMCs. By refactoring shell protein genes from diverse BMC types known only bioinformatically into a synthetic operon, we have introduced a general strategy for the design and construction of novel protein-based synthetic encapsulating structures, carboxysome shells and organelles.

Herein is described a general strategy for production of microcompartment shells in a heterologous host environment. Host species such as *E. coli, B. subtilis*, or *S. cerevisiae* are more amenable to laboratory experiments and industrial-scale production than are many prokaryotic organisms that produce BMCs. In particular, many microcompartment containing—containing organisms are difficult to manipulate genetically and pose difficulties in the production and purification of microcompartments. We developed a general strategy for production of microcompartments in heterologous host environments to allow microcompartments including carboxysomes to be produced in bacterial strains that are suitable for genetic manipulation and industrial-scale production, such as *E. coli*.

Definitions

An "expression vector" or "expression cassette" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

By "host cell" is meant a cell that contains an expression vector and supports the replication or expression of the expression vector. Host cells may be prokaryotic cells including but not limited to, *E. coli*, cyanobacteria including but not limited to, *Synechococcus elongatus*, or eukaryotic cells including but not limited to, yeast, insect, amphibian, or mammalian cells such as CHO, HeLa and the like, e.g., cultured cells, explants, and cells in vivo.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Amino acid polymers may comprise entirely L-amino acids, entirely D-amino acids, or a mixture of L and D amino acids. The use of the term "peptide or peptidomimetic" in the current application merely emphasizes that peptides comprising naturally occurring amino acids as well as modified amino acids are contemplated.

"Pfam00936 domains" and "Pfam03319 domains" as used herein refer to proteins that are recognized as members of the protein families of those names in the pfam database (Website pfam.sanger.ac.uk). A "hexamer(s)" as used herein is a protein that contains a single pfam00936 domain. A "tandem domains" as used herein is a protein that contains two pfam00936 domains. A "pentamer" as used herein is a protein that contains a pfam03319 domain.

Any "gene" is meant to refer to the polynucleotide sequence that encodes a protein, i.e., after transcription and translation of the gene a protein is expressed. As understood in the art, there are naturally occurring polymorphisms for many gene sequences. Genes that are naturally occurring allelic variations for the purposes of this invention are those genes encoded by the same genetic locus. Thus, any "bacterial microcompartment gene", "microcompartment gene" as referred to herein is meant to include any polynucleotide that encodes a Pfam00936 domain or Pfam03319 domain protein or variants thereof.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel.

The terms "identical" or percent "identity," in the context of two or more polypeptide sequences (or two or more nucleic acids), refer to two or more sequences or subsequences that are the same or have a specified percentage of amino acid residues or nucleotides that are the same e.g., 60% identity, preferably 65%, 70%, 75%, 80%, 85%, 90%, 91%, 92%, 93%, 94%, 95%, 96%, 97%, 98%, 99% or 100% identity over a specified region (such as the first 15 amino acids of SEQ ID NOS:20-22), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are typically used.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, polypeptide-nucleic acids (PNAs). Unless otherwise indicated, a particular nucleic acid sequence also encompasses "conservatively modified variants" thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., *J. Biol. Chem.*, 260:2605-2608 (1985); Rossolini et al., *Mol. Cell. Probes*, 8:91-98 (1994)). The term nucleic acid can be used interchangeably with gene, cDNA, mRNA, oligonucleotide, and polynucleotide.

A "label" or "detectable label" is a composition detectable by spectroscopic, photochemical, biochemical, immunochemical, or chemical means. For example, useful labels include radioisotopes (e.g., $^3$H, $^{35}$S, $^{32}$P, $^{51}$Cr, or $^{125}$I), fluorescent dyes, electron-dense reagents, enzymes (e.g., alkaline phosphatase, horseradish peroxidase, or others commonly used in an ELISA), biotin, digoxigenin, or haptens and proteins for which antisera or monoclonal antibodies are available (e.g., proteins such as SEQ ID NOS: 23, 25, or 27 can be made detectable, e.g., by incorporating a radiolabel into the protein, and used to detect antibodies specifically reactive with the protein).

DESCRIPTIONS OF THE EMBODIMENTS

In one embodiment, a bacterial microcompartment (BMC) and metabolic pathway is selected to be synthesized and/or engineered in a host cell. A polynucleotide encoding the bacterial compartment and enzymes in the metabolic pathway can be inserted into a host organism and if needed, expressed using an inducible expression system. When referring to the bacterial compartments or microcompartments, it is meant to include any number of proteins, shell proteins or enzymes (e.g., dehydrogenases, aldolases, lyases, etc.) that comprise or are encapsulated in the compartment.

Naturally existing BMC operons may contain a few or several of these three types of shell proteins. Prior strategies to produce microcompartment shells in heterologus hosts have transformed the host system with the natural operon sequences of the original organism. However, in a natural organism, the required shell proteins may not be placed together on the chromosome, they may be intermixed with enzymes or other proteins, and the ordering and regulatory mechanisms may not be useful in a new host organism.

The present approach does not rely on the natural operon sequences. Instead individual BMC components are identified according to their domain types and their roles in the BMC shell construction and their expression levels are adjusted according to these roles by incorporating host-specific ribosomal binding sites in the expression cassette or operon construction (See FIG. 1A). Thus, herein is described an experimentally validated strategy and methods to produce a range of naturally occurring microcompartment shells in *E. coli* and other host organisms.

In one embodiment, polynucleotides encoding bacterial microcompartment shell proteins, are cloned into an appropriate plasmid, inserted into an expression vector, and used to transform cells from any host organism. Suitable host organisms include, but are not limited to, bacteria such as *E. coli, B. subtilis, S. cerevisiae*, cyanobacteria such as *S. elongatus*, plants such as *Nicotiana tabacum* and *Camelina sativa*, algae, fungi, or other eukaryotic organisms.

In one embodiment, the polynucleotides are in an inducible expression system which maintains the expression of the inserted genes silent unless an inducer molecule (e.g., IPTG) is added to the medium containing the host cell. The expression vector or construct may be a vector for coexpression or in some embodiments, it may be a neutral site vector for insertion into a host genome such as *Synechococcous elongatus*. The construct may include either inducible transcription elements or may be constitutively expressed in the host organism Bacterial colonies are allowed to grow after gene expression has begun, or if required, after induction of gene expression. Thus, in some embodiments, expression vectors comprising a promoter operably linked to a heterologous nucleotide sequence or a fragment thereof, that encodes a microcompartment RNA or proteins are further provided. The expression vectors of the invention find use in generating transformed plants, plant cells, microorganisms, algae, fungi, and other eukaryotic organisms as is known in the art and described herein. The expression vector will include 5' and 3' regulatory sequences operably linked to a polynucleotide of the invention. "Operably linked" is intended to mean a functional linkage between two or more elements. For example, an operable linkage between a polynucleotide of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame. The vector may additionally contain at least one additional gene to be co-transformed into the organism. Alternatively, the additional gene(s) can be provided on multiple expression vectors or cassettes. Such an expression vector is provided with a plurality of restriction sites and/or recombination sites for insertion of the polynucleotide that encodes a microcompartment RNA or polypeptide to be under the transcriptional regulation of the regulatory regions. The expression vector may additionally contain selectable marker genes.

The expression vector will include in the 5'-3' direction of transcription, a transcriptional initiation region (i.e., a promoter), a cluster of bacterial compartment genes each preceded by a translational initiation site (RBS) specific to the organism and type of shell protein and followed by a translation termination signal (stop codon), and, optionally, a transcriptional termination region functional in the host organism. The regulatory regions (i.e., promoters, transcriptional regulatory regions, ribosomal binding sites and translational termination regions) and/or any targeting sequences may be native or analogous to those found in the host cell or to each other. Alternatively, the regulatory regions and/or the targeting regions may be heterologous to the host cell or to each other. As used herein, "heterologous" in reference to a sequence that originates from a foreign species, or, if from the same species, is modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

In various embodiments, an expression vector further comprising a ribosomal binding site sequence that is specific for the host cell, wherein the ribosomal binding site sequence is placed in the vector adjacent and precedent to a bacterial compartment gene so as to control the translation efficiency of the gene it precedes.

Ribosomal binding sites (RBS) are sequences that precede the coding region of a gene whereby the RBS allows the ribosome to bind the transcript and initiate translation. Ribosomal binding site sequences have been found in various organisms and control and are used herein to vary translation start efficiency in organisms. For example in *E. coli*, having the sequence of TTTAGAGAAAGAG-GAGAAATACTAG (SEQ ID NO:1) is a high ribosomal binding site (RBS) sequence which means that any gene directly following this sequence (i.e., directly 3'- to this sequence) will be translated at a higher rate. This is turn provides for more or greater expression levels of the protein encoded by the gene which follows a high RBS sequence. Likewise other sequences are known to promote a medium or low translation efficiency in *E. coli*, such as TTTAGAGATTAAAGAGGAGAAATACTAG (SEQ ID NO:2, medium RBS) and TTTAGAGTCACACAG-GAAACCTACTAG (SEQ ID NO:3, low RBS).

Figure 1A:
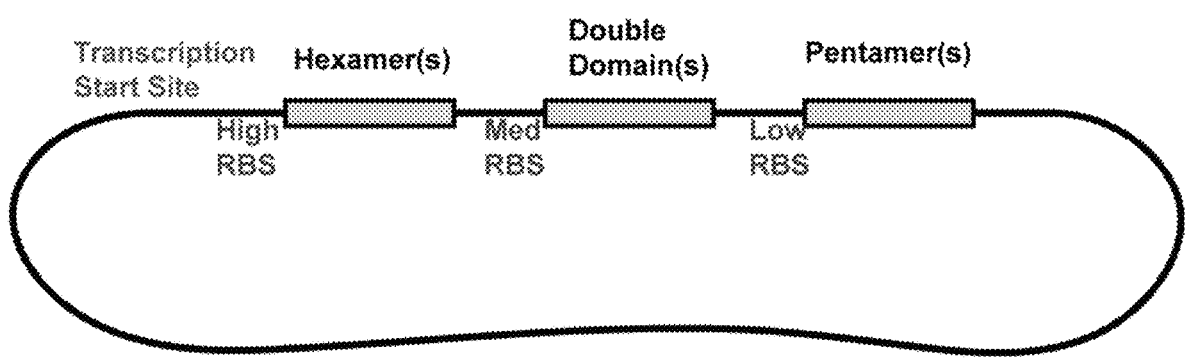
Figure 1B:
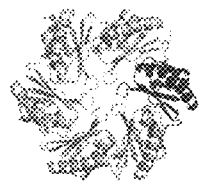
Figure 1B:
Figure 1B:
Figure 1B:
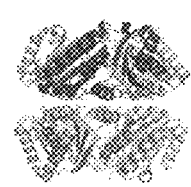
Figure 1B:
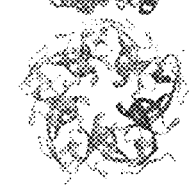
Figure 1B:

Therefore, in various embodiments, to produce a BMC shell in a new host organism, a synthetic operon is constructed that contains the desired shell proteins. For each individual protein, an RBS is selected depending on the type. For example, hexamers (BMC-H) are given an RBS with the highest level of translation initiation. Tandem domains are given an RBS at a reduced level of translation initiation (for example, 60% of the predicted value for hexamers). Pentamers are given an RBS with the lowest level of translation initiation (for example, 5% of the predicted value for hexamers. Thus, in some embodiments, the expression vector might further comprise high, medium and/or low ribosomal binding site sequences for a host organism that are inserted in the vector adjacent to and preceding various bacterial compartment genes in the cluster. FIGS. 1A and 1B show an example of such a construct where a high RBS sequence precedes the hexamer protein encoding genes, the tandem domain genes are preceded by a medium RBS, and the pentamer genes are preceded by a low RBS sequence. This resulted in high, medium and low expression levels of these proteins after induction.

RBS sequences may be obtained from various sources. They may be designed, for example, by using a calculation to predict translation initiation rates (e.g., Salis, H. M. (2011) The Ribosome Binding Site Calculator, *Methods in Enzymology* 498: 19-42). RBS sequences may be selected from DNA sequences of natural organisms (e.g. the natural RBS site from the *H. neapolitanus* shell protein CsoS1C, GATTTTGAATGAGTCTTTATTGAGGAGAGAAGAA (SEQ ID NO:4)). RBS sequences may also be used from databases of biological sequences, including the Registry of Standard Biological Parts.

The selected microcompartment genes are placed onto the construct using the following general strategy. Single pfam00936 domains and their RBS sequences ("hexamers") are placed first in the synthetic operon, followed by tandem pfam00936 ("tandem domains") and their RBS sequences, and finally followed by pfam03319 ("pentamer") domains and their RBS sequences. Therefore, in various embodiments, an expression vector comprising a transcription start site sequence, one or more nucleic acid sequences for bacterial compartment genes and with ribosomal binding site sequences that are specific for the host cell, wherein the ribosomal binding site sequence is placed in the vector adjacent and directly 5'- to a bacterial compartment gene.

Figure 2:
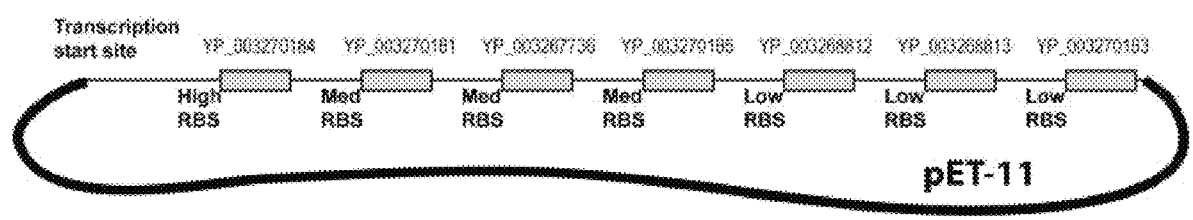
FIG. 2 is a diagram of the construct used to express *H. ochraceum* shell proteins in *E. coli*. Above each gene are listed the protein accession numbers for the protein sequences encoded by the genes.

In various embodiments, the synthetic operon contains all the microcompartment genes and their RBS sequences as shown in FIGS. 1A, 1B, and 2.

In other embodiments, microcompartment genes can be incorporated into multiple expression vectors and/or under multiple promoter control. For example, the specific microcompartment genes encoding *H. ochraceum* shell proteins could be assembled with one or more expression vectors using one or more different transcription initiation points. The shell proteins need not be placed on a single operon. For example, hexamers could be placed under control of one promoter, tandem domains could be placed under the control of another promoter, and pentamers could be placed under the control of a third promoter. Furthermore, the high RBS sequence and the hexamer gene may be present on one synthetic operon, while the tandem domain genes and its RBS sequence are present on a second synthetic operon and the pentamer gene and its low RBS sequence are presented on a third synthetic operon, or any combination thereof.

Where appropriate, the polynucleotides may be optimized for increased expression in the transformed organism. For example, the polynucleotides can be synthesized using preferred codons for improved expression.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression vector can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). The above list of selectable marker genes is not meant to be limiting. Any selectable marker gene can be used in the present invention.

In another embodiment, it may be beneficial to express the gene from an inducible promoter. The gene product may also be co-expressed with a targeting polypeptide or fragment thereof, such that the polypeptide is in the C-terminal or N-terminal region of any other gene in the construct.

In various embodiments, microcompartment shells may be produced from another organism in a bacterial host cell, such as *E. coli*, by construction of a synthetic operon as described herein. For example, in one embodiment, the microcompartment shells produced are cyanobacterial carboxysome shell proteins produced in *E. coli*.

However, in other embodiments, microcompartment shells may be produced in another non-bacterial host organism by construction of a synthetic operon and adjusting the RBS sequences to that host organism. For example, *Haliangium ochraceum* shells or other types of shells may be produced in cyanobacteria or plants, such as might be done to incorporate Rubsico and carbonic anhydrase to produce a synthetic carboxysome in plants.

In one embodiment, an in-vitro transcription/translation system (e.g., Roche RTS 100 *E. coli* HY) can be used to produce cell-free microcompartments or expression products.

In some embodiments, it is preferred that the microcompartments expressed in the non-native host organism should provide the host organism enhanced enzymatic activity, enhanced biomass production and $CO_2$ sequestration abilities, or produce valuable intermediates (Acetyl CoA), or sequester and protect oxygen-sensitive enzymes (engineered or native) or encapsulate reactions that would otherwise be toxic to the cell but however, be non-toxic or have low toxicity levels to humans, animals and plants or other organisms that are not the target.

In some embodiments, the microcompartment proteins are preferably incorporated into the genome of the host microorganism or eukaryote (plant, algae, yeast/fungi) to provide new or enhanced metabolic activity. In some embodiments, the microcompartment proteins are incorporated to provide enhanced carbon fixation and sequestration activity in the plant or organism (i.e., addition of a carboxysome) or produce valuable intermediates (Acetyl CoA), or sequester and protect oxygen-sensitive enzymes (engineered or native) or encapsulate reactions that would otherwise be toxic to the cell.

Genes which encode the enzymes or proteins to carry out these enhanced reactions or activities and which will be encapsulated by the microcompartment may be targeted to the microcompartment by adding encapsulation tags specific for the microcompartment shell. Methods and compositions describing this in greater detail are described previously by some of the inventors in U.S. application Ser. No. 13/367,260 filed on Feb. 6, 2012, published as US-2002/02104590-A1 ("Design and Implementation of Novel and/or Enhanced Bacterial Microcompartments for Customizing Metabolism"), and also described in Lassila, J. K., Bernstein, S. L., Axen S. D., Kinney J. N. and Kerfeld, C. A. Assembly of Robust Bacterial Microcompartment Shells using Building Blocks from an Organelle of Unknown Function. *Journal of Molecular Biology* in press, both of which are hereby incorporated by reference in their entirety. Such encapsulation tags and the genes encoding the proteins to be encapsulated may be incorporated in the microcompartment expression vector itself or by co-expression of such encapsulation tagged genes which are on a second vector added to the host cell.

In one embodiment, a polynucleotide sequence encoding a targeting peptide or a fragment thereof as described can be inserted into the polynucleotide that encodes a protein of interest in the N-terminus or C-terminus or between functional domains of the proteins, thereby permitting the encapsulation of that protein into the BMC upon expression. Example 3 provides a description of co-expression of encapsulation tagged genes to express proteins which are encapsulated in the microcompartments which are produced in the *E. coli* host cell. A DNA sequence (SEQ ID NO:24) encoding a polypeptide derived from the N-terminus of aldehyde dehdyrogenase from *H. ochraceum* was incorporated into an expression construct at the 5' end of a sequence encoding green fluorescent protein (GFP) for expression in *H. ochraceum*, which resulted in green fluorescent protein being encapsulated into the shells.

(SEQ ID NO: 24)
ATGGCACTGCGTGAAGATCGTATCGCTGAAATCGTGGAACGTGTCCTG

GCCCGTCTGGATGGCAACTCGGGCTCGTCGGCTGCACCGCATAGCGG

CTCTGGTGCGGGTAGCGGTTCGGGTTCGGGCTCTGGTTCTGGTAGTGG

CAGTGGTAGTGGTTCGGGCTCCGGATCC

In other embodiments, proteins may be incorporated into shells without using encapsulation tags by overexpressing proteins of interest, by electrostatic or hydrophobic or other types of protein-protein interactions that allow association of proteins with microcompartment shell protein, or by fusing proteins to other proteins that associate with shells. For example, an enzyme of interest could be fused to a Rubisco that interacts directly with a shell protein or an enzyme of interest could be directly fused to a shell protein.

In another embodiment, using an encapsulation tag or other approach as listed above, a mechanism is provided for targeting biological molecules that would benefit from being compartmentalized and/or recombining them with other molecules and biological molecules within a bacterial microcompartment shell. This will enable the engineering of new or enhanced bacterial microcompartments. An example strategy is in one embodiment, a carboxysome shell protein is co-expressed with a fluorescent protein-peptide fusion. These protein-peptide fusions can be transferred among organisms (e.g. bacteria, fungi, plants, algae) using basic molecular techniques, followed by directed evolution to optimize phenotype. Alternatively, the modules are stable in solution or can be engineered to be (e.g., via reversible bonds/crosslinks), stable in solution, thus carrying out catalysis in cell free, non-biological systems.

In another embodiment, this allows one to engineer new metabolic modules (essentially organelles of specific function) into a host organism such as bacteria or a plant and provides a new approach to designing and optimizing catalysis in solution. For example, insertion of polynucleotides encoding for the expression of the peptides provided for in SEQ ID NOS: 23 and 27 or for example, at least the localization peptide regions in the polypeptides of SEQ ID NOS: 23 and 27 into the synthetic construct or expression cassette, allows the incorporation or encapsulation of the expression products SEQ ID NOS: 23 and 27 into the microcompartment shell This strategy allows a fully synthetic and modular approach to design of new microcompartments or for production of existing microcompartments in new host organisms. An additional benefit of this construction method is that it will allow engineering of new pore selectivities by making amino acid substitutions at the perimeter of the pores. The ability to alter the pore selectivities is a crucial step toward being able to develop microcompartments as reaction chambers for any desired new metabolic pathway.

In another embodiment, proteins or other molecules may be introduced into synthetic microcompartments in vitro by dissociating the microcompartment shells in the presence of molecules to be encapsulated and then altering conditions so that the shells re-assemble, thereby trapping the cargo to be encapsulated.

In other embodiments, the constructs for expressing microcompartments described herein may be used for delivery of proteins, biomolecules, drugs or other agents in another organism. In other embodiments, the present constructs and methods may be used to synthetically produce, in bacteria for example, large quantities of the microcompartments encapsulating or incorporating the proteins, biomolecules, drugs or other agents, which after extraction are delivered to another organism needing treatment.

In some embodiments, the synthetic microcompartment described herein comprising shell proteins from *H. ochraceum* could be used for a broad range of applications in biotechnology in addition to those described above, including as a scaffold for engineered vaccine constructs, as a vehicle for delivery of protein or small molecule drug agents, or as a capsule for stabilizing biocatalyst systems.

In another embodiment, the synthetic microcompartments described herein comprising shell proteins from *H. ochraceum* or *T. elongatus* may be used to produce a synthetic carboxysome by incorporation of rubisco and carbonic anhydrase, and by engineering the pores for selective permeability for carbon fixation activity. For example, the expression construct described in Example 5 may be designed to also incorporate the genes for the *H. ochraceum* enzymes rubisco and carbonic anhydrase, and the genes for selectively permeable pores, with these genes under the correct RBS sequence control. This expression construct could then be inserted into an organism such as bacteria, yeast or a plant such as Tobacco or Camelina.

Example 1: Design and Construction of a Synthetic Operon for Expression in *E. coli*

We have proposed and experimentally validated a strategy to produce a range of naturally occurring microcompartment shells in *E. coli* and other host organisms. Prior strategies to produce microcompartment shells in heterologous hosts have transformed the host system with the natural operon sequences of the original organism. Our approach does not rely on the natural operon sequences. Individual BMC components are identified according to their domain types and their roles in the BMC shell construction and their expression levels are adjusted according to these roles (FIGS. 1A and 1B).

We surveyed a diverse set of natural BMC gene clusters, many of unknown function, to identify new shell building blocks. The cohort of shell proteins encoded in the genome of the halophilic myxobacterium *Haliangium ochraceum*[32] stood out as an unusual combination of different shell protein types, unlike any other BMC gene cluster. It is atypical in that it is enriched in BMC-T and BMC-P genes relative to BMC-H, which typically occur in multiple copies in BMC gene clusters. Moreover two of the BMC-T genes are part of the small family of BMC-T proteins predicted to form double-stacked dimers of trimers.

Seven BMC gene products were identified from *Haliangium ochraceum* SMP-2, DSM 14365. DNA sequences were selected to encode the protein sequences while utilizing high-frequency codons from *E. coli*, the host organism. Thus, the DNA sequences are not those of the native organism, *H. ochraceum*, even though the protein sequences are the same.

A synthetic construct containing the seven *H. ochraceum* BMC shell proteins expressed in *E. coli* resulted in the production of robust shells in high yield. The homogeneity and small size of these shells enabled us to propose a model for shell construction that suggests possible roles for the individual shell proteins. New proteins were targeted to these shells by fusion to peptide encapsulation tags, opening up the possibility of future design of new synthetic microcompartments or three-dimensional scaffolds. The tractability of this system should enable fundamental structural and mechanistic investigations of BMC function.

```
YP_003270184 Protein
                                        (Hexamer; SEQ ID NO: 6)
MADALGMIEVRGFVGMVEAADAMVKAAKVELIGYEKTGGGYVTAVVRGDVAAVKAATEAGQRAA

ERVGEVVAVHVIPRPHVNVDAALPLGRTPGMDKSA

YP_003270184 Gene
                                          (BMC-H; SEQ ID NO: 7)
ATGGCGGACGCACTGGGTATGATTGAAGTTCGTGGTTTTGTTGGTATGGTGGAAGCGGCGGATG

CTATGGTGAAAGCGGCTAAAGTTGAACTGATTGGTTATGAAAAAACCGGCGGTGGCTACGTGAC

GGCAGTGGTTCGTGGTGATGTCGCAGCAGTTAAGGCAGCTACCGAAGCCGGTCAGCGTGCAGCA

GAACGTGTTGGTGAAGTCGTGGCAGTTCATGTCATCCCGCGTCCGCACGTGAACGTTGATGCAG

CTCTGCCGCTGGGTCGTACGCCGGGTATGGACAAAAGCGCGTAA

YP_003270181 Protein
                                          (BMC-T; SEQ ID NO: 8)
MDHAPERFDATPPAGEPDRPALGVLELTSIARGITVADAALKRAPSLLLMSRPVSSGKHLLMMR

GQVAEVEESMIAAREIAGAGSGALLDELELPYAHEQLWRFLDAPVVADAWEEDTESVIIVETAT

VCAAIDSADAALKTAPVVLRDMRLAIGIAGKAFFTLTGELADVEAAAEVVRERCGARLLELACI

ARPVDELRGRLFF
```

YP_003270181 Gene (BMC-T; SEQ ID NO: 9)
ATGGACCACGCTCCGGAACGCTTTGATGCGACCCCGCCGGCAGGTGAACCGGACCGCCCGGCAC

TGGGTGTGCTGGAACTGACCTCAATTGCTCGTGGTATCACCGTTGCGGATGCGGCCCTGAAACG

TGCACCGAGTCTGCTGCTGATGTCCCGCCCGGTCAGCTCTGGCAAGCATCTGCTGATGATGCGT

GGCCAGGTGGCAGAAGTTGAAGAATCAATGATTGCAGCTCGCGAAATCGCTGGTGCAGGTTCGG

GTGCTCTGCTGGATGAACTGGAACTGCCGTATGCGCACGAACAACTGTGGCGCTTTCTGGACGC

ACCGGTGGTTGCAGATGCATGGGAAGAAGACACCGAAAGCGTCATTATCGTGGAAACCGCGACG

GTGTGCGCGGCCATTGATAGTGCCGACGCAGCTCTGAAAACGGCACCGGTCGTGCTGCGTGATA

TGCGCCTGGCCATTGGTATCGCTGGCAAGGCGTTTTTCACCCTGACGGGTGAACTGGCAGACGT

GGAAGCGGCCGCAGAAGTTGTCCGTGAACGTTGCGGTGCACGTCTGCTGGAACTGGCATGTATC

GCACGCCCGGTTGATGAACTGCGTGGCCGCCTGTTTTTCTAA

YP_003267736 Protein (BMC-T; SEQ ID NO: 10)
MELRAYTVLDALQPQLVAFLQTVSTGFMPMEQQASVLVEIAPGIAVNQLTDAALKATRCQPGLQ

IVERAYGLIEMHDDDQGQVRAAGDAMLAHLGAREADRLAPRVVSSQIITGIDGHQSQLINRMRH

GDMIQAGQTLYILEVHPAGYAALAANEAEKAAPIKLLEVVTFGAFGRLWLGGGEAEIAEAARAA

EGALAGLSGRDNRG

YP_003267736 Gene (BMC-T; SEQ ID NO: 11)
ATGGAACTGCGTGCTTATACGGTCCTGGATGCCCTGCAGCCGCAACTGGTCGCCTTTCTGCAAA

CGGTGTCAACGGGTTTCATGCCGATGGAACAGCAAGCGAGCGTTCTGGTCGAAATTGCACCGGG

TATCGCTGTCAACCAGCTGACCGACGCAGCACTGAAAGCAACGCGTTGCCAGCCGGGTCTGCAA

ATTGTGGAACGTGCGTATGGCCTGATCGAAATGCATGATGACGATCAGGGTCAAGTTCGTGCAG

CTGGTGACGCAATGCTGGCACACCTGGGTGCACGTGAAGCTGATCGTCTGGCACCGCGTGTGGT

TAGCTCTCAGATTATCACCGGTATTGACGGCCATCAGAGTCAACTGATCAACCGTATGCGCCAC

GGTGATATGATTCAGGCAGGCAAACGCTGTATATCCTGGAAGTTCATCCGGCAGGTTACGCAG

CACTGGCAGCTAATGAAGCCGAAAAAGCGGCCCCGATTAAGCTGCTGGAAGTCGTGACCTTTGG

TGCATTCGGTCGTCTGTGGCTGGGTGGTGGTGAAGCAGAAATCGCAGAAGCAGCTCGTGCGGCA

GAAGGTGCACTGGCTGGTCTGTCCGGCCGTGATAATCGCGGCTAA

YP_003270185 Protein (BMC-T; SEQ ID NO: 12)
MSITLRTYIFLDALQPQLATFIGKTARGFLPVPGQASLWVEIAPGIAINRVTDAALKATKVQPA

VQVVERAYGLLEVHHFDQGEVLAAGSTILDKLEVREEGRLKPQVMTHQIIRAVEAYQTQIINRN

SQGMMILPGESLFILETQPAGYAVLAANEAEKAANVHLVNVTPYGAFGRLYLAGSEAEIDAAAE

AAEAAIRSVSGVAQESFRDR

YP_003270185 Gene (BMC-T; SEQ ID NO: 13)
ATGTCAATCACCCTGCGCACCTATATCTTTCTGGACGCCCTGCAACCGCAACTGGCAACCTTCA

TCGGCAAAACGGCTCGTGGCTTCCTGCCGGTCCCGGGTCAGGCAAGCCTGTGGGTGGAAATTGC

TCCGGGTATTGCGATCAACCGTGTGACCGATGCGGCCCTGAAAGCTACGAAGGTGCAGCCGGCG

GTTCAAGTGGTTGAACGCGCGTATGGCCTGCTGGAAGTTCATCACTTCGATCAGGGCGAAGTCC

TGGCAGCTGGTAGTACCATCCTGGACAAACTGGAAGTTCGTGAAGAAGGTCGCCTGAAGCCGCA

GGTGATGACCCATCAAATTATCCGTGCTGTTGAAGCGTATCAGACGCAAATTATCAACCGCAAT

AGTCAGGGCATGATGATTCTGCCGGGTGAATCCCTGTTTATCCTGGAAACCCAACCGGCAGGTT

ACGCAGTCCTGGCAGCCAATGAAGCCGAAAAAGCAGCTAACGTTCACCTGGTCAATGTGACGCC

GTATGGCGCATTCGGTCGTCTGTACCTGGCCGGCTCAGAAGCAGAAATTGATGCGGCCGCAGAA

GCTGCGGAAGCCGCAATCCGCAGCGTTTCTGGTGTCGCGCAGGAATCGTTTCGTGACCGCTAA

YP_003268812 Protein
 (BMC-P; SEQ ID NO: 14)
MYLGRVIGTVVAERKVAGLEGAKLLLVQPLDDALSPVGGVQAAVDTVQAGPDDLVYLVGSREAA

LALTPSFVPVDAAIVGIVDDVHAPERAS

YP_003268812 Gene
 (BMC-P; SEQ ID NO: 15)
ATGTATCTGGGTCGTGTGATTGGTACCGTGGTGGCTGAACGCAAAGTGGCGGGTCTGGAAGGCG

CAAAACTGCTGCTGGTGCAACCGCTGGATGACGCACTGAGTCCGGTCGGTGGTGTGCAGGCAGC

AGTTGATACCGTCCAAGCAGGTCCGGATGACCTGGTGTATCTGGTTGGTAGCCGTGAAGCAGCT

CTGGCGCTGACGCCGTCTTTTGTGCCGGTTGATGCGGCCATTGTCGGCATCGTTGATGACGTGC

ATGCACCGGAACGCGCTAGCTAA

YP_003268813 Protein
 (BMC-P; SEQ ID NO: 16)
MRLCRVLGSVVATVKHPVYNGLPLMIVQPLDDAGRDAGASFLAVDNVQSGPGDRVLVLTEGGGV

RQILALGDQVPIRSLIVGVVDAVDGVAATGVDDAGGAADSAAAAKSVRADELPADASAAGRGE

YP_003268813 Gene
 (BMC-P; SEQ ID NO: 17)
ATGCGTCTGTGTCGTGTTCTGGGCTCCGTCGTCGCCACCGTCAAGCACCCGGTCTACAATGG

TCTGCCGCTGATGATCGTTCAACCGCTGGATGACGCAGGTCGTGATGCAGGCGCTAGTTTTCTG

GCTGTTGATAACGTCCAGTCCGGTCCGGGTGACCGTGTCCTGGTGCTGACCGAAGGTGGTGGTG

TGCGTCAGATTCTGGCACTGGGTGATCAAGTCCCGATTCGCAGCCTGATCGTGGGCGTGGTTGA

TGCAGTGGACGGTGTTGCAGCAACGGGTGTTGATGACGCAGGTGGTGCAGCTGATAGCGCAGCA

GCAGCTAAATCTGTCCGTGCAGATGAACTGCCGGCAGACGCAAGCGCGGCCGGTCGCGGCGAAT

AA

YP_003270183 Protein
 (BMC-P; SEQ ID NO: 18)
MVLGKVVGTVVASRKEPRIEGLSLLLVRACDPDGTPTGGAVVCADAVGAGVGEVVLYASGSSAR

QTEVTNNRPVDATIMAIVDLVEMGGDVRFRKD

YP_003270183 Gene
 (Pentamer; SEQ ID NO: 19)
ATGGTCCTGGGTAAAGTCGTGGGTACGGTGGTGGCGAGCCGCAAAGAACCGCGCATTGAAGGTC

TGAGCCTGCTGCTGGTCCGTGCCTGCGATCCGGACGGTACCCCGACGGGTGGTGCAGTGGTTTG

TGCAGATGCAGTGGGTGCAGGTGTTGGTGAAGTCGTGCTGTATGCGAGTGGCAGCTCTGCCCGT

CAGACCGAAGTCACGAACAATCGCCCGGTTGATGCAACCATTATGGCTATCGTTGACCTGGTCG

AAATGGGCGGTGATGTGCGTTTTCGCAAAGACTAA

Synthetic operons were produced with these protein sequences. The protein sequences were preceded by ribosomal binding sites with high, medium, and low levels of predicted translation initiation in *E. coli*. In one example, the RBS sequences immediately 5'- to the gene listed were:

For Hexamer (BMC-H):
(SEQ ID NO: 20)
TCTAGAAATAATTTTGTTTAGAGAAAGAGGAGAAATACTAG

For Tandem domain (BMC-T):
(SEQ ID NO: 21)
TTTAGAGATTAAAGAGGAGAAATACTAG

For Pentamer (BMC-P):
(SEQ ID NO: 22)
TTTAGAGTCACACAGGAAACCTACTAG

These sequences were inserted into the pET-11 expression vector as shown in FIG. 2.

A synthetic operon was constructed as described. Ribosomal binding site sequences from the Community RBS Collection of the Registry of Standard Biological Parts were used as follows:

For BMC-H:
(SEQ ID NO: 55)
TCTAGAGAAAGAGGAGAAATACTAGATG

For BMC-T:
(SEQ ID NO: 56)
TCTAGAGATTAAAGAGGAGAAATACTAGATG

For BMC-P:
(SEQ ID NO: 57)
TCTAGAGTCACACAGGAAACCTACTAGATG

The full sequence of the synthetic *H. ochraceum* operon was as follows and identified as SEQ ID NO:58 with the highlighted regions being the BMC hexamer, tandem domain or pentamer sequences:

```
AATAATTTTGTTTAGAGAAAGAGGAGAAATACTAG
ATGGCGGACGCACTGGGTATGATTGAAGTTCGTGGTTTTGTTGGTATGGTGGAAGCGGCGGATGCTATGG
TGAAAGCGGCTAAAGTTGAACTGATTGGTTATGAAAAAACCGGCGGTGGCTACGTGACGGCAGTGGTTCG
TGGTGATGTCGCAGCAGTTAAGGCAGCTACCGAAGCCGGTCAGCGTGCAGCAGAACGTGTTGGTGAAGTC
GTGGCAGTTCATGTCATCCCGCGTCCGCACGTGAACGTTGATGCAGCTCTGCCGCTGGGTCGTACGCCGG
GTATGGACAAAAGCGCGTAA
TTTAGAGATTAAAGAGGAGAAATACTAG
ATGGACCACGCTCCGGAACGCTTTGATGCGACCCCGCCGGCAGGTGAACCGGACCGCCCGGCACTGGGTG
TGCTGGAACTGACCCTCAATTGCTCGTGGTATCACCGTTGCGGATGCGGCCCTGAAACGTGCACCGAGTCT
GCTGCTGATGTCCCGCCCGGTCAGCTCTGGCAAGCATCTGCTGATGATGCGTGGCCAGGTGGCAGAAGTT
GAAGAATCAATGATTCGAGCTCGCGAAATCGCTGGTGCAGGTTCGGGTGCTCTGCTGGATGAACTGGAAC
TGCCGTATGCGCACGAACAACTGTGGCGCTTTCTGGACGCACCGGTGGTTGCAGATGCATGGGAAGAAGA
CACCGAAAGCGTCATTATCGTGGAAACCGCGACGGTGTGCGCGGCCATTGATAGTGCCGACGCAGCTCTG
AAAACGGCACCGGTCGTGCTGCGTGATATGCGCCTGGCCATTGGTATCGCTGGCAAGGCGTTTTTCACCC
TGACGGGTGAACTGGCAGACGTGGAAGCGGCCCGCAGAAGTTGTCCGTGAACGTTGCGGTGCACGTCTGCT
GGAACTGGCATGTATCGCACGCCCGGTTGATGAACTGCGTGGCCGCCTGTTTTTCTAA
TTTAGAGATTAAAGAGGAGAAATACTAG
ATGGAACTGCGTGCTTATACGGTCCTGGATGCCCTGCAGCCGCAACTGGTCGCCTTTCTGCAAACGGTGT
CAACGGGTTTCATGCCGATGGAACAGCAAGCGAGCGTTCTGGTCGAAATTGCACCGGGTATCGCTGTCAA
CCAGCTGACCGACGCAGCACTGAAAGCAACGCGTTGCCAGCCGGGTCTGCAAATTGTGGAACGTGCGTAT
GGCCTGATCGAAATGCATGATCACGATCAGGGTCAAGTTCGTGCAGCTGGTGACGCAATGCTGGCACACC
TGGGTGCACGTGAAGCTGATCGTCTGGCACCGCGTGTGGTTAGCTCTCAGATTATCACCGGTATTGACGG
CCATCAGAGTCAACTGATCAACCGTATGCGCCACGGTGATATGATTCAGGCAGGCCAAACGCTGTATATC
```

-continued

```
CTGGAAGTTCATCCGGCAGGTTACGCAGCACTGGCAGCTAATGAAGCCGAAAAAGCGGCCCCGATTAAGC

TGCTGGAAGTCGTGACCTTTGGTGCATTCGGTCGTCTGTGGCTGGGTGGTGGTGAAGCAGAAATCGCAGA

AGCAGCTCGTGCGGCAGAAGGTGCACTGGCTGGTCTGTCCGGCCGTGATAATCGCGGCTAA
```

TTTAGAGATTAAAGAGGAGAAATACTAG

```
ATGTCAATCACCCTGCGCACCTATATCTTTCTGGACGCCCTGCAACCGCAACTGGCAACCTTCATCGGCA

AAACGGCTCGTGGCTTCCTGCCGGTCCCGGGTCAGGCAAGCCTGTGGGTGGAAATTGCTCCGGGTATTGC

GATCAACCGTGTGACCGATGCGGCCCTGAAAGCTACGAAGGTGCAGCCGGCGGTTCAAGTGGTTGAACGC

GCGTATGGCCTGCTGGAAGTTCATCACTTCGATCAGGGCGAAGTCCTGGCAGCTGGTAGTACCATCCTGG

ACAAACTGGAAGTTCGTGAAGAAGGTCGCCTGAAGCCGCAGGTGATGACCCATCAAATTATCCGTGCTGT

TGAAGCGTATCAGACGCAAATTATCAACCGCAATAGTCAGGGCATGATGATTCTGCCGGGTGAATCCCTG

TTTATCCTGGAAACCCAACCGGCAGGTTACGCAGTCCTGGCAGCCAATGAAGCCGAAAAAGCAGCTAACG

TTCACCTGGTCAATGTGACGCCGTATGGCGCATTCGGTCGTCTGTACCTGGCCGGCTCAGAAGCAGAAAT

TGATGCGGCCGCAGAAGCTGCGGAAGCCGCAATCCGCAGCGTTTCTGGTGTCGCGCAGGAATCGTTTCGT

GACCGCTAA
```

TTTAGAGTCACACAGGAAACCTACTAG

```
ATGTATCTGGGTCGTGTGATTGGTACCGTGGTGGCTGAACGCAAAGTGGCGGGTCTGGAAGGCGCAAAAC

TGCTGCTGGTGCAACCGCTGGATGACGCACTGAGTCCGGTCGGTGGTGTGCAGGCAGCAGTTGATACCGT

CCAAGCAGGTCCGGATGACCTGGTGTATCTGGTTGGTAGCCGTGAAGCAGCTCTGGCGCTGACGCCGTCT

TTTGTGCCGGTTGATGCGGCCATTGTCGGCATCGTTGATGACGTGCATGCACCGGAACGCGCTAGCTAA
```

TTTAGAGTCACACAGGAAACCTACTAG

```
ATGCGTCTGTGTCGTGTTCTGGGCTCCGTCGTCGCCACCGTCAAGCACCCGGTCTACAATGGTCTGCCGC

TGATGATCGTTCAACCGCTGGATGACGCAGGTCGTGATGCAGGCGCTAGTTTTCTGGCTGTTGATAACGT

CCAGTCCGGTCCGGGTGACCGTGTCCTGGTGCTGACCGAAGGTGGTGGTGTGCGTCAGATTCTGGCACTG

GGTGATCAAGTCCCGATTCGCAGCCTGATCGTGGGCGTGGTTGATGCAGTGGACGGTGTTGCAGCAACGG

GTGTTGATGACGCAGGTGGTGCAGCTGATAGCGCAGCAGCAGCTAAATCTGTCCGTGCAGATGAACTGCC

GGCAGACGCAAGCGCGGCCGGTCGCGGCGAATAA
```

TTTAGAGTCACACAGGAAACCTACTAG

```
ATGGTCCTGGGTAAAGTCGTGGGTACGGTGGTGGCGAGCCGCAAAGAACCGCGCATTGAAGGTCTGAGCC

TGCTGCTGGTCCGTGCCTGCGATCCGGACGGTACCCCGACGGGTGGTGCAGTGGTTTGTGCAGATGCAGT

GGGTGCAGGTGTTGGTGAAGTCGTGCTGTATGCGAGTGGCAGCTCTGCCCGTCAGACCGAAGTCACGAAC

AATCGCCCGGTTGATGCAACCATTATGGCTATCGTTGACCTGGTCGAAATGGGCGGTGATGTGCGTTTTC

GCAAAGACTAA
```

Example 2: Expressing and Producing Microcompartment Shells in *E. coli*

The construct was expressed from an IPTG-inducible pET-11 vector in *E. coli* BL21(DE3) RIL cells. Expression was induced with 0.4 mM IPTG. The cells were lysed with BPER detergent (Pierce) and centrifuged at low speed (12,000×g). The supernatant was then centrifuged at high speed (60,000×g) to separate assembled microcompartments from soluble proteins. The microcompartments were purified further using density gradient centrifugation. FIGS.

3A-3C show negatively-stained electron microscopy images of purified microcompartments.

Figure 3A:
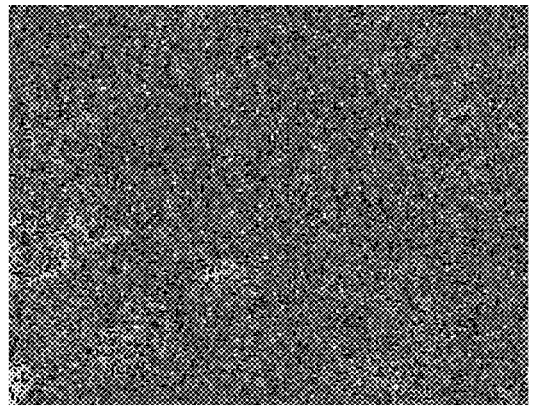
FIGS. 3A-3C are electron microscopy images of microcompartment shells isolated from *E. coli* cell extract.
Figure 3B:
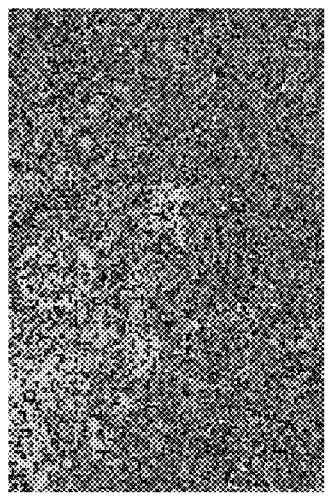
Figure 3C:
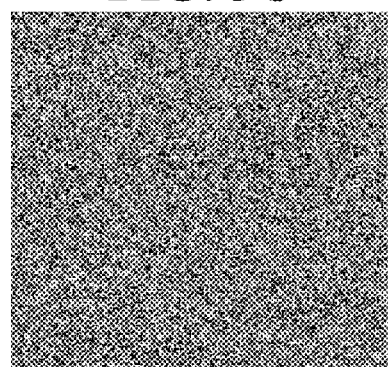

The purified shells were analyzed by SDS-PAGE, trypsin digest, and mass spectrometry and found to be composed of the shell proteins from *Haliangium ochraceum* as designed. Purified shells were incubated on Formvar-coated grids (Electron Microscopy Sciences), negatively stained using ammonium molybdate, and imaged using a Tecnai 12 TEM instrument. FIGS. 3A-3C show electron microscopy images of microcompartment shells isolated from *E. coli* cell extract.

Example 3: Using Encapsulation Tags to Incorporate Proteins into Microcompartment Shells The synthetic operon described above in Example 2 was coexpressed with a second vector, an IPTG-inducible pCOLA-DUET-1 vector, encoding either green fluorescent protein (GFP) with no tag or GFP linked to a tag or full enzyme construct. Microcompartment fractions were isolated as described above.

Three types of constructs were tested and were pulled down with the microcompartment shells as shown in FIG. 4.

1. Tag-GFP construct (this uses the Tag sequence that was previously predicted for this organism; the tag is shown in bold). The following protein sequence was fused to the N-terminus of GFP:

(SEQ ID NO: 23)
MALREDRIAEIVERVLARLDGNSGSSAAPHSGSGAGSGSGSGSGSGSG

SGSGS.

The DNA sequence used was:

(SEQ ID NO: 24)
ATGGCACTGCGTGAAGATCGTATCGCTGAAATCGTGGAACGTGTCCTGGC

CCGTCTGGATGGCAACTCGGGCTCGTCGGCTGCACCGCATAGCGGCTCTG

GTGCGGGTAGCGGTTCGGGTTCGGGCTCTGGTTCTGGTAGTGGCAGTGGT

AGTGGTTCGGGCTCC.

The sequence of the previously predicted tag is underlined. Additional amino acids were used to extend the linker between the peptide and the GFP because reduced GFP fluorescence was observed without an extended linker. The previously predicted tag was identified as Aldehyde dehydrogenase Nterm (HochDRAFT_00990) with the Accession Number ZP_03875711. The updated Protein Accession Number is YP_003270182 and Locus tag: Hoch_5813.

2. Full Enzyme-GFP construct (the whole enzyme from which the tag was predicted was fused to GFP): The protein sequence is from an aldehyde dehydrogenase—the same as listed above in #1: Protein accession number YP_003270182; Locus tag: Hoch_5813. The following protein sequence was fused to the N-terminus of GFP with the sequence of the previously predicted tag shown in bold:

(SEQ ID NO: 25)
MALREDRIAEIVERVLARLDGNSGSSAAPHSGSGAPAATAGGASLDIPRG

TLGVYADADAAVNAARRGFAANEALPLRTRQAMIDAMRKVARAHIPELAR

YAVAETGLGRYEDKLAKNELVIAKTPGPEILAPVAYTGDDGLTLTERAPY

GVIGAITPCTNPTETVICNAIGMLSGGNAVVFNVHPSAARVCNWLVHLLN

EAIMSVGGPRDAITSVESPTIDSAQTLMTHAGVRLVVVTGGPGVVRAAMK

SGKKVIAAGPGNPPAVVDETANLAKAAAAIIKGASIDNNIICTAEKEIVA

VASIADELSRLLGQRGALVLGDAQVRALERVVLDGEHVNKEWVGKDASRI

AEQIGLRGHGSDLRLLVCPVDEGHPFVQHELLMPVIGLVRVSDATEAMAT

AVRVEHGFCHTAVMHSTHIDRLSAMARVCNASIFVKNDCNLAGLGLGGEG

FTSFTIASPTGEGLTTARDFTRVRRCTLKESFRFVGSGSGSGSGSGSGSG

SGSGS

The DNA sequence used to encode the above fused protein was the following sequence and identified as SEQ ID NO: 26:

ATGGCTCTGCGTGAAGATCGTATCGCTGAAATCGTGGAACGTGTCCTGGC

CCGTCTGGATGGTAACTCCGGCTCGTCGGCTGCCCCGCACAGCGGCTCTG

GTGCGCCGGCGGCCACCGCTGGCGGTGCGAGCCTGGATATTCCGCGTGGC

ACGCTGGGTGTGTATGCAGATGCTGACGCAGCTGTTAACGCAGCACGTCG

CGGTTTTGCAGCTAATGAAGCCCTGCCGCTGCGTACCCGTCAGGCAATGA

TTGATGCAATGCGTAAAGTTGCGCGCGCCCATATCCCGGAACTGGCACGT

TATGCAGTGGCTGAAACCGGCCTGGGTCGCTACGAAGATAAACTGGCTAA

GAACGAACTGGTTATTGCGAAGACGCCGGGCCCGGAAATCCTGGCACCGG

TGGCATATACGGGCGATGACGGTCTGACCCTGACGGAACGCGCCCCGTAC

GGCGTTATTGGTGCAATCACCCCGTGCACGAACCCGACCGAAACGGTGAT

TTGTAATGCCATCGGTATGCTGTCAGGCGGTAACGCAGTGGTTTTCAATG

TGCATCCGTCGGCGGCCCGTGTTTGCAACTGGCTGGTCCACCTGCTGAAT

GAAGCTATTATGAGTGTTGGCGGTCCGCGCGATGCCATTACCAGTGTCGA

ATCCCCGACGATCGACTCCGCTCAAACCCTGATGACGCACGCGGGCGTTC

GTCTGGTCGTGGTTACCGGCGGTCCGGGCGTCGTGCGTGCAGCTATGAAA

TCAGGTAAAAAGGTTATCGCGGCGGGTCCGGGCAACCCGCCGGCGGTTGT

GGATGAAACCGCTAATCTGGCGAAAGCAGCTGCGGCCATTATCAAGGGTG

CATCGATCGATAACAATATTATCTGTACCGCGGAAAAAGAAATTGTCGCG

GTGGCCAGCATCGCAGACGAACTGTCTCGTCTGCTGGGTCAGCGTGGTGC

GCTGGTCCTGGGCGATGCTCAAGTGCGTGCGCTGGAACGCGTGGTTCTGG

ACGGCGAACATGTGAACAAAGAATGGGTTGGCAAGGATGCCAGCCGTATT

GCAGAACAGATCGGTCTGCGTGGCCACGGTTCTGATCTGCGTCTGCTGGT

CTGCCCGGTGGACGAAGGCCATCCGTTTGTCCAACACGAACTGCTGATGC

CGGTGATTGGTCTGGTTCGTGTCAGCGATGCCACCGAAGCAATGGCTACG

GCGGTGCGCGTTGAACATGGCTTTTGTCACACCGCGGTGATGCATAGTAC

GCACATTGACCGTCTGTCCGCGATGGCGCGTGTGTGCAATGCGTCTATCT

TCGTCAAAAACGATTGTAATCTGGCAGGTCTGGGTCTGGGCGGTGAAGGT

TTTACCTCATTCACGATCGCATCGCCGACCGGTGAAGGTCTGACCACGGC

ACGTGATTTCACCCGCGTTCGTCGCTGCACGCTGAAAGAATCTTTTCGCT

-continued

TCGTGGGTTCTGGTAGTGGCTCTGGTTCAGGCAGTGGCTCAGGCTCAGGC

TCGGGCAGTGGTTCT

3. Noncognate Tag-GFP construct (the whole enzyme from which the tag was predicted was fused to GFP): In this case, a different tag formerly identified as Aldehyde dehydrogenases Cterm (Ck1_1074; YP_001394464) and (Ck1_1076, YP_001394466). This tag is a non-cognate tag, in other words it was predicted to associate with shells from a different organism. There appears to still be some association with these shells. In this case, the protein sequence was fused to the C-terminus of GFP.

Protein sequence fused to C-terminus of GFP with the tag in bold:

(SEQ ID NO: 27)
GSGSGSGSGSEPEDNEDVQAIVKAIMAKLNL

DNA sequence fused to the 3' end of the DNA encoding GFP:

(SEQ ID NO: 28)
CTCGAGGGCAGCGGCAGCGGCAGCGGCAGCGGCTCTGAACCGGAAGACAA

TGAAGATGTGCAGGCAATCGTGAAAGCAATTATGGCTAAACTGAACCTG

FIG. 4 shows western blots of these microcompartment fractions with anti-GFP antibody, indicating that GFP is associated with the microcompartment shells when encapsulation tags are present.

Example 4: Microcompartment Shells from *Mycobacterium Smegmatis* Produced in *E. coli*

Shell proteins from *Mycobacterium smegmatis* were used to construct a new synthetic operon as shown in FIG. 5.

The construct was placed under the control of the IPTG-inducible pET-11 vector and expressed in BL21(DE3)RIL cells. Cells were induced with 0.4 mM IPTG and harvested by centrifugation. Cells were lysed using BPER-2 detergent with sonication. Cell suspensions were clarified using a low speed centrifugation step (10,000×g). The supernatant was centrifuged at high speed (60,000×g) to pellet shell assemblies. Further purification with sucrose density gradient centrifugation and agarose gel electrophoresis (0.2%) was performed. Shells were visualized using negatively-stained electron microscopy with a JEOL 1200EX TEM instrument (FIG. 6).

The operon was designed using the sequences as follows:
RBS DNA sequence:

(SEQ ID NO: 29)
TTTTGTTTAGAGAAAGAGGAGAAATACTAG

YP_884687
Protein sequence:

(SEQ ID NO: 30)
MSSNAIGLIETKGYVAALAAADAMVKAANVTITDRQQVGDGLVAVIVTGE

VGAVKAATEAGAETASQVGELVSVHVIPRPHSELGAHFSVSSK

DNA sequence:

(SEQ ID NO: 31)
ATGAGCAGCAATGCAATCGGTCTGATCGAAACGAAAGGCTATGTGGCGGC

ACTGGCAGCGGCGGATGCAATGGTGAAGGCAGCAAATGTCACCATTACGG

ATCGTCAGCAAGTTGGCGACGGTCTGGTGGCGGTTATCGTCACCGGCGAA

GTGGGTGCCGTTAAAGCGGCCACCGAAGCAGGCGCTGAAACGGCAAGTCA

AGTGGGTGAACTGGTGTCCGTTCATGTCATTCCGCGTCCGCACAGCGAAC

TGGGTGCACATTTTAGCGTTAGCTCTAAGTAA

RBS DNA Sequence:

(SEQ ID NO: 32)
TTTAGAGATTAAAGAGGAGAAATACTAG

YP_884690
Protein sequence:

(SEQ ID NO: 33)
MAELRSFIFIDRLQPQTMSYLGTWIKGALPRANMAAQIIEVAPGLDIEGV

TDVALKHAEVKAGILVVERQFGYLEFHGETGAVKAAADAALDYLGGDPDA

AVRPEILASRIISSIDHQHAFLINRNKIGSMVLPGESLFVLEVAPASYAI

LATNEAEKAADVKVVDFRMIGATGRVYLSGTEADVRQAADAARDALAVLQ

GA

DNA sequence:

(SEQ ID NO: 34)
ATGGCCGAACTGCGTAGCTTCATTTTCATTGACCGCCTGCAACCGCAAAC

GATGTCCTATCTGGGCACCTGGATTAAGGGTGCTCTGCCGCGTGCGAACA

TGGCGGCCCAGATTATCGAAGTTGCCCCGGGCCTGGATATTGAAGGTGTT

ACCGACGTCGCCCTGAAACATGCAGAAGTCAAGGCTGGCATCCTGGTGGT

TGAACGCCAATTTGGTTATCTGGAATTTCATGGCGAAACGGGTGCGGTGA

AAGCAGCTGCGGATGCCGCCACTGGACTACCTGGGTGGTGATCCGGACGCT

GCAGTTCGTCCGGAAATTCTGGCCTCTCGCATTATCAGCTCTATCGATCA

TCAGCACGCATTTCTGATTAACCGTAATAAGATCGGCAGTATGGTCCTGC

CGGGTGAATCCCTGTTCGTGCTGGAAGTTGCTCCGGCGAGCTATGCGATT

CTGGCGACCAATGAAGCGGAAAAAGCCGCAGATGTTAAGGTCGTGGACTT

TCGTATGATCGGTGCAACCGGTCGTGTCTACCTGTCGGGCACGGAAGCTG

ATGTGCGTCAGGCTGCAGATGCAGCACGCGACGCACTGGCAGTGCTGCAA

GGTGCCTAA

RBS:

(SEQ ID NO: 35)
TTTAGAGTCACACAGGAAACCTACTAG

YP_884688
Protein sequence:

(SEQ ID NO: 36)
MLRATVTGNVWSTRRIEGIPAGAFLEVEVEGTGSRMIAFDVLGSGVGEHV

LIAQGSVASSWFTGTPPPIDALIIGSIDTRSDSNPAE

DNA Sequence:

(SEQ ID NO: 37)
ATGCTGCGTGCTACCGTTACCGGCAATGTCTGGTCTACCCGTCGTATCGA

AGGCATCCCGGCTGGTGCTTTTCTGGAAGTGGAAGTCGAAGGCACCGGTT

CACGTATGATTGCCTTTGATGTCCTGGGCTCGGGTGTGGGCGAACATGTT

CTGATCGCGCAGGGTAGCGTTGCCAGCTCTTGGTTCACCGGTACGCCGCC

GCCGATTGACGCACTGATTATCGGTAGTATCGATACGCGCAGTGACTCCA

ACCCGGCTGAATAA

Example 5: Production of a Synthetic Metabolic Microcompartment

To produce a synthetic microcompartment to carry out a new metabolic pathway, we designed a strategy to coexpress the *H. ochraceum* shell proteins with Rubisco and carbonic anhydrase for use in cyanobacteria and ultimately for use in transforming plants for increased carbon fixation efficiency. The *H. ochraceum* shell proteins are placed in a neutral site vector for insertion into the genome of *Synechococcus elongatus* PCC 7942 and used to transform *S. elongatus*. Rubisco and carbonic anhydrase sequences are fused to encapsulation tags and coexpressed with the shell proteins. The construct, and variants thereof, particularly of amino acids at pore sites implicated in determining selectivity of pore permeability, are tested for their ability to increase growth of cyanobacterial strains that are dependent on high $CO_2$ concentrations.

In an initial test, the shell proteins from *Haliangium ochraceum* (as described in prior example) were co-expressed with a Rubisco variant in *E. coli* and Rubisco was found to associate with the shells (FIG. 7).

FIG. 7 shows the capture of the non-native enzyme Rubisco by the microcompartment shells produced by *H. ochraceum*. (Left) SDS-PAGE gel showing microcompartment shell proteins pulled down by ultracentrifugation step. (Right) Western blot with anti-Rubisco indicating that Rubisco was pulled down with the shells. Further experiments (not shown) indicate that Rubisco co-purifies with the shells in sucrose density gradient ultracentrifugation steps.

Rubisco Protein sequence:

(SEQ ID NO: 38)
MAAKKYSAGVKEYRQTYWTPDYVPLDTDLLACFKVTPQPGVPREEAAAAV

AAESSTGTWTTVWTDLLTDMDYYKGRCYRIEDVPGDDESFYAFIAYPLDL

FEEGSVTNVLTSLVGNVFGFKALRALRLEDIRFPMAYVKTCAGPPHGIQV

ERDKMNKYGRPLLGCTIKPKLGLSAKNYGRAVYECLRGGLDFTKDDENIN

SQPFQRWRDRFEFVAEAVEKAEAETGERKGHYLNVTAPTPEEMYKRAEFA

KELGAPIIMHDYITGGFTANTGLAKWCRDNGVLLHIHRAMHAVIDRHPNH

GIHFRVLAKCLRLSGGDHLHTGTVVGKLEGDRASTLGYIDLLRESFIPED

RSRGIFFDQDWGSMPGVFAVASGGIHVWHMPALVSIFGDDSVLQFGGGTL

GHPWGNAAGAAANRVALEACVQARNEGRDIEKEGKDILTEAAKHSPELAI

ALETWKEIKFEFDTVDKLDTQ

Rubisco DNA sequence:

(SEQ ID NO: 39)
CATATGGCAGCGAAAAAATACAGCGCAGGCGTGAAAGAATACCGCCAAAC

CTACTGGACTCCCGATTATGTTCCCCTCGATACGGACCTCCTGGCCTGCT

TTAAAGTTACCCCCCAGCCAGGTGTGCCCCGCGAAGAGGCAGCAGCTGCA

GTCGCAGCAGAAAGCTCGACTGGCACCTGGACCACGGTTTGGACCGACCT

GCTCACGGATATGGACTACTATAAGGGTCGCTGTTACCGCATCGAGGATG

TGCCTGGCGATGACGAAAGCTTTTACGCTTTCATTGCATATCCATTGGAT

CTGTTTGAAGAGGGCTCGGTTACTAACGTGCTGACCAGTCTCGTCGGTAA

TGTTTTTGGCTTCAAAGCCCTGCGCGCGCTCCGCTTGGAAGATATCCGCT

TCCCGATGGCCTACGTGAAGACCTGCGCAGGTCCCCCGCATGGCATTCAA

GTCGAACGCGATAAAATGAACAAGTATGGTCGCCCCTTGCTGGGCTGCAC

GATCAAACCGAAGCTGGGTCTCTCGGCTAAAAATTACGGCCGCGCCGTGT

ATGAATGTTTGCGCGGCGGTCTGGATTTTACCAAGGATGACGAGAACATT

AATAGCCAGCCCTTCCAACGCTGGCGCGATCGCTTTGAATTTGTGGCGGA

AGCTGTCGAGAAAGCAGAAGCCGAGACGGGCGAGCGCAAGGGCCATTACC

TGAACGTCACCGCGCCTACGCCAGAAGAGATGTATAAACGCGCTGAATTT

GCAAAGGAGCTCGGCGCTCCCATCATTATGCACGATTACATCACCGGCGG

TTTCACTGCCAACACCGGTTTGGCGAAATGGTGCCGCGACAATGGCGTTC

TCTTGCACATCCATCGCGCCATGCACGCGGTGATTGATCGCCACCCGAAT

CATGGCATCCACTTTCGCGTCCTCGCGAAATGTTTGCGCCTGAGTGGCGG

TGATCACTTGCATACGGGTACTGTGGTCGGCAAGTTGGAAGGTGACCGCG

CCAGCACCCTGGGCTATATTGATCTGCTCCGCGAGAGCTTTATCCCGGAA

GATCGCTCGCGCGGCATCTTTTTCGATCAGGACTGGGGCTCGATGCCCGG

TGTGTTCGCAGTCGCTAGTGGTGGTATCCATGTGTGGCACATGCCGGCGC

TCGTCAGTATTTTTGGCGATGACAGCGTGCTGCAGTTCGGTGGTGGTACC

CTCGGTCATCCTTGGGGTAACGCTGCAGGTGCAGCAGCTAATCGCGTCGC

TCTGGAGGCATGCGTTCAAGCCCGCAACGAAGGTCGCGACATCGAAAAAG

AGGGCAAGGATATTCTCACTGAGGCAGCCAAGCACAGCCCGGAACTCGCA

ATCGCCTTGGAAACGTGGAAAGAGATTAAGTTTGAATTTGATACGGTCGA

CAAACTGGATACTCAATAG

Example 6: Microcompartment Shells from *T. Elongatus* Shell Proteins Produced in *E. coli*

FIGS. 13A-13C, 14A, 14B, 15A, and 15B show synthetic microcompartments (shells) produced by the expression of shell proteins (CcmK(BMC-H), CcmO(BMC-O), and CcmL (BMC-P)) from *T. elongatus* along with diagrams of the various synthetic operons used to express the proteins contained in the shells. All constructs were placed under the control of a pET23b IPTG-inducible vector and expressed in BL21(DE3) cells. Cells were induced with IPTG and harvested by centrifugation. Cells were lysed and cell suspensions were clarified using a low speed centrifugation step. The supernatant was centrifuged at high speed to pellet shell assemblies. Further purification with sucrose density gradient centrifugation was performed. Shells were visualized using negatively-stained electron microscopy with a JEOL 1200EX TEM instrument. FIGS. 13A-13C show GFP labeled shells produced by fusing GFP to the hexamer, CcmK2(BMC-H), and expressing this fusion protein on the same vector as the hexamer, pentamer, and tandem domain proteins; a diagram of this expression construct is shown in FIG. 13C. The construct was expressed as above and shells were purified as above. The electron microscopy image shown in FIG. 13A shows projections consistent with GFP attached to the surface of microcompartment shells. FIG. 14A depicts TEM of unlabeled shells composed of only the shell proteins CcmO(BMC-T), CcmK2(BMC-H), and CcmL(BMC-P) from *T. elongatus*. These represent carboxysome shells containing the minimum complement of BMC domain proteins required to form a shell: one hexameric BMC domain protein (pfam00936), one tandem BMC domain (pfam00936), and one pentameric BMC domain protein (pfam03319), CcmK2(BMC-H), CcmO(BMC-T), and CcmL(BMC-P), respectively. FIGS. 15A and 15B show shells purified using ammonium sulfate precipitation purification and an SDS-PAGE gel showing different shell containing fractions of the ammonium sulfate precipitation purification. The samples that contained the shells shown in FIGS. 15A and 15B were of greater purity than the samples that contained the shells shown in FIGS. 13A-13C, 14A, and 14B, which had a moderate amount of impurities. In the synthetic operon shown in FIG. 15C the shell protein encoding genes are arranged in the following order: ccmK2 (BMC-H), ccmO(BMC-T), and ccmL(BMC-P). This arrangement differs from the arrangements shown in FIGS. 13C and 14B; on those synthetic operons the shell protein encoding genes are arranged as follows: ccmO(BMC-T), ccmK2(BMC-H), and ccmL(BMC-P). All of the shells depicted in FIGS. 13A-13C, 14A, 14B, 15A, and 15B were found to have diameters of approximately 50 nm.

CcmK2 Hexamer (BMC-H) carbon dioxide concentrating mechanism protein [*Thermosynechococcus elongatus* BP-1: NP_681737]

(SEQ ID NO: 40)
MPIAVGMIETRGFPAVVEAADAMVKAARVTLVGYEKIGSGRVTVIVRGDV

SEVQASVAAGVDSAKRVNGGEVLSTHIIARPHENLEYVLPIRYTEAVEQF

RN carbon dioxide concentrating mechanism protein [*Thermosynechococcus elongatus* BP-1: GI:22298490(codon optimized)]

(SEQ ID NO: 41)
ATGCCAATTGCCGTGGGTATGATTGAAACCCGTGGTTTTCCAGCCGTGGT

GGAAGCGGCCGATGCCATGGTGAAAGCCGCGCGTGTTACCCTGGTGGGTT

ACGAGAAAATCGGTAGTGGTCGTGTGACCGTGATTGTGCGTGGTGATGTG

AGTGAAGTGCAAGCCAGTGTTGCGGCCGGTGTGGATAGTGCCAAACGTGT

GAATGGTGGCGAAGTGCTGAGTACCCATATCATTGCCCGTCCACATGAAA

ATCTGGAATACGTGCTGCCAATCCGTTACACCGAAGCCGTTGAACAATTT

CGTAAT

CcmO Tandem Domain (BMC-T)

hypothetical protein tll1148 [*Thermosynechococcus elongatus* BP-1:NP_681938]

(SEQ ID NO: 42)
MERRDDFTDLALGLVSVQSFPAIVGIADHMLKSSDVLLVGYEKIGGGHCT

AIVRGRIADVRLAVEEGAERAQQFGQELSTLVIPRPDPNLEKILPIGSLL

AQIASKSRGHRLSSHAVGLLETRGFPAMVGAADAMLKAADVMLTAYETIG

AGLCTAIIRGTASNTAIALEAGMAEADRIGELHAVMLVPRPLEDLDQSLP

LAPALQRELQPLRLPLTLKQKETEPLALQGAAQASVAVEAAAERVPVDPP

ANP hypothetical protein tll1148 [*Thermosynechococcus elongatus* BP-1: GI:22298691 (codon optimized)]

(SEQ ID NO: 43)
ATGGAACGTCGTGATGATTTTACCGATCTGGCCCTGGGTCTGGTGAGTGT

GCAAAGTTTTCCGGCCATCGTGGGTATCGCCGATCATATGCTGAAGAGTA

GTGATGTGCTGCTGGTTGGTTACGAAAAAATCGGTGGTGGCCATTGCACG

GCGATCGTGCGTGGTCGCATTGCGGACGTGCGCCTGGCGGTGGAAGAGGG

TGCCGAACGTGCCCAACAATTTGGTCAAGAACTGAGTACCCTGGTGATTC

CACGTCCAGATCCAAATCTGGAAAAGATTCTGCCGATTGGTAGTCTGCTG

GCGCAAATCGCGAGTAAAAGTCGTGGTCATCGTCTGAGCAGTCATGCCGT

TGGCCTGCTGGAGACCCGTGGTTTCCCAGCCATGGTGGGTGCGGCGGATG

CCATGCTGAAAGCGGCCGATGTGATGCTGACGGCCTACGAGACCATTGGT

GCCGGTCTGTGTACCGCCATCATTCGCGGCACGGCCAGTAATACCGCGAT

TGCCCTGGAAGCCGGTATGGCCGAAGCCGATCGTATTGGTGAACTGCATG

CGGTTATGCTGGTGCCACGCCCGCTGGAAGACCTGGATCAAAGTCTGCCG

CTGGCCCCAGCCCTGCAACGCGAGCTGCAACCACTGCGTCTGCCACTGAC

CCTGAAACAAAAAGAAACCGAGCCACTGGCGCTGCAAGGTGCCGCCCAAG

CCAGTGTGGCCGTTGAAGCCGCCGCCGAGCGTGTTCCAGTTGATCCGCCA

GCCAATCCA

CcmL Pentamer (BMC-P)

carbon dioxide concentrating mechanism protein [*Thermosynechococcus elongatus* BP-1: NP_681735]

(SEQ ID NO: 44)
MKIARVCGTVTSTQKEDTLTGVKFLVLQYLGEDGEFLPDYEVAADTVGAG

QDEWVLVSRGSAARHIINGTDKPIDAAVVAIIDTVSRDNYLLYSKRTQY carbon dioxide concentrating mechanism protein [*Thermosynechococcus elongatus* BP-1: GI:22298488(codon optimized)]

(SEQ ID NO: 45)
ATGAAAATTGCCCGTGTGTGTGGTACCGTGACCAGTACCCAAAAGAAGA

TACCCTGACCGGTGTGAAGTTTCTGGTGCTGCAATACCTGGGTGAAGATG

GTGAATTTCTGCCAGATTACGAAGTTGCGGCGGACACCGTTGGTGCCGGT

CAAGATGAATGGGTGCTGGTGAGTCGCGGTAGTGCCGCCCGTCACATTAT

CAATGGCACCGATAAACCAATTGATGCCGCCGTGGTGGCCATTATTGATA

CCGTTAGTCGTGATAATTACCTGCTGTATAGTAAACGTACCCAGTACTAA

B1010 ribosome binding site used in the expression constructs in example 6.

(SEQ ID NO: 46)
T TTAAGA AGGAGA TATACC

B1001 ribosome binding site used in the expression constructs in example 6.

(SEQ ID NO: 47)
GG CTAACA TAGGGT GGATCT

SFGFP
Expression product of synthetic construct sfGFP_iGEM gene, complete cds [synthetic construct, KF410612]

(SEQ ID NO: 48)
MRKGEELFTGVVPILVELDGDVNGHKFSVRGEGEGDATNGKLTLKFICTT

GKLPVPWPTLVTTLTYGVQCFARYPDHMKQHDFFKSAMPEGYVQERTISF

KDDGTYKTRAEVKFEGDTLVNRIELKGIDFKEDGNILGHKLEYNFNSHNV

YITADKQKNGIKANFKIRHNVEDGSVQLADHYQQNTPIGDGPVLLPDNHY

LSTQSVLSKDPNEKRDHMVLLEFVTAAGITHGMDELYK

Synthetic construct sfGFP_iGEM gene, complete cds [synthetic construct, GI:532528632]

(SEQ ID NO: 49)
ATGCGTAAAGGCGAAGAGCTGTTCACTGGTGTCGTCCCTATTCTGGTGGA

ACTGGATGGTGATGTCAACGGTCATAAGTTTTCCGTGCGTGGCGAGGGTG

AAGGTGACGCAACTAATGGTAAACTGACGCTGAAGTTCATCTGTACTACT

GGTAAACTGCCGGTACCTTGGCCGACTCTGGTAACGACGCTGACTTATGG

TGTTCAGTGCTTTGCTCGTTATCCGGACCATATGAAGCAGCATGACTTCT

TCAAGTCCGCCATGCCGGAAGGCTATGTGCAGGAACGCACGATTTCCTTT

AAGGATGACGGCACGTACAAAACGCGTGCGGAAGTGAAATTTGAAGGCGA

TACCCTGGTAAACCGCATTGAGCTGAAAGGCATTGACTTTAAAGAAGACG

GCAATATCCTGGGCCATAAGCTGGAATACAATTTTAACAGCCACAATGTT

TACATCACCGCCGATAAACAAAAAAATGGCATTAAAGCGAATTTTAAAAT

TCGCCACAACGTGGAGGATGGCAGCGTGCAGCTGGCTGATCACTACCAGC

AAAACACTCCAATCGGTGATGGTCCTGTTCTGCTGCCAGACAATCACTAT

CTGAGCACGCAAAGCGTTCTGTCTAAAGATCCGAACGAGAAACGCGATCA

TATGGTTCTGCTGGAGTTCGTAACCGCAGCGGGCATCACGCATGGTATGG

ATGAACTGTACAAA

Example 7: Synthetic BMC Operons Derived from Diverse Natural BMC Genes

The spatial organization of enzymes in cells provides a means to regulate and accelerate metabolic pathways. To isolate and enhance specific pathways, bacteria have evolved proteinaceous organelles called bacterial microcompartments (BMCs) that sequester enzymatic steps from the cytoplasm.[1] By encapsulating enzymes and pathway intermediates within a selectively permeable shell, BMCs may increase reaction rates, retain volatile intermediates, protect the cytoplasm from toxic intermediates, and enable recycling of enzyme cofactors.[1-4] The incorporation of synthetic microcompartments in engineered biological systems could similarly increase flux through specific metabolic pathways and allow new strategies for control of information and metabolites in the cell.

The potential of synthetic BMCs has been recognized for various applications. Incorporation of new carbon-fixing BMCs (synthetic carboxysomes) into plants could increase biomass and carbon flux to biosynthetic pathways.[5, 6] Other synthetic microcompartments could be used to isolate engineered metabolic pathways from host cells to reduce toxicity and increase output.[7, 8] Encapsulation could increase shelf lives or facilitate catalyst removal in biocatalytic systems. [9] Microcompartments have additional potential application in therapeutics, including use as drug delivery vehicles and as scaffolds for vaccine development. [10] These diverse applications will require microcompartment systems that are robust to engineering experiments, are of precisely defined composition, and are amenable to detailed physical characterization.

To facilitate the design of new microcompartments, we sought to identify BMC shell systems that meet requirements for engineering: reliable purification of homogeneous compartments from genetically tractable organisms like *E. coli*, stability and amenability to mutation, and the capability of encapsulating new enzymes. While heterologous expression in *E. coli* has been reported for the three most well-characterized BMC systems, carboxysomes, propanediol utilization (pdu) compartments, and ethanolamine utilization (eut) compartments, substantial heterogeneity and low yields have been reported for these preparations.[11-13] Thus, we reasoned that screening the microcompartment shell proteins from the diversity of natural BMC proteins in sequenced genomes might enable discovery of shell systems more amenable to engineering and physical characterization.

We surveyed a diverse set of natural BMC gene clusters, many of unknown function, to identify new shell building blocks. We then designed a general strategy for producing synthetic BMC operons and found that one construct stood out in producing robust preparations of shells in high yield from expression in *E. coli*. This construct contained the seven BMC shell proteins found in the recently sequenced genome of the halophilic myxobacterium *Haliangium ochraceum*.[14] The homogeneity and small size of these shells enabled the construction of a structural model, suggesting roles for the individual shell proteins. New proteins could be targeted to these shells by fusion to peptide encapsulation tags, enabling design of new synthetic microcompartments. The tractability of this system should enable fundamental structural and mechanistic investigations of BMC function. Moreover, this system demonstrates the feasibility of producing self-assembling shells from diverse BMC building blocks selected from genomic sequence data without regard to native function or genomic context.

To identify BMC systems with properties needed for engineering, we selected a set of diverse, mostly uncharacterized natural BMC-associated genes and developed a general strategy for design of synthetic operons for heterologous expression of their shell genes in E. coli.

Natural BMC gene clusters vary widely in composition and gene arrangement, but all contain genes that encode shell proteins. Three types of BMC shell proteins exist, identified here as hexamers or BMC-H, tandem domains or BMC-T, and pentamers or BMC-P, that together form polyhedral shells (FIGS. 1A and 1B). BMC-H polypeptides contain a single domain of the pfam00936 family from the pfam database[15], about 90 amino acids, that assembles into a six-fold symmetric hexamer in available crystal structures.[16-18] This type of subunit represents the most abundant component of characterized BMC shells.[19-21] Tandem domains (BMC-T) contain two pfam00936 domains in a single polypeptide. These proteins form trimers with a pseudo-hexameric configuration that is sometimes found stacked into a double layer in crystal structures.[17, 18, 22, 23] The third and least abundant shell proteins, referred to here as pentamers or BMC-P, contain a single domain of the pfam03319 family. The five-fold symmetric assemblies formed by these units are presumed to occupy the vertices of icosahedral shells.[17, 18, 24]

Shell protein genes from eight BMC systems, many of unknown function, were selected for experimental testing (Table 1). These systems were chosen to sample from the diversity of BMCs in sequenced genomes in the number and types of shell proteins and the enzymes clustered with them. In several cases, the genes encoding shell proteins are found on multiple loci within the bacterial chromosome. The lack of a conserved number and order for shell protein genes form the various BMC gene clusters and the differences in transcription and translational initiation signals among organisms necessitated a generalized strategy for constructing synthetic BMC shell operons for testing.

carboxysomal protein CcmN reveals common feature of bacterial microcompartment assembly. *Journal of Biological Chemistry* 287, 17729-17736); encapsulation peptides are primary structure extensions at the N- or C-termini (relative to homologs found in genomes lacking BMC loci), the extension contains a short region (15-20 amino acids) that is predicted to form an alpha helix by typical secondary structure prediction tools (e.g. JPRED; Website compbio-.dundee.ac.uk/www-jpred/). This helix is separated from the functional domain of the protein by a poorly conserved and often low complexity linker. The helical conformation of an encapsulation peptide has recently been confirmed by NMR solution structure analysis (Lawrence, A. D., Frank, S., Newnham, S., Lee, M. J., Brown, I. R., Xue, W-F., Rowe, M. L., Mulvihill, D. P., Prentice, M. B., Howard, M. J. and Warren, M. J. Solution structure of a bacterial microcompartment targeting peptide and its application in the construction of an ethanol bioreactor. *ACS Synthetic Biology*). Based on these criteria, the sequence of the predicted aldolase encapsulation peptide is RDDLVRVIR-EELVRALA (SEQ ID NO:52) while that of the aldehyde dehydrogenase is ALREDRIAEIVERVLARL (SEQ ID NO: 54). Moreover, the closest homologs to both *H. ochraceum* aldehyde dehydrogenase and aldolase also contain the extensions at their N- and C-termini and are found in other BMC gene clusters, strongly suggesting that they are involved in the metabolic function of the BMC. A third locus contains a gene encoding a BMC-T subunit; its adjacent genes do not resemble any other BMC-associated genes. Although the *H. ochraceum* shell protein genes are spatially separated, they are very likely associated with a single BMC. A scattered distribution of BMC genes encoding a single type of organelle is not uncommon; the beta-type carboxysome is a well-known precedent. The presence of an aldehyde dehydrogenase gene suggests that, like other catabolic BMCs, the *H. ochraceum* BMC sequesters an aldehyde intermediate. However, gene context does not provide further clues to the function of this uncharacterized BMC. Transmission electron microscopy of thin sections of *H. ochraceum* grown under standard cultivation conditions (DSM catalog 14365) show no obvious evidence of BMCs (see Supplemental Material). Expression of the organelle likely requires the

TABLE 1

BMC clusters selected for testing.

| Organism | Proposed BMC function | Hexamers BMC-H | Tandem BMC-T | Pentamers BMC-P |
|---|---|---|---|---|
| *Alkaliphilus metalliredigens* QYMF | Unknown | 3 | 0 | 1 |
| *Clostridium phytofermentans* ISDg | Unknown | 4 | 1 | 1 |
| *Clostridium phytofermentans* ISDg | Ethanolamine utilization | 2 | 3 | 1 |
| *Leptotrichia buccalis* C-1013-b, DSM 1135 | Ethanolamine utilization? | 4 | 2 | 1 |
| *Mycobacterium smegmatis* MC2 155 | Unknown | 1 | 2 | 1 |
| *Planctomyces limnophilus* Mu 290, DSM 3776 | Unknown | 2 | 0 | 3 |
| *Rhodopseudomonas palustris* BisB18 | Unknown | 3 | 2 | 1 |
| *Haliangium ochraceum* SMP-2, DSM 14365 | Unknown | 1 | 3 | 3 |

The *H. ochraceum* shell proteins are found on three distinct chromosomal loci (FIG. 2). The most extensive locus contains genes encoding four shell proteins (one BMC-H, two BMC-T, and one BMC-P) and a putative aldehyde dehydrogenase. A second locus encodes two BMC-P proteins and a putative aldolase. The amino acid sequences of both the aldehyde dehydrogenase and aldolase contain BMC encapsulation peptides at their N- and C-termini, respectively. These were predicted using the criteria of Kinney et al ((2012). Elucidating essential role of conserved presence of the substrate as observed for all catabolic BMCs characterized to-date (i.e. Eut, Pdu, and two distinct types of fucose catabolizing metabolosomes found in *Clostridium phytofermentans* and *Planctomyces limnophilus*). See Roof, D. M. a. R., J. R. (1988). Ethanolamine utilization in *Salmonella typhimurium*. *Journal of Bacteriology* 170, 3855-3863; Bobik, T. A., Ailon, M., Roth, J. R. (1992). A single regulatory gene integrates control of vitamin B12 synthesis and propanediol degradation. *Journal of Bacteriology* 174, 2253; Petit E, L. W., Coppi M V, Warnick T A, Currie D, Romashko I, Deshpande S, Haas K, Alvelo-Maurosa J G, Wardman C, Schnell D J, Leschine S B, Blanchard J L. (2013). Involvement of a Bacterial Microcompartment in the Metabolism of Fucose and Rhamnose by *Clostridium phytofermentans*. *PLoS One* 8:e54337; and Erbilgin, O., McDonald, K. L. and Kerfeld, C. A. Characterization of a Planctomycetal Organelle: A Novel Bacterial Microcompartment for the Aerobic Degradation of Plant Saccharides. *Applied and Environmental Microbiology* in press.

The fact that these genes are found on distinct chromosomal loci and the absence of information about transcriptional and translational levels of the *H. ochraceum* shell proteins necessitated the construction of a synthetic operon for expression of the *H. ochraceum* genes (FIG. 2). We designed the operon to mimic shell protein ratios typical of natural BMCs that have been isolated from native organisms. Shell genes from *H. ochraceum* were synthesized with *E. coli* codon optimization in a single operon: the BMC-H subunit was placed first, followed by the genes for the BMC-T and then the BMC-P proteins. The BMC-H gene was preceded by a ribosomal binding site (RBS) with high predicted translation initiation rates, the BMC-T genes were preceded by intermediate RBS sequences, and BMC-P genes with low-level RBS sequences.

These gene constructs were expressed in *E. coli* under control of the T7 promoter. Because BMCs typically sediment upon centrifugation at ~50,000×g [19-21] the cell extracts were ultracentrifuged and screened for the presence of shell proteins in the pelleted fraction. From this screen, a construct built from the shell proteins of *Haliangium ochraceum* was identified as producing a distinct pattern of four proteins upon expression and ultracentrifugation, suggesting the presence of assembled structures (FIG. 2). We discuss purification, characterization, and encapsulation experiments with the resulting shells in the following sections. In addition to shells identified from *H. ochraceum*, ultracentrifuge extracts revealed shell proteins in a few other cases (data not shown) and thin-section electron microscopy of *E. coli* cells expressing the synthetic operons showed a diverse range of cellular structures as has been previously observed upon expression of pdu and eut BMC shell genes in *E. coli*.[12, 13]

Purification of Microcompartment Shells.

Purification and electron microscopy experiments established that assembled microcompartment shells were produced upon heterologous expression of the *H. ochraceum* construct in *E. coli*. Ultracentrifuge extracts from expression of the *H. ochraceum* construct were fractionated by density gradient ultracentrifugation as well as by electrophoresis on 0.2% agarose[19], revealing in both cases a consistent pattern of four bands by SDS-PAGE (FIG. 2). Trypsin digests and mass spectrometry unambiguously identified these bands as the single BMC-H and three BMC-T proteins encoded by the synthetic *H. ochraceum* operon (FIG. 2). The three BMC-T proteins are distinguished here with their gene locus tag numbers. The protein encoded by locus tag Hoch_5812 is referred to as BMC-T(5812), for example. BMC-P proteins are expected to represent minor components of shells [17, 18, 24] and were not detected by mass spectrometry. Thus, from this construct, four major shell protein components are expected in assembled shells, and all four major components co-purified in constant ratios.

Negatively stained electron microscopy with these purified fractions revealed distinct microcompartment shells (FIG. 3A). To allow further identification of the shells as products of heterologous expression, we specifically labeled the shell proteins. Upon immunogold labeling of these extracts with antibodies raised against *H. ochraceum* shell proteins, electron microscopy (TEM) indicated the association of gold particles with the shells (FIG. 3B). The expected icosahedral symmetry was supported by the appearance of facets in some TEM images, a nonrandom distribution of angles between gold particles, and the observation of triangular placement of gold particles (See SI Appendix).

We tested whether shells could be visualized in TEM images of sectioned *E. coli* cells. Shells were not readily evident in these images. The difficulty in viewing shells in sectioned cells may be due to the fact that the thickness of the TEM sections (40 nm) is similar to the shell diameter. Thus, cellular material is expected to contribute substantially to the TEM signal relative to the shell outline that is seen clearly with purified compartments in FIG. 3A. Because unambiguous visualization of the shells within *E. coli* cells was not obtained, there remains the possibility that the shells could assemble during the purification process rather than in vivo. Nevertheless, it is contemplated that the dark areas visible in the TEM images may contain a combination of densely packed shells and overexpressed shell proteins. Further experiments to label the shell proteins within cells may distinguish between these possible scenarios. Herein, we focus on characterizing the components and stoichiometry of the purified shells and we propose models for their construction.

The shells were remarkably homogeneous and could be isolated in high yield. Measured diameters of the shells from TEM images were 39±2 nm (79 shells measured). The particles were thus smaller and more homogeneous in size than those of previously isolated BMCs, including carboxysomes, pdu, or eut compartments, which have ranged in diameter from about 90-150 nm and have had standard deviations, where reported, of more than 20% of the diameter.[11-13, 20, 21, 25] Shell particle yields were also high. From protein concentrations, the quantity of shells was estimated at $10^{12}$-$10^{11}$ particles per L of culture. Consistent with this figure, a lower limit of $10^{11}$-$10^{10}$ particles per L of culture yield was estimated based on particle densities on electron microscopy grids. The shells appeared stable for two months or more at 4° C., and could be maintained in simple buffers or water.

Requirements for Shell Formation.

As a step toward determining the composition and construction of these shells, we sought to identify which of the seven *Haliangium ochraceum* genes were required for shell formation. Constructs were generated to systematically knockout individual shell genes either by complete removal or by mutagenesis to insert stop codons early in the gene. These constructs were tested for the presence of shell proteins in ultracentrifuge pellets and for the production of shells detectable by TEM.

Knockout of the single BMC-H gene led to loss of all shell proteins in ultracentrifuge extracts as well as loss of all detectable shells with TEM. This result was expected, as hexamers represent the major component of the shells. Although necessary, the BMC-H subunit alone was not sufficient to produce shells. When only the BMC-H subunit was expressed, shells were not detected in TEM studies of ultracentrifuge extracts. However, some BMC-H was detected in these extracts by SDS-PAGE, suggesting the possibility of higher-order structures or insolubility. Indeed, TEM images from pure BMC-H protein revealed extensive sheets of packed hexagons (FIG. 4A). Spacing of individual units in these images was estimated at 7.5 nm per hexamer, consistent with ~70 Å diameter of BMC-H homologs that have crystallized in layers.[16-18] These two-dimensional assemblies are discussed further below.

In contrast to BMC-H, BMC-P subunits are expected to be minor components of icosahedral shells; only 60 monomers or 12 pentamers are required to close an icosahedral shell. The calculated molecular weights of the three BMC-P proteins (9-13 kD) overlap with that of the abundantly produced BMC-H subunit (10 kD), so these proteins cannot be distinguished by SDS-PAGE. Mass spectrometry of the BMC-H band from SDS-PAGE did not reveal the presence of any of the three BMC-P proteins. Thus, it remains unclear whether BMC-P subunits were present and undetectable by mass spectrometry or whether BMC-P proteins were not present at all in the purified shells. This is not without precedent; despite decades of research on purified carboxysomes, it was only with the availability of antibodies that BMC-P proteins were identified in Western Blots.[17, 18, 24] We were not able to produce antibodies to *H. ochraceum* BMC-P proteins in this work. No cross-reactivity was found with antibodies for the CsoS4B BMC-P protein from the *Prochlorococcus marinus* MED4 carboxysome, which has less than 30% sequence identity with any of the three *H. ochraceum* BMC-P proteins.

To determine whether or not the BMC-P genes were required in the synthetic operon for production of shells, we knocked out each individual BMC-P gene and also deleted all three BMC-P genes simultaneously from the operon. We found that any individual BMC-P gene could be knocked out, and further, that shells were formed even upon simultaneous deletion of all three BMC-P genes. Expression of a construct consisting only of BMC-H and three BMC-T proteins resulted in an SDS-PAGE banding pattern identical to that from the full seven-gene construct (FIG. 4B). Moreover, shells produced without the BMC-P genes were identical in diameter from those produced from the seven-gene construct (FIG. 4C). These results indicate that the BMC-P subunits are not required for formation of the shells. *E. coli* BL21 (DE3) cells also contain a gene of the pfam03319 family, with 36%, 36%, and 43% identity with the three pfam03319 proteins of *H. ochraceum*. It is possible that a small number of these natural *E. coli* proteins could also be incorporated into the shells. However, because these genes were not overexpressed and would not naturally be upregulated under the growth conditions, we strongly expect these proteins to be present in very small numbers. No *E. coli* shell proteins were detected by mass spectrometry.

This work is consistent with prior work that has indicated that carboxysomes are assembled in *H. neapolitanus* even upon deletion of all BMC-P genes.[40] BMC-P units may thus act in some systems more like caps to seal the vertices of the shells than crucial structural elements. In other systems, BMC-P proteins may have more essential structural roles, as a CcmL deletion resulted in elongation of the majority of beta carboxysomes formed[41] and PduN was required for heterologous production of the Pdu compartment.[29] On the other hand, BMC shells have been reported to form in *E. coli* by the expression of a single BMC-H protein from the Eut system; these shells are therefore devoid of any BMC-P subunits[28].[26].

Our results do not allow us to distinguish between two different possible scenarios for BMC-P proteins expressed from this synthetic *H. ochraceum* operon system. The BMC-P proteins may be present in shells but not detectable and, at the same time, not required for shell formation. Alternatively, it is also possible that the BMC-P proteins are not expressed or are not present in the shells. Experiments to produce antibodies against BMC-P proteins and to increase expression levels of the BMC-P protein may be necessary to determine whether or not BMC-P proteins can be incorporated into shell vertices. Because BMC-P proteins are expected to seal the shell, thereby completing the diffusional barrier required for substrate concentration,[40] the production *H. ochraceum*-based synthetic shells for sequestering substrates around encapsulated enzymes will require the presence of BMC-P pentamers.

We next probed the roles of the distinct BMC-T subunits. As noted above, expression of the hexamer subunit alone did not produce detectable shells, suggesting a requirement for BMC-T subunits. FIG. 4D shows the results of knocking out BMC-T proteins by mutagenesis to place a single stop codon within in the first 10 amino acids. Removal of BMC-T(5812) led to a >10-fold reduction in yield of shells. In contrast, deletion of BMC-T(5816) led to little or no reduction in shell yield and deletion of BMC-T(3341) led to ~2-fold reduction in shell yield. Shells could be detected by TEM in extracts from all three deletion mutants, although in substantially reduced numbers for the BMC-T(5812) deletion construct. The different effects of stop codons on shell yields among the three BMC-T units suggest that BMC-T(5812) may play a different or more crucial role, or that BMC-T(3341) and BMC-T(5816) may be functionally interchangeable. We note that, upon deletion of BMC-T(3341) or BMC-T(5816), the levels of the remaining BMC-T do not increase to the extent expected for full replacement of the missing BMC-T (FIG. 4D), indicating either that these two proteins may not be fully interchangeable or that their concentration in the cell is limiting. As discussed in the next section, sequence comparisons also reflect distinctions between BMC-T(5812) and the other two BMC-T units.

While the fact that shell yields were not reduced substantially upon knockout of BMC-T(5816) or BMC-T(3341) suggests possible redundancy of these two proteins, different results were obtained when the BMC-P subunits were deleted. A construct comprising only three genes, BMC-H, BMC-T(5812), and BMC-T(3341) (or, in other words, lacking both BMC-T(5816) and the BMC-P genes) was tested for the presence of shells in ultracentrifuge pull-down experiments. In these experiments, no shell proteins were visible by SDS-PAGE in the extracts from ultracentrifugation, indicating a dramatic reduction in shell yield. These results suggest that BMC-T(5816) could play a distinct role from BMC-T(3341) or that its presence could help to stabilize the icosahedron in the absence of pentameric caps.

Collectively, these results suggest that shell formation is facilitated by the energetically favorable formation of two-dimensional arrays from hexamers (FIG. 4A), and that tandem BMC domain proteins may be required to produce the curvature needed for complete shells even in the absence of BMC-P. We next evaluated the composition of shells more quantitatively with the goal of identifying specific roles for individual BMC proteins.

A Model for Shell Construction.

We used the available data to build a structural model for the shells. The remarkably consistent diameter measured in TEM experiments (39±2 nm, see above) combined with the dimensions of packed BMC-H hexamers (FIG. 4A), available crystal structures for shell protein homologs, and icosahedral construction placed strong constraints on possible geometries for the shell model. The resulting structural model comprised 12 pentagonal vertices and 260 hexagonal units, with 13 hexagons per face (FIG. 5C). In viral capsid nomenclature, this model corresponds to a triangulation number of T=27.[27]

We next used additional data to propose possible models for placement of individual shell proteins within the shell structure. The stoichiometry of individual shell proteins in purified shells was estimatedby three methods. First, densitometry of SDS-PAGE gels with coomassie or silver staining gave mass ratios of 3:1:1:1 and molar ratios of 7:1:1:1 for monomeric units of the BMC-H and three BMC-T proteins, respectively. Because pentamers were not identified by mass spectrometry and no difference in stoichiometric ratio was detected between the 7- and 4-gene constructs, pentamers were not considered in determining stoichiometry. The molecular weights of the three BMC-T proteins are within 5% of each other and thus mass ratios and molar ratios of the BMC-T proteins are the same within error. Second, concentrations of individual purified shell proteins were determined by amino acid analysis and compared by titration on SDS-PAGE gels to purified shells to give molar ratios of 8:1:1:1. Third, amino acid analysis was performed directly on purified shells and the molar ratio was optimized to minimize the variation in particle concentration determined from each of the 14 individual amino acids that could be measured. This analysis also yielded a molar ratio of 8:1:1:1.

To place the shell protein stoichiometry within the context of the structural model, information about the biological assemblies of BMC-T and BMC-H subunits was required. BMC-T subunits have been shown to form double-layered hexameric assemblies as well as single-layered trimers in crystal structures.[21; 43; 44; 45] Similarly, BMC-H proteins could form single-layered hexamers or, as recently proposed, double-layered dodecamers.[31] Thus, in calculating the number of hexagonal units in the icosahedral model, we considered possible scenarios in which both BMC-T and BMC-H subunits could be either single- or double-layered (FIG. 5A).

Combining these models with molar ratios of monomeric subunits of 8:1:1:1 and a structural model with 13 hexagons per face yields calculated values for the number of BMC-T or BMC-H hexagons in each face of the icosahedron (FIG. 5A, bottom). Models 2 and 3, in which both BMC-H and BMC-T are single- or double-stacked, yield a possible symmetric arrangement of hexagons, suggestive of different functional roles for the proteins. In these models, BMC-T pseudohexamers could serve the purpose of interacting with BMC-P pentamers to form five-fold vertices and producing curvature at intersections of the icosahedral faces. In contrast, Models 1 and 4 yield only asymmetric or random distributions of BMC-T and BMC-H.

To produce a more detailed model for shell construction, we considered sequence identities of the individual BMC-T subunits with available crystallographic structures. BMC-T (3341) and BMC-T(5816) have the greatest sequence identities (57% and 52%, respectively) with CcmP, a beta-type carboxysome BMC-T subunit that forms double-stacked layers in crystal structures. [22] These proteins contain conserved residues that line the trimer-trimer interface and are proposed to play a role in determining whether BMC-T units are single- or double-layered.[23] In contrast, BMC-T(5812) has the greatest sequence similarity (36%) with a PduT, a BMC-T unit from the pdu compartment that forms single-layered trimers.[28] These sequence similarities are consistent with the observations from BMC-T knock-out studies, suggesting that BMC-T(5812) may play a distinct role from BMC-T(5816) and BMC-T(3341). These differences are incorporated into Model 5 (FIG. 5B), which assigns the BMC-T subunits to distinct structural roles in shell construction. In this model, BMC-T(5812) forms a single layer that forms junctions between icosahedral faces while interacting with BMC-T(5812) and BMC-H units.

Model 5, although speculative, is consistent with the amino acid analysis data. Measurements of the thicknesses of shells from TEM images were consistent with an overall double-layered shell, although the limitations of this type of measurement do not allow us to reliably determine the thickness and a single-layered shell cannot be ruled out. Immunogold labeling with antibodies raised against BMC-T(5812) showed triangular shapes, as seen in FIG. 3B, consistent with placement of these subunits at the vertices of the shells. Antibodies raised against BMC-T(3341) or the BMC-H subunit either showed no labeling or showed shell labeling without notable geometric patterns. Some TEM images showed thinning of the shell wall with angles that match those between the vertices of icosahedral structures, consistent with a reduced thickness from placement of single-layered BMC-T(5812) at the vertices (see SI Appendix). As noted above, deletion of BMC-T(5812) subunits substantially reduced the shell yield, supporting a distinct and non-redundant function for this type of subunit. Exact stoichiometries for Models 1-5 were all consistent with amino acid analysis data. Crystallographic structure determination and/or systematic perturbation of the individual shell proteins may provide further evidence to define the shell construction.

Together, the data support a shell structure composed of 260 hexagonal units and 13 hexagons per face. Based on stoichiometries of proteins in purified shells, we can propose five possible models for the placement of individual shell proteins. We emphasize that Models 1-5 are speculative and, although experimental evidence is consistent with these models, our data do not allow us to differentiate between them. We suggest that the energetically favorable self-association of BMC-H units to form layers (FIG. 4A) plays a key role in shell formation and that the different BMC-T proteins are required to stabilize the five-fold vertices and promote the curvature needed to form shells.

Targeting Proteins for Association with the Shell

The development of BMCs for compartmentalizing reactions or as polyvalent scaffolds will require the incorporation of enzymes that may not normally be expressed or associated with a BMC in the host organism. We tested whether a new protein (GFP) could be associated with the shells by fusion to either the aldehyde dehydrogenase (Hoch_5813, FIG. 2) of the native *H. ochraceum* BMC or its predicted encapsulation peptide. Encapsulation peptides have been recently predicted at the N- and C-termini of many BMC enzymes and are proposed to form alpha-helical structures that interact with shell proteins in order to incorporate the enzymes into the BMC.[32, 33] A gene encoding a putative aldehyde dehydrogenase that lies adjacent to BMC shell genes in the *H. ochraceum* genome (locus tag Hoch_5813) is predicted to have an encapsulation peptide sequence at its N-terminus.[32]

Three constructs were co-expressed with the *H. ochraceum* shell proteins: GFP alone, GFP fused to the full-length sequence of the aldehyde dehydrogenase, and GFP fused to the first 34 residues at the N-terminus of this enzyme, the predicted encapsulation peptide (FIG. 6). A (GlySer)$_{10}$ linker was used in both fusions. Western blots of purified shells from these coexpressions indicated that GFP alone was not associated with the shells, whereas GFP fused to either the N-terminal region or the full enzyme was associated with the purified shells (FIG. 6). BMCs produced in the presence of these GFP constructs did not differ in size or morphology in TEM images from those produced without the GFP constructs. Both GFP fusions were found to copurify with shell proteins in sucrose density gradient ultracentrifugation experiments. Individual compartments were not visualized by fluorescence microscopy using the GFP label, as the cells glowed uniformly green, presumably due to excess GFP not associated with the compartments.

The ability to incorporate new proteins into the shells enables the design of new metabolic compartments as well as fundamental studies to understand the quantitative effects of enzyme encapsulation. The efficiency of association of the peptide tag complex with shells was lower than that of the full enzyme complex (FIG. 6). This observation suggests that either there are additional features of the full enzyme that help to recruit it to the shells or that the GFP-tag complex that we selected was not optimally suited for recruitment due to aggregation, suboptimal linker structure, or other factors.

Although the efficiency of targeting to the compartments was not high—western blots were needed to detect the associated GFP—these results do provide evidence that new proteins can be targeted for association with the compartments by fusion to encapsulation peptides or to enzymes associated with the native compartment. The simplest interpretation of these results is that these proteins are encapsulated within the lumen of the compartment as would be expected for the natural BMC enzyme. However, our experiments are not able to identify the location of the proteins, and it remains possible that the proteins are associated with the shells or the exterior of the compartments rather than encapsulated within the compartments. Indeed, the suggestion that some BMC enzymes associate with the external surface of the shell and "inject" metabolites into the compartment has recently been proposed for the Eut BMC (Huseby, D. L. & Roth, J. R. (2013). Evidence that a metabolic microcompartment contains and recycles private cofactor pools. *Journal of Bacteriology* 195, 2864). Other studies reporting encapsulation peptide-mediated targeting to BMCs were likewise unable to distinguish if the targeted protein localized to the lumen or was superficially associated with the shell (Sargent, F., Davidson, F. A., Kelly, C. L., Binny, R., Christodoulides, N., Gibson, D., Johansson, E., Kozyrska, K., Lado, L. L., MacCallum, J., Montague, R., Ortmann, B., Owen, R., Coulthurst, S. J., Dupuy, L., Prescott, A. R. and Palmer, T. (2013). A synthetic system for expression of components of a bacterial microcompartment. *Microbiology* 159, 2427-2436; Lawrence, A. D., Frank, S., Newnham, S., Lee, M. J., Brown, I. R., Xue, W-F., Rowe, M. L., Mulvihill, D. P., Prentice, M. B., Howard, M. J. and Warren, M. J. Solution structure of a bacterial microcompartment targeting peptide and its application in the construction of an ethanol bioreactor. *ACS Synthetic Biology*. Unequivocally identifying the location of heterologous cargo in synthetic shells is important for determining their potential applications. Future experiments will be needed to distinguish between these alternative possibilities; the results will dictate whether the *H. ochraceum* system is better suited for compartmentalization of enzymes or as a three-dimensional scaffold.

Further Implications

Engineered BMCs as either scaffolds or compartments have the potential to increase product yields in metabolic engineering and to open up new avenues in biotechnology and synthetic biology. Further, understanding the self-assembly and function of BMCs will shed light on diverse biological processes including $CO_2$ fixation and bacterial pathogenicity in the mammalian intestine.[1, 34] Here we have described a new synthetic shell system based on the composition of a BMC that has only been characterized bioinformatically. This synthetic shell system offers essential advantages for both fundamental physical studies and engineering applications: a defined and homogeneous structural composition, reliable purification in high yield from *E. coli*, stability and robustness, and the potential for targeted association with new proteins.

The microcompartment shell system described here differs substantially from natural BMC particles that have been isolated previously, with a much smaller and more uniform size.[11-13, 20, 21, 25] The size and uniformity enabled the construction of a structural model that includes 260 hexagonal units total and 13 hexagonal units per icosahedral face (FIG. 5C). A further quantitative analysis of shell composition was used, in combination with sequence analysis, to suggest possible placements of the individual shell proteins within the shell structure. We propose that the BMC-H units readily self-assemble to form sheets as in FIG. 4A and that BMC-T units may serve to produce the curvature needed for shells and to produce the binding sites for pentameric vertex assemblies. Our model further suggests that two types of BMC-T units may have distinct roles in producing the icosahedral assembly. BMC-P units, in contrast, did not appear to be necessary for the formation of shells in this system, although they are expected to be a necessary component of the diffusive barrier needed for metabolic function.[26] The defined composition of these shells should enable systematic perturbations to further understand structural and functional roles of each unit.

This shell construct was produced synthetically, retaining no information about gene order, genome context, or potential biological function of the putative *H. ochraceum* microcompartment. The synthetic operon was designed to produce expression levels that mimic protein abundances in natural BMCs, the shell proteins were assembled into a new operon. It remains unknown whether the structure and properties of the shells are the same as those in the native *H. ochraceum* microcompartment in vivo, or whether an alternative type of shell is produced from this synthetic construct in *E. coli*. The native BMC has not been characterized and is not evident in TEM images of the organism grown under standard media conditions. Visualization of native BMCs by TEM typically requires induction of BMC production (Roof, D. M. a. R., J. R. (1988). Ethanolamine utilization in *Salmonella typhimurium*. *Journal of Bacteriology* 170, 3855-3863; Bobik, T. A., Ailon, M., Roth, J. R. (1992). A single regulatory gene integrates control of vitamin B12 synthesis and propanediol degradation. *Journal of Bacteriology* 174, 2253; Petit E, et al; Erbilgin, O., McDonald, K. L. and Kerfeld, C. A. Characterization of a Planctomycetal Organelle: A Novel Bacterial Microcompartment for the Aerobic Degradation of Plant Saccharides. *Applied and Environmental Microbiology* in press. (2013). Involvement of a Bacterial Microcompartment in the Metabolism of Fucose and Rhamnose by *Clostridium phytofermentans*. *PLoS One* 8:e54337.) for example by growing cells under conditions where the BMC-encapsulated metabolic pathway is required for growth. However, because the natural function of the *H. ochraceum* BMC is not known, isolation and characterization of the native BMC remains a challenge.

The goal of the present study was to devise methods for the production of synthetic shells to use as compartments or protein scaffolds for bioengineering, not to learn the function of the *H. ochraceum* BMC. In fact, this study is distinctive for its approach to synthetic shell production without regard to native function. The remarkable properties of these synthetic shells relative to results from the more familiar carboxysome, Pdu, and Eut systems illustrates the importance of sampling shell protein building blocks from the diversity of BMCs now apparent in sequenced genomes. The extent to which individual shell proteins can be swapped among different BMC types and source organisms remains unknown. But by heterologously coexpresing functionally related BMC shell proteins, it may be possible to produce other types of shells, even when the native functions are not known. Our results suggest that taking advantage of the many remaining BMC clusters of unknown function may offer new surprises and insights into BMC function and assembly Engineered BMCs have the potential to increase product yields in metabolic engineering and to open up new avenues in biotechnology and synthetic biology. Further, understanding the self-assembly and function of BMCs will shed light on diverse biological processes including $CO_2$ fixation and bacterial pathogenicity in the mammalian intestine.[1, 34] Here we have described a new synthetic shell system that offers essential advantages for both fundamental physical studies and engineering applications: a defined and homogeneous structural composition, reliable purification in high yield from *E. coli*, stability and robustness, and the ability to encapsulate new proteins.

Materials and Methods

Construction of Synthetic Operons.

For each natural BMC cluster, the shell proteins were categorized by type and placed in the following order after the promoter sequence: all BMC-H genes, all BMC-T genes, and finally all BMC-P genes. A ribosomal binding site sequence (RBS) was placed before each gene, such that expected translation initiation rates were greatest for BMC-H units and least for BMC-P units. Target predicted initiation rates had BMC-T and BMC-P genes at levels of about 50% and 5% of the predicted value for BMC-H, respectively. Gene synthesis was performed by Genscript using *E. coli* codon optimization.

Expression of Shell Proteins and Purification of Shells.

Synthetic operons were placed under the control of the T7 promoter in the pET-11 vector. Protein production in *E. coli* BL21-CodonPlus(DE3)-RIL was induced with 0.45 mM IPTG and cells were grown for 3-5 hours after induction at 37° C. Harvested cell pellets were suspended in (per 1 L growth): 2 mL TEMB buffer (5 mM Tris-Cl, 1 mM EDTA, 10 mM $MgCl_2$, 20 mM $NaHCO_3$, pH 8.0), 2 μL lysozyme (50 mg/mL), 10 μL DNAseI (2000 U/mL), 5 μL RNAse A (10 mg/mL). After a brief sonication (2×20 sec, 20% intensity, Branson micro tip), 2 mL BPER-II (Pierce) was added and the suspension was rocked at room temperature for 30 minutes. Cell debris was removed with an initial centrifugation at 12,000×g for 20 minutes. Extracts were then ultracentrifuged at 109,000 rcf (max) for 30 minutes. Small, glassy pellets were resuspended in TEMB. *H. ochraceum* shells were further purified with agarose gel electrophoresis as previously described[19] or with sucrose density gradient ultracentrifugation using step gradients of 20%-70% sucrose in TEMB with 5% step size.

Insertion of Stop Codons.

Inverse PCR mutagenesis was used to insert a single stop codon (TGA, TAA, or TAG) within the first 10 base triplets in each gene of the *H. ochraceum* construct. These knock-out mutations were expressed and purified as described for the standard construct.

Analysis and Quantitation of Shells and Shell Proteins.

Trypsin digests and mass spectrometry to identify *H. ochraceum* shell proteins from SDS-PAGE were performed by Stanford University Protein and Nucleic Acid Facility. Amino acid analysis of purified shell proteins and shells was performed by the U.C. Davis Genome Center Proteomics Core Facility. Deconvolution of shell protein amino acid analysis is further described. Estimates of protein mass ratios from gel densitometry were made using Image Lab software (Bio-Rad). Comparisons of protein masses from purified shells and between purified shells and quantitated shell proteins were made with multiple SDS-PAGE samples over 20-fold ranges of concentration, and uncertainties are estimated to be ~20%.

Transmission Electron Microscopy and Gold Labeling.

Shells and shell proteins were negatively stained on formvar/carbon coated copper grids (Electron Microscopy Sciences, # FCF300-Cu) by floating the grids on a 4 μL sample droplet for 4 minutes, drying, and then floating the grid on a 4 μL droplet of 1% ammonium molybdate for 40 seconds. For immunogold labeling, antibodies were prepared by PRF & L (*Canadensis*, PA) using BMC-T(5812) protein purified by SDS-PAGE as the antigen. TEM Grids were floated on the BMC sample for 5 minutes, floated on 1% BSA with 0.05% Tween-20 in PBS buffer for 6 minutes to block, then floated at room temperature for 2 hours on primary antibody solution in a humid chamber. Grids were washed with 1% BSA in PBS and floated on 5 nm gold-labeled goat anti-rabbit (Abcam, # ab27235, 1 μg/mL in BSA/PBS) for 40 minutes then washed with PBS/BSA. After rinsing with water for 3×1 minutes, grids were stained by floating for 40 seconds on 1% uranyl acetate in water. Images were collected on Tecnai 12 and JEOL 1200EX TEM instruments.

Dynamic Light Scattering.

Shells were pelleted in a Ti-70 rotor at 42,000 rpm for 2 h and resuspended in 10 mM Tris pH 7.4. Shells at an A280 of 0.6 were measured in a Protein Solutions Dynapro dynamic light scattering instrument with an acquisition time of 5 s, averaging 10 acquisitions at a constant temperature of 25 C. The shell radius was calculated assuming a globular particle shape.

Encapsulation Experiments.

The constructs indicated in FIG. 6 were placed under control of the T7 promoter in the pCOLA-DUET-1 vector for coexpression with shell proteins in pET-11. Protein expression and shell purification was performed as described for shells. Western blots were performed with 1:3000 dilution of anti-GFP polyclonal antibody (Life Technologies) and detected with AP-conjugated anti-rabbit (Sigma) and BCIP/NBT substrate.

Our model suggests that two types of BMC-T units may have distinct roles in producing the icosahedral assembly. BMC-P units, in contrast, did not appear to be necessary for the formation of shells in this system, although they are expected to be a necessary component of the diffusive barrier needed for metabolic function.[26] The defined composition of these shells should enable systematic perturbations to further understand structural and functional roles of each unit.

This shell construct was produced synthetically, retaining no information about gene order, genome context, or potential biological function of the putative *H. ochraceum* microcompartment. Using a logic designed to produce expression levels that mimic protein abundances in natural BMCs, the shell proteins were assembled into a new operon. This strategy made it possible to consider a diverse set of potential new shell building blocks. It remains unknown whether the structure and properties of the compartments are recapitulated in a native *H. ochraceum* microcompartment in vivo. Nevertheless, the remarkable properties of these synthetic shells relative to results from the more familiar carboxysome, pdu, and eut systems illustrates the importance of sampling from the diversity of BMCs now apparent in sequenced genomes. Many of the BMC systems included in our screen were of unknown function and BMCs could be identified only by the presence of genes encoding shell proteins. Our results expand the range of known BMC shell morphologies and suggest that the many remaining BMC clusters of unknown function may offer new surprises and insights into BMC function and assembly Example 8: Targeting Proteins for Encapsulation for Biofuel Production Synthetic microcompartment shells containing Rubisco could be expressed in the chloroplast of tobacco or camelina to increase photosynthetic efficiency for agricultural or biofuel production.

Alternatively, the microcompartment shells could be designed to house enzymes for the production of high energy molecules (CoA derivative) or chemical feedstocks (isoprene) and expressed in plants to produce large quantities of desired product in crop or mass cultured species Example 9: Using Self-Assembling Microcompartment Proteins to Form Sheets BMC shell proteins may also be used to produce self-assembling sheets that may be used for a variety of applications, including fabrication, production of molecular sieves, or creation of an ordered system with properties similar to those of liquid crystal. We observed self-assembly into protein layers of shell proteins from *H. ochraceum*. The hexamer protein (single pfam00936 domain) from *H. ochraceum* was expressed in *E. coli* and purified in a single extraction step with the BPER-2 reagent (Pierce). TEM images of this pure sample on Formvar carbon grids showed large sheets of closely-packed hexagonal proteins as shown in FIG. 10A The microcompartment shell system described here differs substantially from natural BMC particles that have been isolated previously, with a much smaller and more uniform size.[11-13, 20, 21, 25] The size and uniformity enabled the construction of a structural model that includes 260 hexagonal units total and 13 hexagonal units per icosahedral face (FIG. 5C). A further quantitative analysis of shell composition led to a model for shell construction that suggests specific structural roles for the four gene products. Our results suggest that the BMC-H units readily self-assemble to form sheets as in FIG. 4A and that BMC-T units may serve to produce the curvature needed for shells and to produce the binding sites for pentameric vertex assemblies.

It may be possible to control the assembly into layers by altering the conditions. At this stage, however, it is known is that the layers form spontaneously under the given conditions as described in Example 7. It appears that in solution, the layers are constantly forming and dissociating because the pure protein solution has an iridescent and swirling appearance that is reminiscent of liquid crystal. Future experiments may be carried out to test or optimize what the requirements are in terms of protein concentrations, buffer conditions, temperature, etc.

Example 10: Evidence of Icosahedral Construction

We also tested whether or not the angles between gold particles in TEM images reflect possible icosahedral symmetry. Angles were measured in images of shells that were treated with gold-labeled BMC-T(5812) antibodies. The angles between gold particles were determined as follows: Gold particles were selected only if the gold was positioned outside of the shell outline in TEM images. As shown in the example of FIG. 16B, a circle was drawn around the shell outline and used to define a center point. Angles were defined as gold-center-gold and all possible angles between gold particles were measured. These angles (n=58) are plotted in the histogram. In FIG. 16C, the expectations for two types of random distributions of angles are shown on the histogram. We have illustrated two limiting cases that represent random distributions of points placed either on the circumference of a two-dimensional circle or on the surface of a three-dimensional sphere.

A dashed line is shown that corresponds to the histogram expected for 58 measurements of angles between hypothetical points that are randomly positioned on a two-dimensional circle. These hypothetical points on a circle represent the expectations for a random distribution of angles in the case where our gold particles were perfectly selected such that the antibody binding sites were positioned exactly on the outermost edge of the shells. If the gold particles were perfectly selected in this way, they would correspond to points on a circle, and the random distribution is expected to be flat, as seen in the dashed line.

However, the selection of gold particles is likely to be imperfect because of the ~7 nm length between the antibody binding site and the difficulty in knowing the site of binding of the antibody on the shell. The resulting imperfect measurements are expected to be intermediate between the above two-dimensional model and the distribution of angles between gold particles positioned on a sphere that is projected into two dimensions. The solid line illustrates the shape of the histogram expected for 58 measurements of angles between particles positioned on a three-dimensional sphere that is projected into a two-dimensional image. This distribution is curved, because the surface area of the sphere at an angle of 90° is much larger than the surface area of the sphere at an angle near 180°. As an example of this phenomenon, there are many different ways to stand at the equator of the earth (90°) but only one way to stand on the north pole (180°).

In contrast to both types of random distributions, the observed distribution of angles, shown in the histogram bars, suggests a higher representation of 120°-140° and 160°-180° angles, as would be expected for vertices of icosahedral particles projected onto two dimensions. Examples of these angles that are expected to be more highly represented in icosahedral particles are shown in FIG. 16D.

Example 11: Stoichiometry of Shell Proteins from Amino Acid Analysis Performed on Purified Shells Amino acid analysis was performed on shells purified by multiple passages over sucrose gradients. The resulting shell preparation was similar to (but more pure than) that shown in FIG. 2 in the manuscript under the heading "Sucrose purification". Purity is estimated at >90%, and the concentration of any single impurity was low.

Amino acid analysis of these shells yielded values for concentrations of 14 amino acid groups: Asp+Asn, Gln+Glu, Thr, Ser, Pro, Gly, Ala, Val, Ile, Leu, Tyr, Phe, His, Lys, and Arg. Data for Lys were not considered further because they showed large deviations in concentration values relative to the other amino acids in tests with the individual purified shell proteins.

Values for the 14 amino acid groups were used to calculate concentrations of shell units as in the example in the table below. This example does not include BMC-P, but these units are included in analyses described on the next page.

The first column of values in the table corresponds to the experimentally determined molar concentration of the amino acid group in the sample of purified shells. These were calculated directly from the results of amino acid analysis. The next four columns ("Number of each amino acid in sequence") correspond to the count of each amino acid in the primary sequence of the given polypeptide. These values were used to calculate the number of each amino acid that would be expected in a shell unit of 8:1:1:1 molar ratio. For example, 87 Asn+Asp residues were calculated for an 8:1:1:1 shell unit by adding (8×6 in BMC-H)+(1×1 in BMC-T(5816))+(1×1 in BMC-T(3341))+(1×1 in BMC-T (5812)).

In the right-most column of the table, the effective concentration of shell units is calculated by using the concentration of amino acid from column 1 and the number of amino acids in an 8:1:1:1 shell unit. For example, the 83.2 µM concentration of Asn/Asp residues was divided by the expected 87 Asn/Asp residues in a single 8:1:1:1 shell unit to give a concentration of shell units in the sample of 0.957. This column thus gives a calculated concentration of shell units obtained from the data for each of the 14 amino acid groups.

TABLE 2

|  | Concentration of amino acid in shells, µM | Number of each amino acid in sequence | | | | Number per shell unit using 8:1:1:1 molar ratio | Concentration of shell units using 8:1:1:1 molar ratio |
| --- | --- | --- | --- | --- | --- | --- | --- |
|  |  | BMC-H | BMC-T (5816) | BMC-T (3341) | BMC-T (5812) |  |  |
| Asn/Asp | 83.2 | 6 | 12 | 14 | 13 | 87 | 0.957 |
| Thr | 52.0 | 4 | 11 | 8 | 9 | 60 | 0.867 |
| Ser | 34.2 | 1 | 9 | 6 | 9 | 32 | 1.069 |
| Gln/Glu | 118.8 | 8 | 30 | 29 | 22 | 145 | 0.820 |
| Pro | 59.4 | 4 | 9 | 7 | 11 | 59 | 1.007 |
| Gly | 137.2 | 12 | 15 | 21 | 13 | 145 | 0.947 |
| Ala | 209.3 | 19 | 33 | 35 | 36 | 256 | 0.817 |
| Val | 143.2 | 17 | 18 | 13 | 16 | 183 | 0.783 |
| Ile | 41.6 | 3 | 15 | 12 | 10 | 61 | 0.682 |
| Leu | 72.8 | 4 | 20 | 23 | 25 | 100 | 0.728 |
| Tyr | 19.4 | 2 | 6 | 4 | 1 | 27 | 0.719 |
| Phe | 18.2 | 1 | 7 | 4 | 6 | 25 | 0.728 |
| His | 23.2 | 2 | 4 | 5 | 3 | 28 | 0.829 |
| Arg | 88.8 | 6 | 12 | 13 | 16 | 89 | 0.998 |

We have an expectation that if the molar ratio of 8:1:1:1 is accurate, then the calculated molarity of shell units (the right-most column) should be similar among each of the 14 different amino acid measurements. Similarly, if the molar ratio is far off from the true value, then different amino acids will be differentially represented and the calculated molarity of shell units will vary more substantially among the amino acids. While some amino acids are similarly represented among BMC-H and the BMC-T proteins, other amino acids such as Gln/Glu and Leu, have 2-fold to 6-fold differences in abundances and these variations will significantly affect the calculated molarities leading to wider variation among the amino acids if the molar ratio is inaccurate We thus performed the calculations for a wide range of possible molar ratios, ranging from 1:1:1:1 to 30:1:1:1. To determine the degree of variation in calculated molarities of shell units among the different amino acids, we calculated standard deviations for the values in the right-most column in the table. The standard deviations divided by the means are plotted in red below for molar ratios ranging from 1:1:1:1 to 30:1:1:1. In these plots, the smallest variation was found with a molar ratio of 8:1:1:1, consistent with data from gel densitometry as described herein.

The data plotted in FIG. 17A are those calculated with simple ratios of shell units as given in the example table on the prior page. We also plotted (FIG. 17B) the results when exact stoichiometries for models 1-5 in the main text are used in the calculations, both with and without BMC-P subunits. Values in green include BMC-P, while values in orange do not include BMC-P. The variation is slightly lower when BMC-P subunits are included, but the differences are small and cannot rule out either the presence or absence of pentameric subunits.

Example 12: Measurement of Thickness of Shells in TEM Images

Shell thicknesses were measured in TEM images that were collected as described in Materials and Methods. Measurements from 31 different shells were taken from TEM images collected on two different instruments and from two different shell preparations. The distribution of thickness values is shown in FIG. 18.

The distribution of values suggests that the shell thicknesses are greater than those expected for a single-layered shell. Measurements from crystal structures of BMC-H homologs give a range of about 2.9-3.3 nm (e.g., pdb code 2EWH). However, there is substantial uncertainty in measuring these values from TEM images, including concerns about resolution, staining, and the effects of the drying process.

Example 13: Co-Purification of GFP-Labeled Constructs with Microcompartment Shells Following co-expression of shell proteins (in the pET-11 vector) with the GFP fusions shown in FIG. 4 (in the pCOLA-DUET-1 vector) in *E. coli* BL21-CodonPlus(DE3)-RIL cells, the purification procedure described in Materials and Methods was followed. Following ultracentrifugation, the supernatants were separated with sucrose step gradients (20%-70% sucrose in TEMB buffer with 5% step sizes). BMC-containing fractions were pooled and concentrated by ultracentrifugation, then placed over a second sucrose gradient. Shown in FIGS. 19A and 19B are SDS-PAGE and western blotting of the fractions collected from this purification step.

REFERENCES

1. Kerfeld, C. A., S. Heinhorst, and G. C. Cannon, *Bacterial Microcompartments*. Annual Review of Microbiology, 2010. 64: p. 391-408.
2. Cheng, S., et al., *The PduQ enzyme is an alcohol dehydrogenase used to recycle NAD(+) internally within the Pdu microcompartment of Salmonella enterica*. PLoS One, 2012. 7: p. e47144.
3. Huseby, D. L. and J. R. Roth, *Evidence that a metabolic microcompartment contains and recycles private cofactor pools*. Journal of Bacteriology, 2013.
4. Dou, Z., et al., *CO2 fixation kinetics of Halothiobacilius neapolitanus mutant carboxysomes lacking carbonic anhydrase suggest the shell acts as a diffusional barrier for CO2*. Journal of Biological Chemistry, 2008. 283: p. 10377-10384.
5. Price, G. D., et al., *The cyanobacterial CCM as a source of genes for improving photosynthetic CO2 fixation in crop species*. Journal of Experimental Botany, 2013. 64: p. 753-768.
6. Zarzycki, J., et al., *Cyanobacterial-based approaches to improving photosynthesis in plants*. Journal of Experimental Botany, 2013. 64: p. 787-798.
7. Agapakis, C. M., P. M. Boyle, and P. A. Silver, *Natural strategies for the spatial optimization of metabolism in synthetic biology*. Nature Chemical Biology, 2012. 8: p. 527-535.
8. Chen, A. H. and P. A. Silver, *Designing biological compartmentalization*. Trends in Cell Biology, 2012. 22: p. 662-670.
9. Howorka, S., *Rationally engineering natural protein assemblies in nanobiotechnology*. Current Opinion in Biotechnology, 2011. 22: p. 485-491.
10. Doll, T. A. P. F., et al., *Nanoscale assemblies and their biomedical applications*. Journal of the Royal Society Interface, 2013. 10: p. 20120740.
11. Bonacci, W., et al., *Modularity of a carbon-fixing protein organelle*. Proceedings of the National Academy of Sciences of the United States of America, 2012. 109: p. 478-483.
12. Choudhary, S., et al., *Engineered protein nano-compartments for targeted enzyme localization*. PLoS One, 2012. 7: p. e33342.
13. Parsons, J. B., et al., *Synthesis of empty bacterial microcompartments, directed organelle protein incorporation, and evidence of filament-associated organelle movement*. Molecular Cell, 2010. 38: p. 305-315.
14. Ivanova, N., et al., *Complete genome sequence of Haliangium ochraceum type strain (SMP-2)*. Standards in Genomic Sciences, 2010. 2: p. 96-106.
15. Punta, M., et al., *The Pfam protein families database*. Nucleic Acids Research, 2012. 40: p. D290-D301.
16. Kerfeld, C. A., et al., *Protein structures forming the shell of primitive bacterial organelles*. Science, 2005. 309: p. 936-938.
17. Kinney, J. N., S. D. Axen, and C. A. Kerfeld, *Comparative analysis of carboxysome shell proteins*. Photosynthetic Research, 2011. 109: p. 21-32.
18. Yeates, T. O., C. S. Crowley, and S. Tanaka, *Bacterial microcompartment organelles: Protein shell structure and evolution*. Annual Review of Biophysics 2010. 39: p. 185-205.
19. Cannon, G. C. and J. M. Shively, *Characterization of a homogeneous preparation of carboxysomes from Thiobacillus neapolitanus*. Archives of Microbiology, 1983. 134: p. 52-59.
20. Havemann, G. D. and T. A. Bobik, *Protein content of polyhedral organelles involved in coenzyme B12-dependent degradation of 1,2-propanediol in Salmonella enterica serovar typhimurium LT2*. Journal of Bacteriology, 2003. 185: p. 5086-5095.
21. Roberts, E. W., et al., *Isolation and characterization of the prochlorococcus carboxysome reveal the presence of the novel shell protein CsoS1D*. Journal of Bacteriology, 2012. 194: p. 787-795.
22. Klein, M. G., et al., *Identification and structural analysis of a novel carboxysome shell protein with implications for metabolite transport*. Journal of Molecular Biology, 2009. 392: p. 319-333.
23. Cai, F., et al., *The structure of CcmP, a tandem bacterial microcompartment domain protein from the β-carboxysome forms a subcompartment within a microcompartment*. 2013. 288: p. 16055-16063.
24. Tanaka, S., et al., *Atomic-level models of the bacterial carboxysome shell*. Science, 2008. 319: p. 1083-1086.
25. So, A. K. C., et al., *A novel evolutionary lineage of carbonic anhydrase (ε class) is a component of the carboxysome shell*. Journal of Bacteriology, 2004. 186: p. 623-630.
26. Cai, F., et al., *The pentameric vertex proteins are necessary for the icosahedral carboxysome shell to function as a CO2 leakage barrier*. PLoS One, 2009. 4: p. e7521.
27. Caspar, D. L. D. and A. Klug, *Physical principles in the construction of regular viruses*. Cold Spring Harbor Symposia on Quantitative Biology, 1962. 27: p. 1-24.
28. Pang, A., M. J. Warren, and R. W. Pickersgill, *Structure of PduT, a trimeric bacterial microcompartment protein with a 4Fe-4S cluster-binding site*. Acta Crystallographica, Section D, 2011. 67: p. 91-96.
29. Crowley, C. S., et al., *PduT C38S mutant from Salmonella enterica Typhimurium*. Journal of Biological Chemistry, 2010. 285: p. 37838-37846.
30. Sagermann, M., A. Ohtaki, and K. Nikolakakis, *Crystal structure of the EutL shell protein of the ethanolamine ammonia lyase microcompartment*. Proceedings of the National Academy of Sciences of the United States of America, 2009. 106: p. 8883-8887.
31. Samborska, B. and M. S. Kimber, *A dodecameric CcmK2 structure suggests β-carboxysomal shell facets have a double-layered organization*. Structure, 2012. 20: p. 1353-1362.
32. Kinney, J. N., et al., *Elucidating essential role of conserved carboxysomal protein CcmN reveals common feature of bacterial microcompartment assembly*. Journal of Biological Chemistry, 2012. 287: p. 17729-17736.
33. Fan, C., et al., *Short N-terminal sequences package proteins into bacterial microcompartments*. Proceedings of the National Academy of Sciences of the United States of America, 2010. 107: p. 7509-7514.
34. Thiennimitr, P., et al., *Intestinal inflammation allows Salmonella to use ethanolamine to compete with the microbiota*. Proceedings of the National Academy of Sciences of the United States of America, 2011. 108: p. 17480-17485.

The above examples are provided to illustrate the invention but not to limit its scope. Other variants of the invention will be readily apparent to one of ordinary skill in the art and are encompassed by the appended claims. All publications, references, databases, and patents cited herein are hereby incorporated by reference for all purposes.

What is claimed is:

1. A method for producing bacterial microcompartments in a prokaryotic host organism, said method comprising:
introducing into a prokaryotic host organism an expression vector comprising a heterologous nucleotide sequence comprising (a) an operably linked promoter that drives expression in the organism; (b) a first ribosomal binding site sequence that provides a first level of translation initiation and controls expression efficiency in the host organism of a first bacterial microcompartment gene that encodes a first protein comprising a single BMC domain, and (c) a second ribosomal binding site sequence different from the first ribosomal binding site sequence, wherein the second ribosomal binding site sequence provides a second level of translation initiation and controls expression efficiency in the host organism of each of three variants of a second bacterial microcompartment gene that encodes a second protein comprising two BMC domains derived from a bacteria for producing a bacterial microcompartment; and
incubating the prokaryotic host organism to produce the bacterial microcompartments,
wherein the second level of translation initiation is lower than the first level of translation initiation.

2. The method of claim 1, wherein the host organism is a bacterial cell.

3. The method of claim 2, wherein the host organism is *E. coli* or *B. subtilis*.

4. The method of claim 1, wherein the expression vector comprises a polynucleotide comprising one or more hexamer genes, tandem domains, and pentamers.

5. The method of claim 1, wherein the first and second bacterial microcompartment genes are heterologous for the host organism.

6. The method of claim 1, wherein the promoter is an inducible promoter.

7. The method of claim 1, wherein the promoter is contiguous to the first or second bacterial microcompartment gene.

8. The method of claim 1, wherein the first or second ribosomal binding site sequence is derived from *Escherichia coli* or *Halothiobacillus neapolitanus*.

9. The method of claim 1, wherein the first or second bacterial microcompartment gene encodes shell proteins derived from *Haliangium ochraceum*, *Mycobacterium smegmatis*, or *Thermosynechococcus elongatus*.

10. The method of claim 1, wherein the expression vector further comprises a selectable marker gene.

11. The method of claim 10, wherein the selectable marker gene is selected from a group consisting of an antibiotic resistance gene, β-galactosidase gene, and fluorescent protein gene.

12. The method of claim 1, wherein the expression vector further comprises a polynucleotide encoding an encapsulating targeting peptide linked to a polynucleotide encoding a protein that provides enhanced metabolic activity in the host organism.

13. The method of claim 12, wherein the encapsulating targeting peptide is located in the C-terminal or N-terminal region of the protein that provides enhanced metabolic activity in the host organism.

14. The method of claim 12, wherein the enhanced metabolic activity comprises $CO_2$ fixation or alcohol breakdown.

15. The method of claim 1, wherein the first protein and the three variants of the second protein are present in the bacterial microcompartment at a mass ratio of 3:1:1:1.

16. The method of claim 1, wherein the first protein and the three variants of the second protein are present in the bacterial microcompartment at a molar ratio of 7:1:1:1.

17. The method of claim 1, wherein the first protein and the three variants of the second protein are present in the bacterial microcompartment at a molar ratio of 8:1:1:1.

18. The method of claim 1, wherein the expression vector further comprises a third ribosomal binding site sequence that provides a third level of translation initiation and controls expression efficiency in the host organism of a third bacterial microcompartment gene, wherein the third level of translation initiation is different from the first or second levels of translation initiation.

\* \* \* \* \*

SEQUENCE LISTING

<160> NUMBER OF SEQ ID NOS: 58

<210> SEQ ID NO 1
<211> LENGTH: 25
<212> TYPE: DNA
<213> ORGANISM: Escherichia coli

<400> SEQUENCE: 1
tttagagaaa gaggagaaat actag                                            25

<210> SEQ ID NO 2
<211> LENGTH: 28
<212> TYPE: DNA
<213> ORGANISM: Escherichia coli

<400> SEQUENCE: 2
tttagagatt aaagaggaga aatactag                                         28

<210> SEQ ID NO 3
<211> LENGTH: 27
<212> TYPE: DNA
<213> ORGANISM: Escherichia coli

<400> SEQUENCE: 3
tttagagtca cacaggaaac ctactag                                          27

<210> SEQ ID NO 4
<211> LENGTH: 34
<212> TYPE: DNA
<213> ORGANISM: Halothiobacillus neapolitanus

<400> SEQUENCE: 4
gattttgaat gagtctttat tgaggagaga agaa                                  34

<210> SEQ ID NO 5
<211> LENGTH: 255
<212> TYPE: DNA
<213> ORGANISM: Verminephrobacter eiseniae

<400> SEQUENCE: 5
atgactgcat acatcaatca ggaagcagcg gcaaagctcg atgaagtctt tccccttgca      60
gaattggcgc tcaaggccta tgggccagag tttcagggtg aactcagcct gctgacacac     120
tctgaaaatt cgacctatct ggtgaacgca ttttcagggc agcgcttcgt aatgcgcgtg     180
catcgtgcgc actaccacag cagaacggcc attgaaagcg agttggcatg gctggatgca     240
ctggccgatg aaggc                                                      255

<210> SEQ ID NO 6
<211> LENGTH: 99
<212> TYPE: PRT
<213> ORGANISM: Haliangium ochraceum

<400> SEQUENCE: 6

Met Ala Asp Ala Leu Gly Met Ile Glu Val Arg Gly Phe Val Gly Met
1               5                   10                  15

Val Glu Ala Ala Asp Ala Met Val Lys Ala Ala Lys Val Glu Leu Ile
            20                  25                  30

Gly Tyr Glu Lys Thr Gly Gly Gly Tyr Val Thr Ala Val Val Arg Gly
        35                  40                  45

```
Asp Val Ala Ala Val Lys Ala Ala Thr Glu Ala Gly Gln Arg Ala Ala
        50                  55                  60

Glu Arg Val Gly Glu Val Ala Val His Val Ile Pro Arg Pro His
 65                  70                  75                  80

Val Asn Val Asp Ala Ala Leu Pro Leu Gly Arg Thr Pro Gly Met Asp
                85                  90                  95

Lys Ser Ala

<210> SEQ ID NO 7
<211> LENGTH: 300
<212> TYPE: DNA
<213> ORGANISM: Artificial Sequence
<220> FEATURE:
<223> OTHER INFORMATION: Synthetic DNA sequence selected to encode the
      protein sequence of SEQ ID NO:6 while utilizing high-frequency
      codons from E. coli, the host organism; YP_003270184

<400> SEQUENCE: 7
atggcggacg cactgggtat gattgaagtt cgtggttttg ttggtatggt ggaagcggcg     60
gatgctatgg tgaaagcggc taaagttgaa ctgattggtt atgaaaaaac cggcggtggc    120
tacgtgacgg cagtggttcg tggtgatgtc gcagcagtta aggcagctac cgaagccggt    180
cagcgtgcag cagaacgtgt tggtgaagtc gtggcagttc atgtcatccc gcgtccgcac    240
gtgaacgttg atgcagctct gccgctgggt cgtacgccgg gtatggacaa aagcgcgtaa    300

<210> SEQ ID NO 8
<211> LENGTH: 205
<212> TYPE: PRT
<213> ORGANISM: Haliangium ochraceum

<400> SEQUENCE: 8

Met Asp His Ala Pro Glu Arg Phe Asp Ala Thr Pro Pro Ala Gly Glu
 1               5                  10                  15

Pro Asp Arg Pro Ala Leu Gly Val Leu Glu Leu Thr Ser Ile Ala Arg
                20                  25                  30

Gly Ile Thr Val Ala Asp Ala Ala Leu Lys Arg Ala Pro Ser Leu Leu
            35                  40                  45

Leu Met Ser Arg Pro Val Ser Ser Gly Lys His Leu Leu Met Met Arg
        50                  55                  60

Gly Gln Val Ala Glu Val Glu Ser Met Ile Ala Ala Arg Glu Ile
 65                  70                  75                  80

Ala Gly Ala Gly Ser Gly Ala Leu Leu Asp Glu Leu Glu Leu Pro Tyr
                85                  90                  95

Ala His Glu Gln Leu Trp Arg Phe Leu Asp Ala Pro Val Val Ala Asp
            100                 105                 110

Ala Trp Glu Glu Asp Thr Glu Ser Val Ile Val Glu Thr Ala Thr
        115                 120                 125

Val Cys Ala Ala Ile Asp Ser Ala Asp Ala Leu Lys Thr Ala Pro
        130                 135                 140

Val Val Leu Arg Asp Met Arg Leu Ala Ile Gly Ile Ala Gly Lys Ala
145                 150                 155                 160

Phe Phe Thr Leu Thr Gly Glu Leu Ala Asp Val Glu Ala Ala Ala Glu
                165                 170                 175

Val Val Arg Glu Arg Cys Gly Ala Arg Leu Leu Glu Leu Ala Cys Ile
            180                 185                 190
```

Ala Arg Pro Val Asp Glu Leu Arg Gly Arg Leu Phe Phe
        195                 200                 205

<210> SEQ ID NO 9
<211> LENGTH: 618
<212> TYPE: DNA
<213> ORGANISM: Artificial Sequence
<220> FEATURE:
<223> OTHER INFORMATION: Synthetic DNA sequence selected to encode the
      protein sequence of SEQ ID NO:8 while utilizing high-frequency
      codons from E. coli, the host organism; YP_003270181

<400> SEQUENCE: 9
atggaccacg ctccggaacg ctttgatgcg accccgccgg caggtgaacc ggaccgcccg      60
gcactgggtg tgctggaact gacctcaatt gctcgtggta tcaccgttgc ggatgcggcc     120
ctgaaacgtg caccgagtct gctgctgatg tcccgcccgg tcagctctgg caagcatctg     180
ctgatgatgc gtggccaggt ggcagaagtt gaagaatcaa tgattgcagc tcgcgaaatc     240
gctggtgcag gttcgggtgc tctgctggat gaactggaac tgccgtatgc gcacgaacaa     300
ctgtggcgct ttctggacgc accggtggtt gcagatgcat gggaagaaga caccgaaagc     360
gtcattatcg tggaaaccgc gacggtgtgc gcggccattg atagtgccga cgcagctctg     420
aaaacggcac cggtcgtgct gcgtgatatg cgcctggcca ttggtatcgc tggcaaggcg     480
tttttcaccc tgacgggtga actggcagac gtggaagcgg ccgcagaagt tgtccgtgaa     540
cgttgcggtg cacgtctgct ggaactggca tgtatcgcac gcccggttga tgaactgcgt     600
ggccgcctgt ttttctaa                                                  618

<210> SEQ ID NO 10
<211> LENGTH: 206
<212> TYPE: PRT
<213> ORGANISM: Haliangium ochraceum

<400> SEQUENCE: 10

Met Glu Leu Arg Ala Tyr Thr Val Leu Asp Ala Leu Gln Pro Gln Leu
1               5                   10                  15

Val Ala Phe Leu Gln Thr Val Ser Thr Gly Phe Met Pro Met Glu Gln
            20                  25                  30

Gln Ala Ser Val Leu Val Glu Ile Ala Pro Gly Ile Ala Val Asn Gln
        35                  40                  45

Leu Thr Asp Ala Ala Leu Lys Ala Thr Arg Cys Gln Pro Gly Leu Gln
    50                  55                  60

Ile Val Glu Arg Ala Tyr Gly Leu Ile Glu Met His Asp Asp Asp Gln
65                  70                  75                  80

Gly Gln Val Arg Ala Ala Gly Asp Ala Met Leu Ala His Leu Gly Ala
                85                  90                  95

Arg Glu Ala Asp Arg Leu Ala Pro Arg Val Val Ser Ser Gln Ile Ile
            100                 105                 110

Thr Gly Ile Asp Gly His Gln Ser Gln Leu Ile Asn Arg Met Arg His
        115                 120                 125

Gly Asp Met Ile Gln Ala Gly Gln Thr Leu Tyr Ile Leu Glu Val His
    130                 135                 140

Pro Ala Gly Tyr Ala Ala Leu Ala Ala Asn Glu Ala Glu Lys Ala Ala
145                 150                 155                 160

Pro Ile Lys Leu Leu Glu Val Val Thr Phe Gly Ala Phe Gly Arg Leu
                165                 170                 175

Trp Leu Gly Gly Gly Glu Ala Glu Ile Ala Glu Ala Ala Arg Ala Ala
            180                 185                 190

Glu Gly Ala Leu Ala Gly Leu Ser Gly Arg Asp Asn Arg Gly
        195                 200                 205

<210> SEQ ID NO 11
<211> LENGTH: 621
<212> TYPE: DNA
<213> ORGANISM: Artificial Sequence
<220> FEATURE:
<223> OTHER INFORMATION: Synthetic DNA sequence selected to encode the
      protein sequence of SEQ ID NO:10 while utilizing high-frequency
      codons from E. coli, the host organism; YP_003267736

<400> SEQUENCE: 11
atggaactgc gtgcttatac ggtcctggat gccctgcagc cgcaactggt cgcctttctg        60
caaacggtgt caacgggttt catgccgatg aacagcaag cgagcgttct ggtcgaaatt       120
gcaccgggta tcgctgtcaa ccagctgacc gacgcagcac tgaaagcaac gcgttgccag      180
ccgggtctgc aaattgtgga acgtgcgtat ggcctgatcg aaatgcatga tgacgatcag      240
ggtcaagttc gtgcagctgg tgacgcaatg ctggcacacc tgggtgcacg tgaagctgat      300
cgtctggcac gcgtgtggt tagctctcag attatcaccg gtattgacgg ccatcagagt      360
caactgatca accgtatgcg ccacggtgat atgattcagg caggccaaac gctgtatatc      420
ctggaagttc atccggcagg ttacgcagca ctggcagcta tgaagccga aaaagcggcc       480 ccgattaagc tgctggaagt cgtgacccttt ggtgcattcg gtcgtctgtg ctgggtggt      540 ggtgaagcag aaatcgcaga agcagctcgt gcggcagaag gtgcactggc tggtctgtcc      600
ggccgtgata atcgcggcta a                                                 621

<210> SEQ ID NO 12
<211> LENGTH: 212
<212> TYPE: PRT
<213> ORGANISM: Haliangium ochraceum

<400> SEQUENCE: 12

Met Ser Ile Thr Leu Arg Thr Tyr Ile Phe Leu Asp Ala Leu Gln Pro
1               5                   10                  15

Gln Leu Ala Thr Phe Ile Gly Lys Thr Ala Arg Gly Phe Leu Pro Val
            20                  25                  30

Pro Gly Gln Ala Ser Leu Trp Val Glu Ile Ala Pro Gly Ile Ala Ile
        35                  40                  45

Asn Arg Val Thr Asp Ala Ala Leu Lys Ala Thr Lys Val Gln Pro Ala
    50                  55                  60

Val Gln Val Val Glu Arg Ala Tyr Gly Leu Leu Glu Val His His Phe
65                  70                  75                  80

Asp Gln Gly Glu Val Leu Ala Ala Gly Ser Thr Ile Leu Asp Lys Leu
                85                  90                  95

Glu Val Arg Glu Glu Gly Arg Leu Lys Pro Gln Val Met Thr His Gln
            100                 105                 110

Ile Ile Arg Ala Val Glu Ala Tyr Gln Thr Gln Ile Ile Asn Arg Asn
        115                 120                 125

Ser Gln Gly Met Met Ile Leu Pro Gly Glu Ser Leu Phe Ile Leu Glu
    130                 135                 140

Thr Gln Pro Ala Gly Tyr Ala Val Leu Ala Ala Asn Glu Ala Glu Lys
145                 150                 155                 160

```
Ala Ala Asn Val His Leu Val Asn Val Thr Pro Tyr Gly Ala Phe Gly
            165                 170                 175

Arg Leu Tyr Leu Ala Gly Ser Glu Ala Glu Ile Asp Ala Ala Ala Glu
        180                 185                 190

Ala Ala Glu Ala Ala Ile Arg Ser Val Ser Gly Val Ala Gln Glu Ser
    195                 200                 205

Phe Arg Asp Arg
    210

<210> SEQ ID NO 13
<211> LENGTH: 639
<212> TYPE: DNA
<213> ORGANISM: Artificial
<220> FEATURE:
<223> OTHER INFORMATION: Synthetic DNA sequence selected to encode the
      protein sequence of SEQ ID NO:12 while utilizing high-frequency
      codons from E. coli, the host organism; YP_003270185

<400> SEQUENCE: 13
atgtcaatca ccctgcgcac ctatatcttt ctggacgccc tgcaaccgca actggcaacc      60
ttcatcggca aaacggctcg tggcttcctg ccggtcccgg gtcaggcaag cctgtgggtg     120
gaaattgctc cgggtattgc gatcaaccgt gtgaccgatg cggccctgaa agctacgaag     180
gtgcagccgg cggttcaagt ggttgaacgc gcgtatggcc tgctggaagt tcatcacttc     240
gatcagggcg aagtcctggc agctggtagt accatcctgg acaaactgga agttcgtgaa     300
gaaggtcgcc tgaagccgca ggtgatgacc atcaaattat ccgtgctgt tgaagcgtat      360 cagacgcaaa ttatcaaccg caatagtcag ggcatgatga ttctgccggg tgaatccctg     420
tttatcctgg aaacccaacc ggcaggttac gcagtcctgg cagccaatga agccgaaaaa     480
gcagctaacg ttcacctggt caatgtgacg ccgtatggcg cattcggtcg tctgtacctg     540
gccggctcag aagcagaaat tgatgcggcc gcagaagctg cggaagccgc aatccgcagc     600
gtttctggtg tcgcgcagga atcgtttcgt gaccgctaa                          639

<210> SEQ ID NO 14
<211> LENGTH: 92
<212> TYPE: PRT
<213> ORGANISM: Haliangium ochraceum

<400> SEQUENCE: 14

Met Tyr Leu Gly Arg Val Ile Gly Thr Val Val Ala Glu Arg Lys Val
1               5                   10                  15

Ala Gly Leu Glu Gly Ala Lys Leu Leu Val Gln Pro Leu Asp Asp
            20                  25                  30

Ala Leu Ser Pro Val Gly Gly Val Gln Ala Ala Val Asp Thr Val Gln
        35                  40                  45

Ala Gly Pro Asp Asp Leu Val Tyr Leu Val Gly Ser Arg Glu Ala Ala
    50                  55                  60

Leu Ala Leu Thr Pro Ser Phe Val Pro Val Asp Ala Ala Ile Val Gly
65                  70                  75                  80

Ile Val Asp Asp Val His Ala Pro Glu Arg Ala Ser
                85                  90

<210> SEQ ID NO 15
<211> LENGTH: 279
<212> TYPE: DNA
<213> ORGANISM: Artificial Sequence
<220> FEATURE:
```

<223> OTHER INFORMATION: Synthetic DNA sequence selected to encode the
protein sequence of SEQ ID NO:14 while utilizing high-frequency
codons from E. coli, the host organism; YP_003268812

<400> SEQUENCE: 15

```
atgtatctgg gtcgtgtgat tggtaccgtg gtggctgaac gcaaagtggc gggtctggaa        60
ggcgcaaaac tgctgctggt gcaaccgctg gatgacgcac tgagtccggt cggtggtgtg       120
caggcagcag ttgataccgt ccaagcaggt ccggatgacc tggtgtatct ggttggtagc       180
cgtgaagcag ctctggcgct gacgccgtct tttgtgccgg ttgatgcggc cattgtcggc       240
atcgttgatg acgtgcatgc accggaacgc gctagctaa                             279
```

<210> SEQ ID NO 16
<211> LENGTH: 127
<212> TYPE: PRT
<213> ORGANISM: Haliangium ochraceum

<400> SEQUENCE: 16

```
Met Arg Leu Cys Arg Val Leu Gly Ser Val Val Ala Thr Val Lys His
1               5                   10                  15
Pro Val Tyr Asn Gly Leu Pro Leu Met Ile Val Gln Pro Leu Asp Asp
            20                  25                  30
Ala Gly Arg Asp Ala Gly Ala Ser Phe Leu Ala Val Asp Asn Val Gln
        35                  40                  45
Ser Gly Pro Gly Asp Arg Val Leu Val Leu Thr Glu Gly Gly Gly Val
    50                  55                  60
Arg Gln Ile Leu Ala Leu Gly Asp Gln Val Pro Ile Arg Ser Leu Ile
65                  70                  75                  80
Val Gly Val Val Asp Ala Val Asp Gly Val Ala Ala Thr Gly Val Asp
                85                  90                  95
Asp Ala Gly Gly Ala Ala Asp Ser Ala Ala Ala Lys Ser Val Arg
            100                 105                 110
Ala Asp Glu Leu Pro Ala Asp Ala Ser Ala Ala Gly Arg Gly Glu
        115                 120                 125
```

<210> SEQ ID NO 17
<211> LENGTH: 384
<212> TYPE: DNA
<213> ORGANISM: Artificial Sequence
<220> FEATURE:
<223> OTHER INFORMATION: Synthetic DNA sequence selected to encode the
protein sequence of SEQ ID NO:16 while utilizing high-frequency
codons from E. coli, the host organism; YP_003268813

<400> SEQUENCE: 17

```
atgcgtctgt gtcgtgttct gggctccgtc gtcgccaccg tcaagcaccc ggtctacaat        60
ggtctgccgc tgatgatcgt tcaaccgctg gatgacgcag gtcgtgatgc aggcgctagt       120
tttctggctg ttgataacgt ccagtccggt ccgggtgacc gtgtcctggt gctgaccgaa       180
ggtggtggtg tgcgtcagat tctggcactg ggtgatcaag tcccgattcg cagcctgatc       240
gtgggcgtgg ttgatgcagt ggacggtgtt gcagcaacgg tgttgatga cgcaggtggt       300
gcagctgata gcgcagcagc agctaaatct gtccgtgcag atgaactgcc ggcagacgca       360
agcgcggccg gtcgcggcga ataa                                             384
```

<210> SEQ ID NO 18
<211> LENGTH: 96
<212> TYPE: PRT
<213> ORGANISM: Haliangium ochraceum -continued

<400> SEQUENCE: 18

Met Val Leu Gly Lys Val Val Gly Thr Val Val Ala Ser Arg Lys Glu
1               5                   10                  15

Pro Arg Ile Glu Gly Leu Ser Leu Leu Leu Val Arg Ala Cys Asp Pro
            20                  25                  30

Asp Gly Thr Pro Thr Gly Gly Ala Val Val Cys Ala Asp Ala Val Gly
        35                  40                  45

Ala Gly Val Gly Glu Val Val Leu Tyr Ala Ser Gly Ser Ser Ala Arg
    50                  55                  60

Gln Thr Glu Val Thr Asn Asn Arg Pro Val Asp Ala Thr Ile Met Ala
65                  70                  75                  80

Ile Val Asp Leu Val Glu Met Gly Gly Asp Val Arg Phe Arg Lys Asp
                85                  90                  95

<210> SEQ ID NO 19
<211> LENGTH: 291
<212> TYPE: DNA
<213> ORGANISM: Artificial Sequence
<220> FEATURE:
<223> OTHER INFORMATION: Synthetic DNA sequence selected to encode the
      protein sequence of SEQ ID NO:18 while utilizing high-frequency
      codons from E. coli, the host organism; YP_003270183

<400> SEQUENCE: 19
atggtcctgg gtaaagtcgt gggtacggtg gtggcgagcc gcaaagaacc gcgcattgaa      60
ggtctgagcc tgctgctggt ccgtgcctgc gatccggacg gtaccccgac gggtggtgca     120
gtggtttgtg cagatgcagt gggtgcaggt gttggtgaag tcgtgctgta tgcgagtggc     180
agctctgccc gtcagaccga agtcacgaac aatcgcccgg ttgatgcaac cattatggct     240
atcgttgacc tggtcgaaat gggcggtgat gtgcgttttc gcaaagacta a              291

<210> SEQ ID NO 20
<211> LENGTH: 41
<212> TYPE: DNA
<213> ORGANISM: Escherichia coli

<400> SEQUENCE: 20
tctagaaata attttgttta gagaaagagg agaaatacta g                          41

<210> SEQ ID NO 21
<211> LENGTH: 41
<212> TYPE: DNA
<213> ORGANISM: Escherichia coli

<400> SEQUENCE: 21
tctagaaata attttgttta gagaaagagg agaaatacta g                          41

<210> SEQ ID NO 22
<211> LENGTH: 28
<212> TYPE: DNA
<213> ORGANISM: Escherichia coli

<400> SEQUENCE: 22
tttagagatt aaagaggaga atactag                                          28

<210> SEQ ID NO 23
<211> LENGTH: 55
<212> TYPE: PRT
<213> ORGANISM: Artificial Sequence
<220> FEATURE:

<223> OTHER INFORMATION: Part of Tag-GFP construct

<400> SEQUENCE: 23

Met Ala Leu Arg Glu Asp Arg Ile Ala Glu Ile Val Glu Arg Val Leu
1               5                   10                  15

Ala Arg Leu Asp Gly Asn Ser Gly Ser Ser Ala Ala Pro His Ser Gly
            20                  25                  30

Ser Gly Ala Gly Ser Gly Ser Gly Ser Gly Ser Gly Ser Gly Ser Gly
        35                  40                  45

Ser Gly Ser Gly Ser Gly Ser
    50                  55

<210> SEQ ID NO 24
<211> LENGTH: 165
<212> TYPE: DNA
<213> ORGANISM: Artificial Sequence
<220> FEATURE:
<223> OTHER INFORMATION: Part of Tag-GFP construct: synthetic DNA
      sequence used with Tag-GFP construct of SEQ ID: 23 derived from
      the N-terminus of an aldehyde dehydrogenase from H. ochraceum

<400> SEQUENCE: 24
atggcactgc gtgaagatcg tatcgctgaa atcgtggaac gtgtcctggc ccgtctggat      60
ggcaactcgg gctcgtcggc tgcaccgcat agcggctctg gtgcgggtag cggttcgggt     120 tcgggtctg gttctggtag tggcagtggt agtggttcgg gctcc                      165

<210> SEQ ID NO 25
<211> LENGTH: 505
<212> TYPE: PRT
<213> ORGANISM: Artificial Sequence
<220> FEATURE:
<223> OTHER INFORMATION: Part of Full Enzyme-GFP construct; aldehyde
      dehyrdogenase (Protein accession number YP_003270182; Locus tag:
      Hoch_5813)

<400> SEQUENCE: 25

Met Ala Leu Arg Glu Asp Arg Ile Ala Glu Ile Val Glu Arg Val Leu
1               5                   10                  15

Ala Arg Leu Asp Gly Asn Ser Gly Ser Ser Ala Ala Pro His Ser Gly
            20                  25                  30

Ser Gly Ala Pro Ala Ala Thr Ala Gly Gly Ala Ser Leu Asp Ile Pro
        35                  40                  45

Arg Gly Thr Leu Gly Val Tyr Ala Asp Ala Asp Ala Ala Val Asn Ala
    50                  55                  60

Ala Arg Arg Gly Phe Ala Ala Asn Glu Ala Leu Pro Leu Arg Thr Arg
65                  70                  75                  80

Gln Ala Met Ile Asp Ala Met Arg Lys Val Ala Arg Ala His Ile Pro
                85                  90                  95

Glu Leu Ala Arg Tyr Ala Val Ala Glu Thr Gly Leu Gly Arg Tyr Glu
            100                 105                 110

Asp Lys Leu Ala Lys Asn Glu Leu Val Ile Ala Lys Thr Pro Gly Pro
        115                 120                 125

Glu Ile Leu Ala Pro Val Ala Tyr Thr Gly Asp Asp Gly Leu Thr Leu
    130                 135                 140

Thr Glu Arg Ala Pro Tyr Gly Val Ile Gly Ala Ile Thr Pro Cys Thr
145                 150                 155                 160

Asn Pro Thr Glu Thr Val Ile Cys Asn Ala Ile Gly Met Leu Ser Gly
                165                 170                 175

```
Gly Asn Ala Val Val Phe Asn Val His Pro Ser Ala Ala Arg Val Cys
                180                 185                 190

Asn Trp Leu Val His Leu Leu Asn Glu Ala Ile Met Ser Val Gly Gly
            195                 200                 205

Pro Arg Asp Ala Ile Thr Ser Val Glu Ser Pro Thr Ile Asp Ser Ala
        210                 215                 220

Gln Thr Leu Met Thr His Ala Gly Val Arg Leu Val Val Thr Gly
225                 230                 235                 240

Gly Pro Gly Val Val Arg Ala Ala Met Lys Ser Gly Lys Lys Val Ile
                245                 250                 255

Ala Ala Gly Pro Gly Asn Pro Pro Ala Val Asp Glu Thr Ala Asn
            260                 265                 270

Leu Ala Lys Ala Ala Ala Ile Ile Lys Gly Ala Ser Ile Asp Asn
        275                 280                 285

Asn Ile Ile Cys Thr Ala Glu Lys Glu Ile Val Ala Val Ala Ser Ile
    290                 295                 300

Ala Asp Glu Leu Ser Arg Leu Leu Gly Gln Arg Gly Ala Leu Val Leu
305                 310                 315                 320

Gly Asp Ala Gln Val Arg Ala Leu Glu Arg Val Val Leu Asp Gly Glu
                325                 330                 335

His Val Asn Lys Glu Trp Val Gly Lys Asp Ala Ser Arg Ile Ala Glu
            340                 345                 350

Gln Ile Gly Leu Arg Gly His Gly Ser Asp Leu Arg Leu Leu Val Cys
        355                 360                 365

Pro Val Asp Glu Gly His Pro Phe Val Gln His Glu Leu Leu Met Pro
    370                 375                 380

Val Ile Gly Leu Val Arg Val Ser Asp Ala Thr Glu Ala Met Ala Thr
385                 390                 395                 400

Ala Val Arg Val Glu His Gly Phe Cys His Thr Ala Val Met His Ser
                405                 410                 415

Thr His Ile Asp Arg Leu Ser Ala Met Ala Arg Val Cys Asn Ala Ser
            420                 425                 430

Ile Phe Val Lys Asn Asp Cys Asn Leu Ala Gly Leu Gly Leu Gly Gly
        435                 440                 445

Glu Gly Phe Thr Ser Phe Thr Ile Ala Ser Pro Thr Gly Glu Gly Leu
    450                 455                 460

Thr Thr Ala Arg Asp Phe Thr Arg Val Arg Arg Cys Thr Leu Lys Glu
465                 470                 475                 480

Ser Phe Arg Phe Val Gly Ser Gly Ser Gly Ser Gly Ser Gly Ser Gly
                485                 490                 495

Ser Gly Ser Gly Ser Gly Ser Gly Ser
            500                 505

<210> SEQ ID NO 26
<211> LENGTH: 1515
<212> TYPE: DNA
<213> ORGANISM: Artificial Sequence
<220> FEATURE:
<223> OTHER INFORMATION: Synthetic DNA sequence to encode DNA sequence
      used to encode the fused protein of SEQ ID NO:25 as Part of Full
      Enzyme-GFP construct

<400> SEQUENCE: 26
atggctctgc gtgaagatcg tatcgctgaa atcgtggaac gtgtcctggc ccgtctggat     60
ggtaactccg gctcgtcggc tgccccgcac agcggctctg gtgcgccggc ggccaccgct    120
```

```
ggcggtgcga gcctggatat ccgcgtggc acgctgggtg tgtatgcaga tgctgacgca      180
gctgttaacg cagcacgtcg cggttttgca gctaatgaag ccctgccgct gcgtacccgt      240
caggcaatga ttgatgcaat gcgtaaagtt gcgcgcgccc atatcccgga actggcacgt      300
tatgcagtgg ctgaaaccgg cctgggtcgc tacgaagata aactggctaa gaacgaactg      360
gttattgcga agacgccggg cccggaaatc ctggcaccgg tggcatatac gggcgatgac      420
ggtctgaccc tgacggaacg cgccccgtac ggcgttattg gtgcaatcac cccgtgcacg      480
aacccgaccg aaacggtgat tgtaatgcc atcggtatgc tgtcaggcgg taacgcagtg      540
gttttcaatg tgcatccgtc ggcggcccgt gtttgcaact ggctggtcca cctgctgaat      600
gaagctatta tgagtgttgg cggtccgcgc gatgccatta ccagtgtcga atccccgacg      660
atcgactccg ctcaaaccct gatgacgcac gcgggcgttc gtctggtcgt ggttaccggc      720
ggtccgggcg tcgtgcgtgc agctatgaaa tcaggtaaaa aggttatcgc ggcgggtccg      780
ggcaacccgc cggcggttgt ggatgaaacc gctaatctgg cgaaagcagc tgcggccatt      840
atcaagggtg catcgatcga taacaatatt atctgtaccg cggaaaaaga aattgtcgcg      900
gtggccagca tcgcagacga actgtctcgt ctgctgggtc agcgtggtgc gctggtcctg      960
ggcgatgctc aagtgcgtgc gctggaacgc gtggttctgg acggcgaaca tgtgaacaaa     1020
gaatgggttg gcaaggatgc cagccgtatt gcagaacaga tcggtctgcg tggccacggt     1080
tctgatctgc gtctgctggt ctgcccggtg gacgaaggcc atccgtttgt ccaacacgaa     1140
ctgctgatgc cggtgattgg tctggttcgt gtcagcgatg ccaccgaagc aatggctacg     1200
gcggtgcgcg ttgaacatgg cttttgtcac accgcggtga tgcatagtac gcacattgac     1260
cgtctgtccg cgatggcgcg tgtgtgcaat gcgtctatct tcgtcaaaaa cgattgtaat     1320
ctggcaggtc tgggtctggg cggtgaaggt tttacctcat tcacgatcgc atcgccgacc     1380
ggtgaaggtc tgaccacggc acgtgatttc acccgcgttc gtcgctgcac gctgaaagaa     1440
tcttttcgct tcgtgggttc tggtagtggc tctggttcag gcagtggctc aggctcaggc     1500
tcgggcagtg gttct                                                     1515
```

<210> SEQ ID NO 27
<211> LENGTH: 31
<212> TYPE: PRT
<213> ORGANISM: Artificial Sequence
<220> FEATURE:
<223> OTHER INFORMATION: Synthetic protein sequence fused to C-terminus
      of GFP of a Part of Noncognate Tag-GFP construct

<400> SEQUENCE: 27

Gly Ser Gly Ser Gly Ser Gly Ser Gly Ser Glu Pro Glu Asp Asn Glu
1               5                   10                  15

Asp Val Gln Ala Ile Val Lys Ala Ile Met Ala Lys Leu Asn Leu
            20                  25                  30

<210> SEQ ID NO 28
<211> LENGTH: 99
<212> TYPE: DNA
<213> ORGANISM: Artificial Sequence
<220> FEATURE:
<223> OTHER INFORMATION: Synthetic DNA sequence fused to the 3' end of
      the DNA encoding GFP of Part of Noncognate Tag-GFP construct

<400> SEQUENCE: 28
ctcgagggca gcggcagcgg cagcggcagc ggctctgaac cggaagacaa tgaagatgtg       60
caggcaatcg tgaaagcaat tatggctaaa ctgaacctg                              99

<210> SEQ ID NO 29
<211> LENGTH: 30
<212> TYPE: DNA
<213> ORGANISM: Artificial Sequence
<220> FEATURE:
<223> OTHER INFORMATION: Synthetic RBS sequence for operon of Example 4 derived from E.coli

<400> SEQUENCE: 29
ttttgtttag agaaagagga gaaatactag                                      30

<210> SEQ ID NO 30
<211> LENGTH: 93
<212> TYPE: PRT
<213> ORGANISM: Mycobacterium smegmatis

<400> SEQUENCE: 30

Met Ser Ser Asn Ala Ile Gly Leu Ile Glu Thr Lys Gly Tyr Val Ala
1               5                   10                  15

Ala Leu Ala Ala Ala Asp Ala Met Val Lys Ala Ala Asn Val Thr Ile
            20                  25                  30

Thr Asp Arg Gln Gln Val Gly Asp Gly Leu Val Ala Val Ile Val Thr
        35                  40                  45

Gly Glu Val Gly Ala Val Lys Ala Ala Thr Glu Ala Gly Ala Glu Thr
    50                  55                  60

Ala Ser Gln Val Gly Glu Leu Val Ser Val His Val Ile Pro Arg Pro
65                  70                  75                  80

His Ser Glu Leu Gly Ala His Phe Ser Val Ser Ser Lys
                85                  90

<210> SEQ ID NO 31
<211> LENGTH: 282
<212> TYPE: DNA
<213> ORGANISM: Mycobacterium smegmatis

<400> SEQUENCE: 31
atgagcagca atgcaatcgg tctgatcgaa acgaaaggct atgtggcggc actggcagcg    60
gcggatgcaa tggtgaaggc agcaaatgtc accattacgg atcgtcagca agttggcgac   120
ggtctggtgg cggttatcgt caccggcgaa gtgggtgccg ttaaagcggc accgaagca    180 ggcgctgaaa cggcaagtca agtgggtgaa ctggtgtccg ttcatgtcat tccgcgtccg   240
cacagcgaac tgggtgcaca ttttagcgtt agctctaagt aa                      282

<210> SEQ ID NO 32
<211> LENGTH: 28
<212> TYPE: DNA
<213> ORGANISM: Artificial Sequence
<220> FEATURE:
<223> OTHER INFORMATION: Synthetic RBS sequence for operon of Example 4 derived from E.coli

<400> SEQUENCE: 32
tttagagatt aaagaggaga aatactag                                       28

<210> SEQ ID NO 33
<211> LENGTH: 202
<212> TYPE: PRT
<213> ORGANISM: Mycobacterium smegmatis

<400> SEQUENCE: 33

Met Ala Glu Leu Arg Ser Phe Ile Phe Ile Asp Arg Leu Gln Pro Gln
1               5                   10                  15

Thr Met Ser Tyr Leu Gly Thr Trp Ile Lys Gly Ala Leu Pro Arg Ala
            20                  25                  30

Asn Met Ala Ala Gln Ile Ile Glu Val Ala Pro Gly Leu Asp Ile Glu
        35                  40                  45

Gly Val Thr Asp Val Ala Leu Lys His Ala Glu Lys Ala Gly Ile
    50                  55                  60

Leu Val Val Glu Arg Gln Phe Gly Tyr Leu Glu Phe His Gly Glu Thr
65              70                  75                  80

Gly Ala Val Lys Ala Ala Ala Asp Ala Ala Leu Asp Tyr Leu Gly Gly
                85                  90                  95

Asp Pro Asp Ala Ala Val Arg Pro Glu Ile Leu Ala Ser Arg Ile Ile
            100                 105                 110

Ser Ser Ile Asp His Gln His Ala Phe Leu Ile Asn Arg Asn Lys Ile
        115                 120                 125

Gly Ser Met Val Leu Pro Gly Glu Ser Leu Phe Val Leu Glu Val Ala
    130                 135                 140

Pro Ala Ser Tyr Ala Ile Leu Ala Thr Asn Glu Ala Glu Lys Ala Ala
145                 150                 155                 160

Asp Val Lys Val Val Asp Phe Arg Met Ile Gly Ala Thr Gly Arg Val
                165                 170                 175

Tyr Leu Ser Gly Thr Glu Ala Asp Val Arg Gln Ala Ala Asp Ala Ala
            180                 185                 190

Arg Asp Ala Leu Ala Val Leu Gln Gly Ala
        195                 200

<210> SEQ ID NO 34
<211> LENGTH: 609
<212> TYPE: DNA
<213> ORGANISM: Mycobacterium smegmatis

<400> SEQUENCE: 34
atggccgaac tgcgtagctt cattttcatt gaccgcctgc aaccgcaaac gatgtcctat      60
ctgggcacct ggattaaggg tgctctgccg cgtgcgaaca tggcggccca gattatcgaa     120
gttgccccgg gcctggatat tgaaggtgtt accgacgtcg ccctgaaaca tgcagaagtc     180
aaggctggca tcctggtggt tgaacgccaa tttggttatc tggaatttca tggcgaaacg     240
ggtgcggtga agcagctgc ggatgccgca ctggactacc tggtggtga tccgacgct      300 gcagttcgtc cggaaattct ggcctctcgc attatcagct ctatcgatca tcagcacgca     360
tttctgatta accgtaataa gatcggcagt atggtcctgc cgggtgaatc cctgttcgtg     420
ctggaagttg ctccggcgag ctatgcgatt ctggcgacca tgaagcgga aaaagccgca     480 gatgttaagg tcgtggactt tcgtatgatc ggtgcaaccg gtcgtgtcta cctgtcgggc     540
acggaagctg atgtgcgtca ggctgcagat gcagcacgcg acgcactggc agtgctgcaa     600
ggtgcctaa                                                             609

<210> SEQ ID NO 35
<211> LENGTH: 27
<212> TYPE: DNA
<213> ORGANISM: Artificial Sequence
<220> FEATURE:

<223> OTHER INFORMATION: Synthetic RBS sequence for operon of Example 4
      derived from E.coli

<400> SEQUENCE: 35
tttagagtca cacaggaaac ctactag        27

<210> SEQ ID NO 36
<211> LENGTH: 87
<212> TYPE: PRT
<213> ORGANISM: Mycobacterium smegmatis

<400> SEQUENCE: 36

Met Leu Arg Ala Thr Val Thr Gly Asn Val Trp Ser Thr Arg Arg Ile
1               5                   10                  15

Glu Gly Ile Pro Ala Gly Ala Phe Leu Glu Val Glu Val Glu Gly Thr
            20                  25                  30

Gly Ser Arg Met Ile Ala Phe Asp Val Leu Gly Ser Gly Val Gly Glu
        35                  40                  45

His Val Leu Ile Ala Gln Gly Ser Val Ala Ser Ser Trp Phe Thr Gly
    50                  55                  60

Thr Pro Pro Ile Asp Ala Leu Ile Ile Gly Ser Ile Asp Thr Arg
65                  70                  75                  80

Ser Asp Ser Asn Pro Ala Glu
                85

<210> SEQ ID NO 37
<211> LENGTH: 264
<212> TYPE: DNA
<213> ORGANISM: Mycobacterium smegmatis

<400> SEQUENCE: 37
atgctgcgtg ctaccgttac cggcaatgtc tggtctaccc gtcgtatcga aggcatcccg        60
gctggtgctt ttctggaagt ggaagtcgaa ggcaccggtt cacgtatgat tgcctttgat       120
gtcctgggct cgggtgtggg cgaacatgtt ctgatcgcgc agggtagcgt tgccagctct       180
tggttcaccg gtacgccgcc gccgattgac gcactgatta tcggtagtat cgatacgcgc       240
agtgactcca acccggctga ataa                                              264

<210> SEQ ID NO 38
<211> LENGTH: 471
<212> TYPE: PRT
<213> ORGANISM: Artificial Sequence
<220> FEATURE:
<223> OTHER INFORMATION: Synthetic non-native enzyme Rubisco protein
      sequence

<400> SEQUENCE: 38

Met Ala Ala Lys Lys Tyr Ser Ala Gly Val Lys Glu Tyr Arg Gln Thr
1               5                   10                  15

Tyr Trp Thr Pro Asp Tyr Val Pro Leu Asp Thr Asp Leu Leu Ala Cys
            20                  25                  30

Phe Lys Val Thr Pro Gln Pro Gly Val Pro Arg Glu Glu Ala Ala Ala
        35                  40                  45

Ala Val Ala Ala Glu Ser Ser Thr Gly Thr Trp Thr Thr Val Trp Thr
    50                  55                  60

Asp Leu Leu Thr Asp Met Asp Tyr Tyr Lys Gly Arg Cys Tyr Arg Ile
65                  70                  75                  80

Glu Asp Val Pro Gly Asp Glu Ser Phe Tyr Ala Phe Ile Ala Tyr
                85                  90                  95

Pro Leu Asp Leu Phe Glu Gly Ser Val Thr Asn Val Leu Thr Ser
            100                 105                 110

Leu Val Gly Asn Val Phe Gly Phe Lys Ala Leu Arg Ala Leu Arg Leu
            115                 120                 125

Glu Asp Ile Arg Phe Pro Met Ala Tyr Val Lys Thr Cys Ala Gly Pro
        130                 135                 140

Pro His Gly Ile Gln Val Glu Arg Asp Lys Met Asn Lys Tyr Gly Arg
145                 150                 155                 160

Pro Leu Leu Gly Cys Thr Ile Lys Pro Lys Leu Gly Leu Ser Ala Lys
                165                 170                 175

Asn Tyr Gly Arg Ala Val Tyr Glu Cys Leu Arg Gly Gly Leu Asp Phe
            180                 185                 190

Thr Lys Asp Asp Glu Asn Ile Asn Ser Gln Pro Phe Gln Arg Trp Arg
        195                 200                 205

Asp Arg Phe Glu Phe Val Ala Glu Ala Val Glu Lys Ala Glu Ala Glu
    210                 215                 220

Thr Gly Glu Arg Lys Gly His Tyr Leu Asn Val Thr Ala Pro Thr Pro
225                 230                 235                 240

Glu Glu Met Tyr Lys Arg Ala Glu Phe Ala Lys Glu Leu Gly Ala Pro
                245                 250                 255

Ile Ile Met His Asp Tyr Ile Thr Gly Gly Phe Thr Ala Asn Thr Gly
            260                 265                 270

Leu Ala Lys Trp Cys Arg Asp Asn Gly Val Leu Leu His Ile His Arg
        275                 280                 285

Ala Met His Ala Val Ile Asp Arg His Pro Asn His Gly Ile His Phe
    290                 295                 300

Arg Val Leu Ala Lys Cys Leu Arg Leu Ser Gly Gly Asp His Leu His
305                 310                 315                 320

Thr Gly Thr Val Val Gly Lys Leu Glu Gly Asp Arg Ala Ser Thr Leu
                325                 330                 335

Gly Tyr Ile Asp Leu Leu Arg Glu Ser Phe Ile Pro Glu Asp Arg Ser
            340                 345                 350

Arg Gly Ile Phe Phe Asp Gln Asp Trp Gly Ser Met Pro Gly Val Phe
        355                 360                 365

Ala Val Ala Ser Gly Gly Ile His Val Trp His Met Pro Ala Leu Val
    370                 375                 380

Ser Ile Phe Gly Asp Asp Ser Val Leu Gln Phe Gly Gly Gly Thr Leu
385                 390                 395                 400

Gly His Pro Trp Gly Asn Ala Ala Gly Ala Ala Asn Arg Val Ala
                405                 410                 415

Leu Glu Ala Cys Val Gln Ala Arg Asn Glu Gly Arg Asp Ile Glu Lys
            420                 425                 430

Glu Gly Lys Asp Ile Leu Thr Glu Ala Ala Lys His Ser Pro Glu Leu
        435                 440                 445

Ala Ile Ala Leu Glu Thr Trp Lys Glu Ile Lys Phe Glu Phe Asp Thr
    450                 455                 460

Val Asp Lys Leu Asp Thr Gln
465                 470

<210> SEQ ID NO 39
<211> LENGTH: 1419
<212> TYPE: DNA
<213> ORGANISM: Artificial Sequence
<220> FEATURE:

<223> OTHER INFORMATION: Synthetic non-native enzyme Rubisco DNA sequence

<400> SEQUENCE: 39

```
catatggcag cgaaaaaata cagcgcaggc gtgaaagaat accgccaaac ctactggact    60
cccgattatg ttcccctcga tacgacctc ctggcctgct ttaaagttac cccccagcca   120
ggtgtgcccc gcgaagaggc agcagctgca gtcgcagcag aaagctcgac tggcacctgg   180
accacggttt ggaccgacct gctcacggat atggactact ataagggtcg ctgttaccgc   240
atcgaggatg tgcctggcga tgacgaaagc ttttacgctt tcattgcata tccattggat   300
ctgtttgaag agggctcggt tactaacgtg ctgaccagtc tcgtcggtaa tgttttggc   360
ttcaaagccc tgcgcgcgct ccgcttggaa gatatccgct tcccgatggc ctacgtgaag   420
acctgcgcag tcccccgca tggcattcaa gtcgaacgcg ataaaatgaa caagtatggt   480
cgccccttgc tgggctgcac gatcaaaccg aagctgggtc tctcggctaa aaattacggc   540
cgcgccgtgt atgaatgttt gcgcggcggt ctggattta ccaaggatga cgagaacatt   600
aatagccagc ccttccaacg ctggcgcgat cgctttgaat ttgtggcgga agctgtcgag   660
aaagcagaag ccgagacggg cgagcgcaag ggccattacc tgaacgtcac cgcgcctacg   720
ccagaagaga tgtataaacg cgctgaattt gcaaaggagc tcggcgctcc catcattatg   780
cacgattaca tcaccggcgg tttcactgcc aacaccggtt tggcgaaatg gtgccgcgac   840
aatggcgttc tcttgcacat ccatcgcgcc atgcacgcgg tgattgatcg ccacccgaat   900
catggcatcc actttcgcgt cctcgcgaaa tgtttgcgcc tgagtggcgg tgatcacttg   960
catacgggta ctgtggtcgg caagttggaa ggtgaccgcg ccagcaccct gggctatatt  1020
gatctgctcc gcgagagctt tatcccgaaa gatcgctcgc gcggcatctt tttcgatcag  1080
gactggggct cgatgccggg tgtgttcgca gtcgctagtg gtggtatcca tgtgtggcac  1140
atgccggcgc tcgtcagtat ttttggcgat gacagcgtgc tgcagttcgg tggtggtacc  1200
ctcggtcatc cttggggtaa cgctgcaggt gcagcagcta atcgcgtcgc tctggaggca  1260
tgcgttcaag cccgcaacga aggtcgcgac atcgaaaaag agggcaagga tattctcact  1320
gaggcagcca agcacagccc ggaactcgca atcgccttgg aaacgtggaa agagattaag  1380
tttgaatttg atacggtcga caaactggat actcaatag                          1419
```

<210> SEQ ID NO 40
<211> LENGTH: 102
<212> TYPE: PRT
<213> ORGANISM: Thermosynechococcus elongatus

<400> SEQUENCE: 40

```
Met Pro Ile Ala Val Gly Met Ile Glu Thr Arg Gly Phe Pro Ala Val
1               5                   10                  15

Val Glu Ala Ala Asp Ala Met Val Lys Ala Ala Arg Val Thr Leu Val
            20                  25                  30

Gly Tyr Glu Lys Ile Gly Ser Gly Arg Val Thr Val Ile Val Arg Gly
        35                  40                  45

Asp Val Ser Glu Val Gln Ala Ser Val Ala Ala Gly Val Asp Ser Ala
    50                  55                  60

Lys Arg Val Asn Gly Gly Glu Val Leu Ser Thr His Ile Ile Ala Arg
65                  70                  75                  80

Pro His Glu Asn Leu Glu Tyr Val Leu Pro Ile Arg Tyr Thr Glu Ala
                85                  90                  95
```

Val Glu Gln Phe Arg Asn
            100

<210> SEQ ID NO 41
<211> LENGTH: 309
<212> TYPE: DNA
<213> ORGANISM: Artificial sequence
<220> FEATURE:
<223> OTHER INFORMATION: Synthetic hexamer DNA sequence for synthetic
      operon of Example 6 from Thermosynechococcus elongatus BP-1:
      NC_004113. This sequence has been codon-optimized for expression
      in E. coli

<400> SEQUENCE: 41
atgccaattg ctgtgggaat gattgaaacg cgcggatttc ccgccgtcgt cgaagcagca      60
gatgcaatgg tcaaagccgc tcgggttacc ctggtgggct acgaaaaaat tgggagtggg     120
cgggtcaccg tgattgtgcg gggtgatgtc tccgaagtgc aagcgtcagt agctgccggg     180
gtcgattctg ccaagcgtgt caatggcgga gaggtgctgt ccacgcacat tattgcccgt     240
ccccacgaaa accttgagta cgtattgccc attcgctata ccgaggcagt ggagcaattc     300
cgaaactaa                                                             309

<210> SEQ ID NO 42
<211> LENGTH: 253
<212> TYPE: PRT
<213> ORGANISM: Thermosynechococcus elongatus

<400> SEQUENCE: 42

Met Glu Arg Arg Asp Asp Phe Thr Asp Leu Ala Leu Gly Leu Val Ser
1               5                   10                  15

Val Gln Ser Phe Pro Ala Ile Val Gly Ile Ala Asp His Met Leu Lys
            20                  25                  30

Ser Ser Asp Val Leu Leu Val Gly Tyr Glu Lys Ile Gly Gly Gly His
        35                  40                  45

Cys Thr Ala Ile Val Arg Gly Arg Ile Ala Asp Val Arg Leu Ala Val
    50                  55                  60

Glu Glu Gly Ala Glu Arg Ala Gln Gln Phe Gly Gln Glu Leu Ser Thr
65                  70                  75                  80

Leu Val Ile Pro Arg Pro Asp Pro Asn Leu Glu Lys Ile Leu Pro Ile
                85                  90                  95

Gly Ser Leu Leu Ala Gln Ile Ala Ser Lys Ser Arg Gly His Arg Leu
            100                 105                 110

Ser Ser His Ala Val Gly Leu Leu Glu Thr Arg Gly Phe Pro Ala Met
        115                 120                 125

Val Gly Ala Ala Asp Ala Met Leu Lys Ala Ala Asp Val Met Leu Thr
    130                 135                 140

Ala Tyr Glu Thr Ile Gly Ala Gly Leu Cys Thr Ala Ile Ile Arg Gly
145                 150                 155                 160

Thr Ala Ser Asn Thr Ala Ile Ala Leu Glu Ala Gly Met Ala Glu Ala
                165                 170                 175

Asp Arg Ile Gly Glu Leu His Ala Val Met Leu Val Pro Arg Pro Leu
            180                 185                 190

Glu Asp Leu Asp Gln Ser Leu Pro Leu Ala Pro Ala Leu Gln Arg Glu
        195                 200                 205

Leu Gln Pro Leu Arg Leu Pro Leu Thr Leu Lys Gln Lys Glu Thr Glu
    210                 215                 220

Pro Leu Ala Leu Gln Gly Ala Ala Gln Ala Ser Val Ala Val Glu Ala
225                 230                 235                 240

Ala Ala Glu Arg Val Pro Val Asp Pro Pro Ala Asn Pro
                245                 250

<210> SEQ ID NO 43
<211> LENGTH: 762
<212> TYPE: DNA
<213> ORGANISM: Artificial sequence
<220> FEATURE:
<223> OTHER INFORMATION: Synthetic tandem domain DNA sequence for
      synthetic operon of Example 6 from Thermosynechococcus elongatus
      BP-1: NC_004113. This sequence has been codon-optimized for
      expression in E. coli

<400> SEQUENCE: 43

```
atggagcgac gggatgactt tacggattta gccttagggc tggtctcagt ccagagcttt     60
ccggcgatcg ttggcattgc cgatcacatg ctcaaatcct ccgatgtcct cctagtgggc    120
tatgaaaaaa ttggcggtgg tcactgtacc gcgatcgtcc gcgggcgaat tgccgatgtg    180
cgccttgcgg tagaagaggg ggccgagcgg gcgcagcaat tcggtcagga actgagtacg    240
ttagtgattc cccgacccga tcccaaccta gagaaaattc tccccattgg cagtctcctt    300
gcccagattg cttctaaaag tcgcggccat cgcctcagta gccatgccgt aggtcttctg    360
gaaacccggg gatttccagc catggtgggg cagccgatg ccatgctcaa ggcagcggat     420
gtgatgctga cggcctacga aaccattggg cagggttat gtacggctat tattcgcggt     480
acggcctcca ataccgcgat cgccctcgag gccggaatgg cagaagccga tcgcattggt    540
gaactccatg cggtgatgtt ggtgccccgt cccttgagg atttggatca atccttgccc     600
ttggcacctg ccctccaacg ggaactgcaa ccctgcgtc tccccttac cctcaagcaa      660 aaagaaaccg aacccttgc cctccaaggg gcggctcaag cgagtgtggc tgtggaagcc     720
gccgccgaaa gggtgcccgt cgaccccccct gccaatccct ga                      762
```

<210> SEQ ID NO 44
<211> LENGTH: 99
<212> TYPE: PRT
<213> ORGANISM: Thermosynechococcus elongatus

<400> SEQUENCE: 44

Met Lys Ile Ala Arg Val Cys Gly Thr Val Thr Ser Thr Gln Lys Glu
1               5                   10                  15

Asp Thr Leu Thr Gly Val Lys Phe Leu Val Leu Gln Tyr Leu Gly Glu
            20                  25                  30

Asp Gly Glu Phe Leu Pro Asp Tyr Glu Val Ala Ala Asp Thr Val Gly
        35                  40                  45

Ala Gly Gln Asp Glu Trp Val Leu Val Ser Arg Gly Ser Ala Ala Arg
    50                  55                  60

His Ile Ile Asn Gly Thr Asp Lys Pro Ile Asp Ala Ala Val Val Ala
65                  70                  75                  80

Ile Ile Asp Thr Val Ser Arg Asp Asn Tyr Leu Leu Tyr Ser Lys Arg
                85                  90                  95

Thr Gln Tyr

<210> SEQ ID NO 45
<211> LENGTH: 300
<212> TYPE: DNA
<213> ORGANISM: Artificial sequence
<220> FEATURE:
<223> OTHER INFORMATION: Synthetic pentamer DNA sequence for synthetic operon of Example 6 from Thermosynechococcus elongatus BP-1: NC_004113. This sequence has been codon-optimized for expression in E. coli

<400> SEQUENCE: 45

```
gtgaaaatcg cgcgagtgtg cggcaccgtt accagtactc aaaaagaaga caccttaacg    60
ggagtcaagt ttctcgtctt gcaatatttg ggtgaggacg gcgaattttt acccgactac   120
gaagtggctg cggatacggt tggtgcagga caggatgagt gggtattggt aagccgaggc   180
agtgccgccc gccatattat caatggcacc gacaaaccca ttgacgcagc cgttgtcgcc   240
attattgaca ccgtaagtcg ggataattat ttgctctaca gcaaacgtac ccagtattag   300
```

<210> SEQ ID NO 46
<211> LENGTH: 19
<212> TYPE: DNA
<213> ORGANISM: Artificial sequence
<220> FEATURE:
<223> OTHER INFORMATION: Synthetic B1010 ribosome binding site

<400> SEQUENCE: 46

```
tttaagaagg agatatacc                                                  19
```

<210> SEQ ID NO 47
<211> LENGTH: 20
<212> TYPE: DNA
<213> ORGANISM: Artificial sequence
<220> FEATURE:
<223> OTHER INFORMATION: Synthetic B1001 ribosome binding site

<400> SEQUENCE: 47

```
ggctaacata gggtggatct                                                 20
```

<210> SEQ ID NO 48
<211> LENGTH: 238
<212> TYPE: PRT
<213> ORGANISM: artificial
<220> FEATURE:
<223> OTHER INFORMATION: Synthetic Protein sequence of SuperFolderGFP used in the SFGFP-CcmK2 fusion proteins

<400> SEQUENCE: 48

```
Met Arg Lys Gly Glu Glu Leu Phe Thr Gly Val Val Pro Ile Leu Val
  1               5                  10                  15

Glu Leu Asp Gly Asp Val Asn Gly His Lys Phe Ser Val Arg Gly Glu
                 20                  25                  30

Gly Glu Gly Asp Ala Thr Asn Gly Lys Leu Thr Leu Lys Phe Ile Cys
             35                  40                  45

Thr Thr Gly Lys Leu Pro Val Pro Trp Pro Thr Leu Val Thr Thr Leu
         50                  55                  60

Thr Tyr Gly Val Gln Cys Phe Ala Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Ser Phe Lys Asp Asp Gly Thr Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140
```

```
Phe Asn Ser His Asn Val Tyr Ile Thr Ala Asp Lys Gln Lys Asn Gly
145                 150                 155                 160

Ile Lys Ala Asn Phe Lys Ile Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Val Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

<210> SEQ ID NO 49
<211> LENGTH: 714
<212> TYPE: DNA
<213> ORGANISM: Artificial sequence
<220> FEATURE:
<223> OTHER INFORMATION: Synthetic construct sfGFP_iGEM gene, complete cds [synthetic contstruct, GI:532528632]

<400> SEQUENCE: 49

```
atgcgtaaag gcgaagagct gttcactggt gtcgtcccta ttctggtgga actggatggt    60
gatgtcaacg gtcataagtt tccgtgcgt ggcgagggtg aaggtgacgc aactaatggt   120
aaactgacgc tgaagttcat ctgtactact ggtaaactgc cggtaccttg ccgactctg   180
gtaacgacgc tgacttatgg tgttcagtgc tttgctcgtt atccggacca tatgaagcag   240
catgacttct tcaagtccgc catgccggaa ggctatgtgc aggaacgcac gatttccttt   300
aaggatgacg gcacgtacaa aacgcgtgcg gaagtgaaat ttgaaggcga tacccctggta   360
aaccgcattg agctgaaagg cattgacttt aagaagacg gcaatatcct gggccataag   420
ctggaataca attttaacag ccacaatgtt tacatcaccg ccgataaaca aaaaaatggc   480
attaaagcga attttaaaat tcgccacaac gtggaggatg gcagcgtgca gctggctgat   540
cactaccagc aaaacactcc aatcggtgat ggtcctgttc tgctgccaga caatcactat   600
ctgagcacgc aaagcgttct gtctaaagat ccgaacgaga aacgcgatca tatggttctg   660
ctggagttcg taaccgcagc gggcatcacg catggtatgg atgaactgta caaa         714
```

<210> SEQ ID NO 50
<211> LENGTH: 55
<212> TYPE: PRT
<213> ORGANISM: Haliangium ochraceum

<400> SEQUENCE: 50

```
Ala Gly Leu Gly Gln Ala Ala Asp Ala Ala Thr Gln His Ala His Ala
1               5                   10                  15

Tyr Ala Ala Ala Pro Arg Gln Ser Ala Ser Glu Ser Ala Ser Gly Gly
                20                  25                  30

Gly Arg Asp Asp Leu Val Arg Val Ile Arg Glu Glu Leu Val Arg Ala
            35                  40                  45

Leu Ala Gly Glu Glu Ser Arg
        50                  55
```

<210> SEQ ID NO 51
<211> LENGTH: 16
<212> TYPE: PRT
<213> ORGANISM: Haliangium ochraceum

<400> SEQUENCE: 51

Arg Asp Asp Leu Val Arg Val Ile Arg Glu Glu Leu Val Arg Ala Leu
1               5                   10                  15

<210> SEQ ID NO 52
<211> LENGTH: 165
<212> TYPE: DNA
<213> ORGANISM: Haliangium ochraceum

<400> SEQUENCE: 52

```
gcgggtctgg gtcaggcagc agacgcagct acccaacatg ctcacgcata cgcagcagca      60
ccgcgtcagt cagcttcgga aagcgcatct ggcggtggcc gtgatgacct ggtccgtgtg     120
atccgcgaag aactggtgcg tgccctggca ggtgaagaat cccgc                     165
```

<210> SEQ ID NO 53
<211> LENGTH: 18
<212> TYPE: PRT
<213> ORGANISM: Haliangium ochraceum

<400> SEQUENCE: 53

Ala Leu Arg Glu Asp Arg Ile Ala Glu Ile Val Glu Arg Val Leu Ala
1               5                   10                  15

Arg Leu

<210> SEQ ID NO 54
<211> LENGTH: 54
<212> TYPE: DNA
<213> ORGANISM: Haliangium ochraceum

<400> SEQUENCE: 54

```
gcgctgcgcg aagatcgcat tgcggaaatt gtggaacgcg tgctggcgcg cctg            54
```

<210> SEQ ID NO 55
<211> LENGTH: 28
<212> TYPE: DNA
<213> ORGANISM: Artificial sequence
<220> FEATURE:
<223> OTHER INFORMATION: Synthetic Ribosomal binding site for BMC-H

<400> SEQUENCE: 55

```
tctagagaaa gaggagaaat actagatg                                         28
```

<210> SEQ ID NO 56
<211> LENGTH: 31
<212> TYPE: DNA
<213> ORGANISM: Artificial
<220> FEATURE:
<223> OTHER INFORMATION: Synthetic Ribosomal binding site for BMC-T

<400> SEQUENCE: 56

```
tctagagatt aaagaggaga aatactagat g                                     31
```

<210> SEQ ID NO 57
<211> LENGTH: 30
<212> TYPE: DNA
<213> ORGANISM: Artificial
<220> FEATURE:
<223> OTHER INFORMATION: Synthetic Ribosomal binding site for BMC-P

<400> SEQUENCE: 57

```
tctagagtca cacaggaaac ctactagatg                                       30
```

<210> SEQ ID NO 58
<211> LENGTH: 3332
<212> TYPE: DNA
<213> ORGANISM: Artificial
<220> FEATURE:
<223> OTHER INFORMATION: Full sequence of the synthetic H. ochraceum operon

<400> SEQUENCE: 58

```
aataattttg tttagagaaa gaggagaaat actagatggc ggacgcactg ggtatgattg     60
aagttcgtgg ttttgttggt atggtggaag cggcggatgc tatggtgaaa gcggctaaag    120
ttgaactgat tggttatgaa aaaaccggcg gtggctacgt gacggcagtg gttcgtggtg    180
atgtcgcagc agttaaggca gctaccgaag ccggtcagcg tgcagcagaa cgtgttggtg    240
aagtcgtggc agttcatgtc atcccgcgtc cgcacgtgaa cgttgatgca gctctgccgc    300
tgggtcgtac gccgggtatg gacaaaagcg cgtaatttag agattaaaga ggagaaatac    360
tagatggacc acgctccgga acgctttgat gcgacccccgc cggcaggtga accggaccgc    420
ccggcactgg gtgtgctgga actgacctca attgctcgtg gtatcaccgt tgcggatgcg    480
gccctgaaac gtgcaccgag tctgctgctg atgtcccgcc cggtcagctc tggcaagcat    540
ctgctgatga tgcgtggcca ggtggcagaa gttgaagaat caatgattgc agctcgcgaa    600
atcgctggtg caggttcggg tgctctgctg gatgaactgg aactgccgta tgcgcacgaa    660
caactgtggc gctttctgga cgcaccggtg gttgcagatg catgggaaga agacaccgaa    720
agcgtcatta tcgtggaaac cgcgacggtg tgcgcggcca ttgatagtgc cgacgcagct    780
ctgaaaacgg caccggtcgt gctgcgtgat atgcgcctgg ccattggtat cgctggcaag    840
gcgtttttca ccctgacggg tgaactggca gacgtggaag cggccgcaga agttgtccgt    900
gaacgttgcg gtgcacgtct gctggaactg gcatgtatcg cacgcccggt tgatgaactg    960
cgtggccgcc tgtttttcta atttagagat taaagaggag aaatactaga tggaactgcg   1020
tgcttatacg gtcctggatg ccctgcagcc gcaactggtc gcctttctgc aaacggtgtc   1080
aacgggtttc atgccgatgg aacagcaagc gagcgttctg gtcgaaattg caccgggtat   1140
cgctgtcaac cagctgaccg acgcagcact gaaagcaacg cgttgccagc cgggtctgca   1200
aattgtggaa cgtgcgtatg gcctgatcga aatgcatgat gacgatcagg gtcaagttcg   1260
tgcagctggt gacgcaatgc tggcacacct gggtgcacgt gaagctgatc gtctggcacc   1320
gcgtgtggtt agctctcaga ttatcaccgg tattgacggc catcagagtc aactgatcaa   1380
ccgtatgcgc cacggtgata tgattcaggc aggccaaacg ctgtatatcc tggaagttca   1440
tccggcaggt tacgcagcac tggcagctaa tgaagccgaa aaagcggccc cgattaagct   1500
gctggaagtc gtgacctttg gtgcattcgg tcgtctgtgg ctgggtggtg gtgaagcaga   1560
aatcgcagaa gcagctcgtg cggcagaagg tgcactggct ggtctgtccg gccgtgataa   1620
tcgcggctaa tttagagatt aaagaggaga aatactagat gtcaatcacc ctgcgcacct   1680
atatctttct ggacgccctg caaccgcaac tggcaacctt catcggcaaa acggctcgtg   1740
gcttcctgcc ggtcccgggt caggcaagcc tgtgggtgga aattgctccg ggtattgcga   1800
tcaaccgtgt gaccgatgcg gccctgaaag ctacgaaggt gcagccggcg gttcaagtgg   1860
ttgaacgcgc gtatggcctg ctggaagttc atcacttcga tcagggcgaa gtcctggcag   1920
ctggtagtac catcctggac aaactggaag ttcgtgaaga aggtcgcctg aagccgcagg   1980
tgatgaccca tcaaattatc cgtgctgttg aagcgtatca gacgcaaatt atcaaccgca   2040
```

```
atagtcaggg catgatgatt ctgccggtg  aatccctgtt  tatcctggaa  acccaaccgg  2100
caggttacgc agtcctggca gccaatgaag ccgaaaaagc  agctaacgtt  cacctggtca  2160
atgtgacgcc gtatggcgca ttcggtcgtc tgtacctggc  cggctcagaa  gcagaaattg  2220
atgcggccgc agaagctgcg gaagccgcaa tccgcagcgt  ttctggtgtc  gcgcaggaat  2280
cgtttcgtga ccgctaattt agagtcacac aggaaaccta  ctagatgtat  ctgggtcgtg  2340
tgattggtac cgtggtggct gaacgcaaag tggcgggtct  ggaaggcgca  aaactgctgc  2400
tggtgcaacc gctggatgac gcactgagtc cggtcggtgg  tgtgcaggca  gcagttgata  2460
ccgtccaagc aggtccggat gacctggtgt atctggttgg  tagccgtgaa  gcagctctgg  2520
cgctgacgcc gtcttttgtg ccggttgatg cggccattgt  cggcatcgtt  gatgacgtgc  2580
atgcaccgga acgcgctagc taatttagag tcacacagga  aacctactag  atgcgtctgt  2640
gtcgtgttct gggctccgtc gtcgccaccg tcaagcaccc  ggtctacaat  ggtctgccgc  2700
tgatgatcgt tcaaccgctg gatgacgcag gtcgtgatgc  aggcgctagt  tttctggctg  2760
ttgataacgt ccagtccggt ccgggtgacc gtgtcctggt  gctgaccgaa  ggtggtggtg  2820
tgcgtcagat tctggcactg ggtgatcaag tcccgattcg  cagcctgatc  gtgggcgtgg  2880
ttgatgcagt ggacggtgtt gcagcaacgg gtgttgatga  cgcaggtggt  gcagctgata  2940
gcgcagcagc agctaaatct gtccgtgcag atgaactgcc  ggcagacgca  agcgcggccg  3000
gtcgcggcga ataatttaga gtcacacagg aaacctacta  gatggtcctg  ggtaaagtcg  3060
tgggtacggt ggtggcgagc cgcaaagaac cgcgcattga  aggtctgagc  ctgctgctgg  3120
tccgtgcctg cgatccggac ggtaccccga cgggtggtgc  agtggtttgt  gcagatgcag  3180
tgggtgcagg tgttggtgaa gtcgtgctgt atgcgagtgg  cagctctgcc  cgtcagaccg  3240
aagtcacgaa caatcgcccg gttgatgcaa ccattatggc  tatcgttgac  ctggtcgaaa  3300
tgggcggtga tgtgcgtttt cgcaaagact aa                      3332
```